(12) United States Patent
Hong et al.

(10) Patent No.: US 10,519,166 B2
(45) Date of Patent: Dec. 31, 2019

(54) HETEROCYCLIC COMPOUND AND ORGANIC LIGHT EMITTING DEVICE COMPRISING THE SAME

(71) Applicant: LG Chem, Ltd., Seoul (KR)

(72) Inventors: Wanpyo Hong, Daejeon (KR); Dongheon Kim, Daejeon (KR); Hyoungcheul Kim, Daejeon (KR); Yongbum Cha, Daejeon (KR); Yun Hwan Kim, Daejeon (KR)

(73) Assignee: LG Chem, Ltd. (KR)

( * ) Notice: Subject to any disclaimer, the term of this patent is extended or adjusted under 35 U.S.C. 154(b) by 182 days.

(21) Appl. No.: 15/562,581

(22) PCT Filed: Oct. 26, 2016

(86) PCT No.: PCT/KR2016/012078
§ 371 (c)(1),
(2) Date: Sep. 28, 2017

(87) PCT Pub. No.: WO2017/074018
PCT Pub. Date: May 4, 2017

(65) Prior Publication Data
US 2018/0086775 A1    Mar. 29, 2018

(30) Foreign Application Priority Data
Oct. 26, 2015 (KR) .......................... 10-2015-0148680

(51) Int. Cl.
*C07D 495/14* (2006.01)
*C07D 333/76* (2006.01)
*C07D 409/14* (2006.01)
*C07D 495/04* (2006.01)
*C09K 11/06* (2006.01)
*H01L 51/00* (2006.01)
*H01L 51/50* (2006.01)
*C07D 333/78* (2006.01)
*C07D 495/22* (2006.01)

(52) U.S. Cl.
CPC ........ *C07D 495/14* (2013.01); *C07D 333/76* (2013.01); *C07D 333/78* (2013.01); *C07D 409/14* (2013.01); *C07D 495/04* (2013.01); *C07D 495/22* (2013.01); *C09K 11/06* (2013.01); *H01L 51/0074* (2013.01); *H01L 51/0094* (2013.01); *H01L 51/5012* (2013.01); *C09K 2211/1092* (2013.01); *H01L 51/5088* (2013.01)

(58) Field of Classification Search
CPC ..................................................... C07D 333/76
See application file for complete search history.

(56) References Cited

U.S. PATENT DOCUMENTS

| | | | |
|---|---|---|---|
| 9,695,190 B2 | 7/2017 | Mitchell et al. | |
| 2013/0007441 A1 | 1/2013 | Stern et al. | |
| 2013/0237676 A1 | 9/2013 | Hsu et al. | |
| 2015/0322208 A1 | 11/2015 | Mitchell et al. | |

FOREIGN PATENT DOCUMENTS

| | | |
|---|---|---|
| KR | 20150036247 A | 4/2015 |
| KR | 20150046262 A | 4/2015 |
| WO | 2015013656 A2 | 1/2015 |

OTHER PUBLICATIONS

Chemical Abstract Compound, STN express, CAS Registry No. 350613-49-9, entered Aug. 7, 2001.
Chemical Abstract Compound, STN express, CAS Registry No. 1809511-63-4, Oct. 9, 2015.
Christensen et al., "Diindenothienoacene-tetrathiafulvalene redox systems", The Royal Society of Chemistry, RSC Advances, May 2018, vol. 5, pp. 49748-49751.
Search report from International Application No. PCT/KR2016/012078, dated Aug. 29, 2017.
Zgou et al., "DFT/B3LYP study of bridging effect on structural and electronic properties of a short n-conjugated systems based on thiophene and phenylene", Journal of Computational Mehtods in Molecular Design, 2013, vol. 3, No. 4, pp. 22-29.

*Primary Examiner* — Peter F Godenschwager
(74) *Attorney, Agent, or Firm* — Lerner, David, Littenberg, Krumholz & Mentlik, LLP

(57) ABSTRACT

The present specification provides a heterocyclic compound and an organic light emitting device including the same.

17 Claims, 2 Drawing Sheets

[Figure 1]
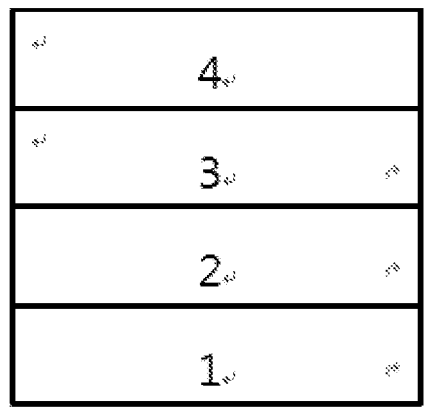
[Figure 2]
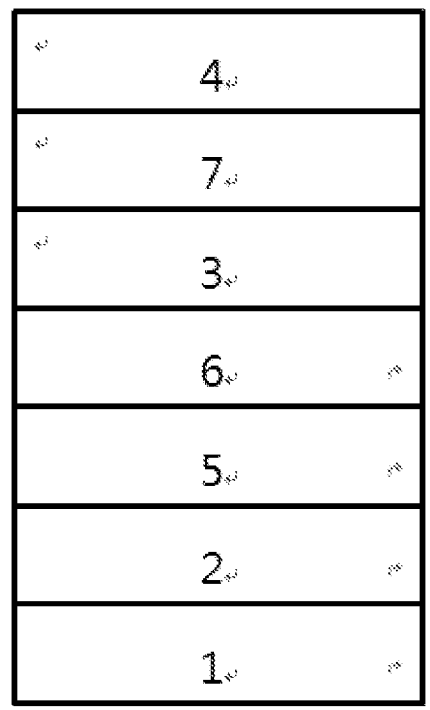

[Figure 3]
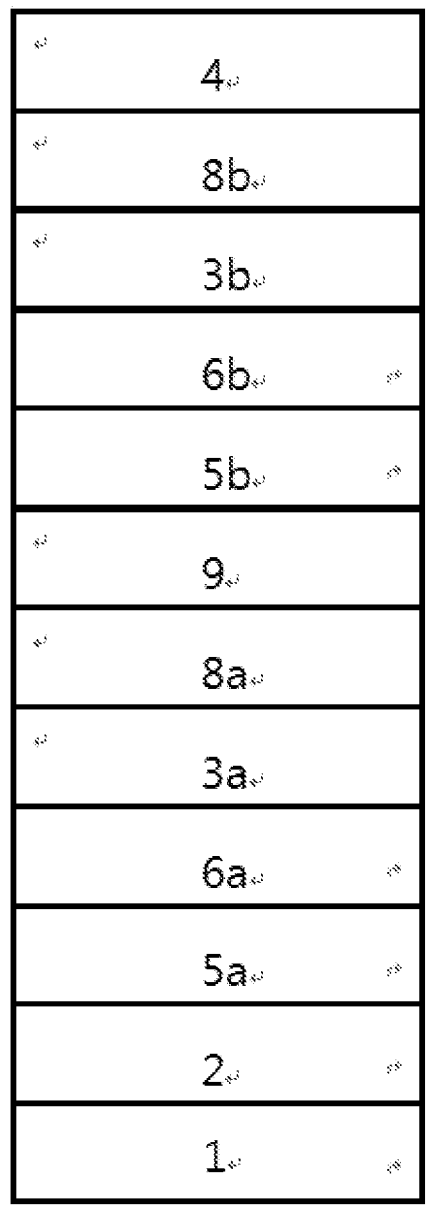

HETEROCYCLIC COMPOUND AND ORGANIC LIGHT EMITTING DEVICE COMPRISING THE SAME

CROSS-REFERENCE TO RELATED APPLICATIONS

The present application is a national phase entry under 35 U.S.C. § 371 of International Application No. PCT/KR2016/012078, filed Oct. 26, 2016, which claims priority to and the benefit of Korean Patent Application No. 10-2015-0148680, filed in the Korean Intellectual Property Office on Oct. 26, 2015, the disclosures of which are incorporated herein by reference.

TECHNICAL FIELD

The present specification relates to a heterocyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Korean Patent Application Laid-Open No. 2013-0007441

DETAILED DESCRIPTION OF THE INVENTION

Technical Problem

The present specification describes a heterocyclic compound and an organic light emitting device including the same.

Technical Solution

An exemplary embodiment of the present specification provides a compound represented by the following Chemical Formula 1:

[Chemical Formula 1]

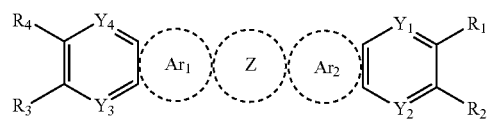

in Chemical Formula 1,

Z is a substituted or unsubstituted thiophene ring; or a substituted or unsubstituted thienothiophene ring, $Ar_1$ is

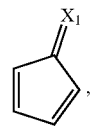

$Ar_2$ is

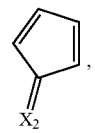

$X_1$ and $X_2$ are the same as or different from each other, and are each independently any one selected from the following (a) to (g),

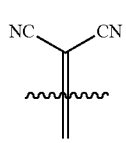
(a)

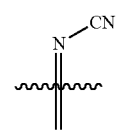
(b)

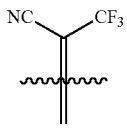
(c)

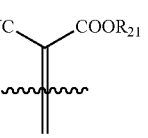
(d)

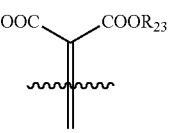
(e)

-continued

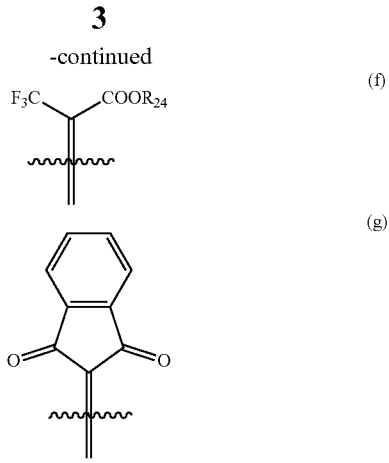

Y₁ to Y₄ are the same as or different from each other, and are each independently N; CH; or CR₅, R₁ to R₅ are the same as or different from each other, and are each independently hydrogen; deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; a substituted or unsubstituted silyl group; or a substituted or unsubstituted heterocyclic group, or adjacent groups of R₁ to R₅ combine with each other to form a substituted or unsubstituted aromatic hydrocarbon ring or a substituted or unsubstituted hetero ring, when Z is a substituted or unsubstituted thiophene ring, all of Y1 to Y4 are CH, and X₁ and X₂ are the same as or different from each other and are each any one of (a) to (f), at least one of R₁ to R₅ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; a substituted or unsubstituted silyl group; or a substituted or unsubstituted heterocyclic group, or adjacent groups of R₁ to R₅ combine with each other to form a substituted or unsubstituted aromatic hydrocarbon ring or a substituted or unsubstituted hetero ring, and R₂₁ to R₂₄ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heterocyclic group.

Further, an exemplary embodiment of the present specification provides an organic light emitting device including a first electrode, a second electrode, and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material which carries out hole injection, hole transport, hole buffer, charge generation, or both hole injection and hole transport.

BRIEF DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transport layer 6, a light emitting layer 3, an electron transport layer 7, and a negative electrode 4.

FIG. 3 illustrates an example of an organic light emitting device including a substrate 1, a positive electrode 2, and a negative electrode 4, and including two units including hole injection layers 5a and 5b, hole transport layers 6a and 6b, light emitting layers 3a and 3b, and charge transport layers 8a and 8b between the positive electrode and the negative electrode, in which a charge generation layer 9 is provided between the units.

BEST MODE

Hereinafter, the present specification will be described in more detail.

An exemplary embodiment of the present specification provides the compound represented by Chemical Formula 1.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other. As another example, when any one or more of Y₁ to Y₄ in Chemical Formula 1 is CR₅, R₅ may be interpreted as a group which is "adjacent" to a sterically close substituent in $R_1$ to $R_4$. Further, in Chemical Formula 1, R1 and R2 or R3 and R4 may be interpreted as a group which is "adjacent" to each other.

In the present specification, examples of a halogen group include fluorine, chlorine, bromine or iodine. In the present specification, the number of carbon atoms of a carbonyl group is not particularly limited, but is preferably 1 to 40. Specifically, the carbonyl group may be a compound having the following structures, but is not limited thereto.

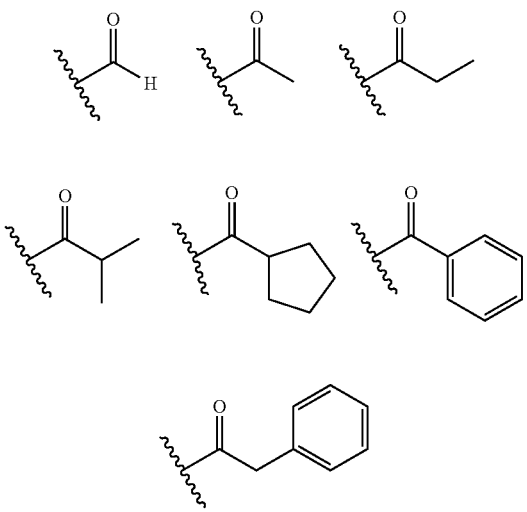

In the present specification, for an ester group, the oxygen of the ester group may be substituted with a straight-chained, branch-chained, or cyclic alkyl group having 1 to 40 carbon atoms, or an aryl group having 6 to 30 carbon atoms. Specifically, the ester group may be a compound having the following structural formulae, but is not limited thereto.

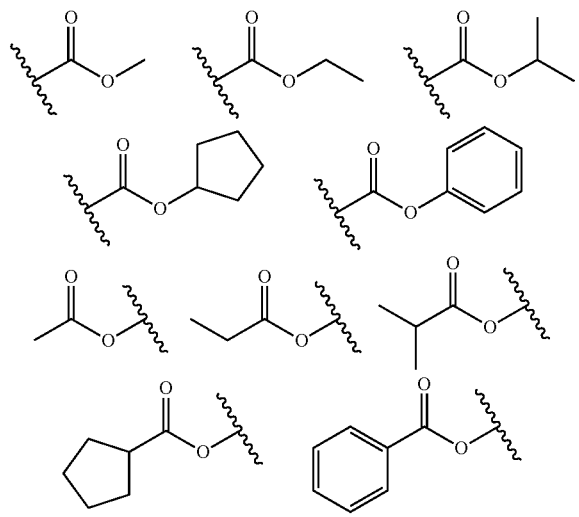

In the present specification, the number of carbon atoms of an imide group is not particularly limited, but is preferably 1 to 25. Specifically, the imide group may be a compound having the following structures, but is not limited thereto.

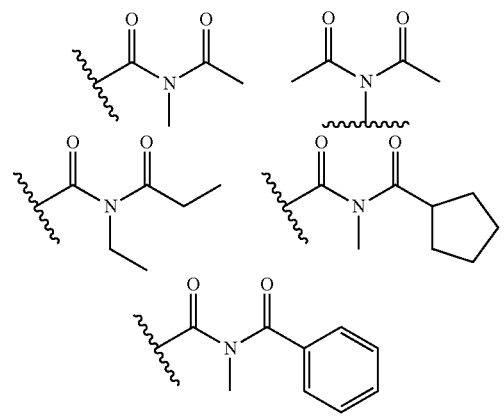

In the present specification, a silyl group may be represented by a chemical formula of —$SiR_aR_bR_c$, and $R_a$, $R_b$, and $R_c$ may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of —$BR_aR_bR_c$, and $R_a$, $R_b$, and $R_c$ may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkoxy group may be straight-chained, branch-chained, or cyclic. The number of carbon atoms of the alkoxy group is not particularly limited, but is preferably 1 to 40. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

A substituent including an alkyl group, an alkoxy group, and other alkyl group moieties described in the present specification includes both a straight-chained form and a branch-chained form.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. According to still yet another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the number of carbon atoms of an alkylamine group is not particularly limited, but is preferably 1 to 40. Specific examples of the alkylamine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include a monocyclic heterocyclic group, a polycyclic heterocyclic group, or both a monocyclic heterocyclic group and a polycyclic heterocyclic group. In the present specification, an arylheteroarylamine group means an amine group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the fluorenyl group may be a spiro fluorenyl group such as

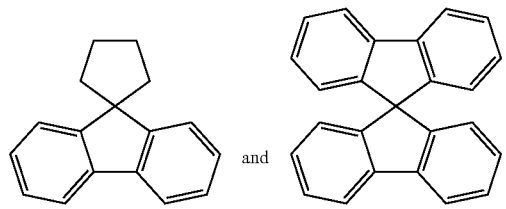

and and a substituted fluorenyl group such as

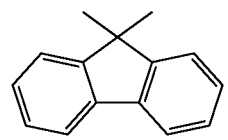

(a 9,9-dimethylfluorenyl group) and

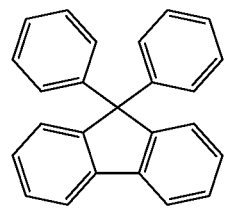 [SMILES: c1ccc(C2(c3ccccc3)c3ccccc3-c3ccccc32)cc1]

(a 9,9-diphenylfluorenyl group). However, the fluorenyl group is not limited thereto.

In the present specification, a heterocyclic group is a heterocyclic group including one or more of N, O, P, S, Si, and Se as a hetero atom, and the number of carbon atoms thereof is not particularly limited, but is preferably 1 to 60. According to an exemplary embodiment, the number of carbon atoms of the heterocyclic group is 1 to 30. Examples of the heterocyclic group include a pyridyl group, a pyrrole group, a pyrimidyl group, a pyridazinyl group, a furanyl group, a thiophenyl group, an imidazole group, a pyrazole group, an oxazole group, an isooxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acrydyl group, a xanthenyl group, a phenanthridinyl group, a diaza naphthalenyl group, a triazaindenyl group, an indole group, an indolinyl group, an indolizinyl group, a phthalizinyl group, a pyrido pyrimidinyl group, a pyrido pyrazinyl group, a pyrazino pyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzoimidazoquinazoline group, or a benzoimidazophenanthridine group, and the like, but are not limited thereto.

In the present specification, the above-described description on the heterocyclic group may be applied to a heteroaryl group except for an aromatic group.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the above-described description on the alkyl group may be applied to an alkyl group in an alkylthioxy group, an alkylsulfoxy group, an aralkyl group, an aralkylamine group, an alkylaryl group, and an alkylamine group.

In the present specification, the above-described description on the heterocyclic group may be applied to a heteroaryl group in a heteroaryl group, a heteroarylamine group, and an arylheteroarylamine group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a condensed ring thereof.

In the present specification, an aliphatic hydrocarbon ring means a ring composed only of carbon and hydrogen atoms as a ring which is not an aromatic group. Specifically, examples of the aliphatic hydrocarbon ring include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene, and the like, but are not limited thereto.

In the present specification, an aromatic hydrocarbon ring means an aromatic ring composed only of carbon and hydrogen atoms. Specifically, examples of the aromatic hydrocarbon ring include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene, and the like, but are not limited thereto.

In the present specification, an aliphatic hetero ring means an aliphatic ring including one or more of hetero atoms. Specifically, examples of the aliphatic hetero ring include oxirane, tetrahydrofuran, 1,4-dioxane, pyrrolidine, piperidine, morpholine, oxepane, azocane, thiocane, and the like, but are not limited thereto. In the present specification, an aromatic hetero ring means an aromatic ring including one or more of hetero atoms. Specifically, examples of the aromatic hetero ring include pyridine, pyrrole, pyrimidine, pyridazine, furan, thiophene, imidazole, pyrazole, oxazole, isooxazole, triazole, isothiazole, triazole, oxadiazole, thiadiazole, dithiazole, tetrazole, pyran, thiopyran, diazine, oxazine, triazine, dioxine, triazine, tetrazine, isoquinoline, quinoline, quinol, quinazoline, quinoxaline, naphthyridine, acridine, phenanthridine, diaza naphthalene, triazaindene, indole, indolizine, benzothiazole, benzoxazole, benzoimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole, and the like, but are not limited thereto.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, the compound of Chemical Formula 1 may be represented by any one of the following Chemical Formulae 2 to 4.

[Chemical Formula 2]

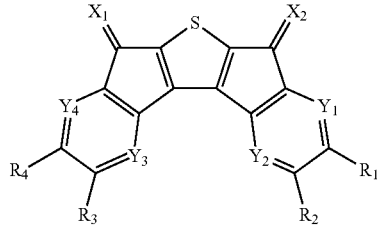

[Chemical Formula 3]

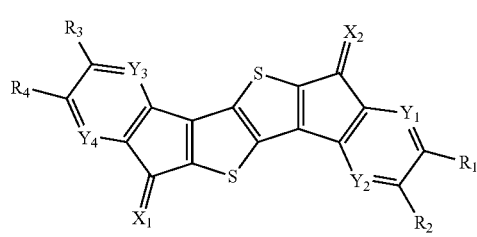

[Chemical Formula 4]

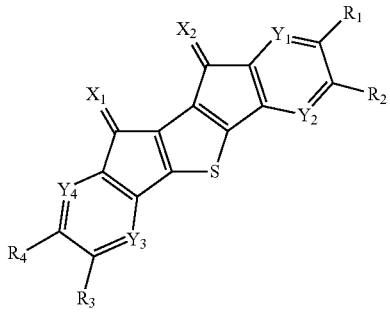

In Chemical Formulae 2 to 4, definitions of $X_1$, $X_2$, $Y_1$ to $Y_4$, $R_1$ to $R_5$, and $R_{21}$ to $R_{24}$ are the same as those in Chemical Formula 1.

In an exemplary embodiment of the present invention, $Y_1$ to $Y_4$ are the same as or different from each other, and are each independently N; CH; or $CR_5$.

In an exemplary embodiment, one of $Y_1$ to $Y_4$ is N.

In an exemplary embodiment, $Y_1$ is N.

In an exemplary embodiment, $Y_2$ is N.

In an exemplary embodiment, $Y_3$ is N.

In an exemplary embodiment, $Y_4$ is N.

In an exemplary embodiment, two of $Y_1$ to $Y_4$ are N.

In an exemplary embodiment, $Y_1$ and $Y_2$ are N.

In an exemplary embodiment, $Y_2$ and $Y_3$ are N.

In an exemplary embodiment, $Y_2$ and $Y_3$ are N, and $Y_1$ and $Y_4$ are CH.

In an exemplary embodiment, $Y_1$ and $Y_3$ are N.

In an exemplary embodiment, $Y_1$ and $Y_4$ are N.

In an exemplary embodiment, $Y_2$ and $Y_4$ are N.

In an exemplary embodiment, $Y_3$ and $Y_4$ are N.

In an exemplary embodiment, three of $Y_1$ to $Y_4$ are N.

In an exemplary embodiment, $Y_1$ to $Y_4$ are N.

In an exemplary embodiment of the present invention, the compound of Chemical Formula 1 may be represented by any one of the following Chemical Formulae 5 to 8.

[Chemical Formula 5]

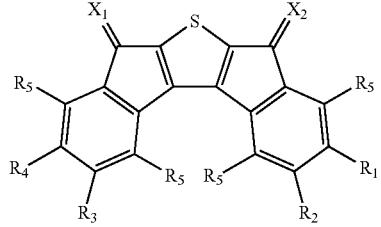

[Chemical Formula 6]

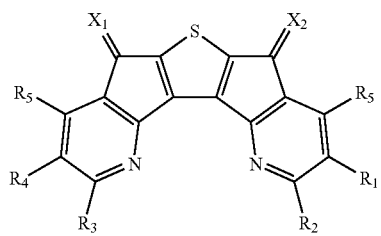

[Chemical Formula 7]

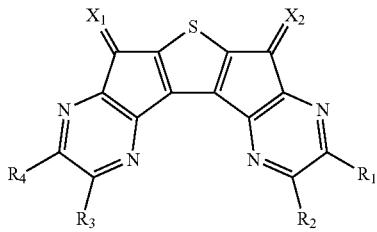

[Chemical Formula 8]

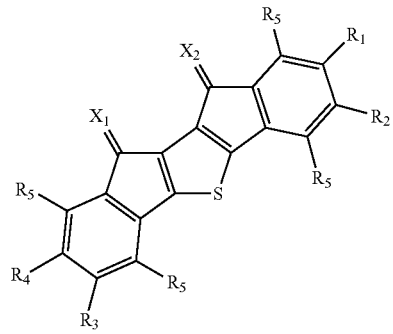

In Chemical Formulae 5 to 8, definitions of $X_1$, $X_2$, $Y_1$ to $Y_4$, $R_1$ to $R_5$, and $R_{21}$ to $R_{24}$ are the same as those in Chemical Formula 1.

In an exemplary embodiment, at least one of $R_1$ to $R_4$ in Chemical Formula 5 is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups combine with each other to form a substituted or unsubstituted aromatic hydrocarbon ring or a substituted or unsubstituted hetero ring.

In an exemplary embodiment of the present invention, the compound of Chemical Formula 1 may be represented by any one of the following Chemical Formulae 9 to 11.

[Chemical Formula 9]

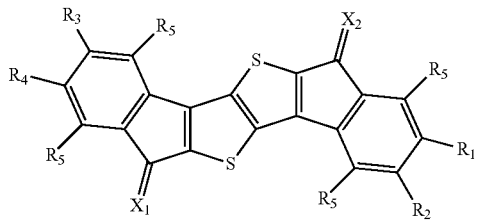

[Chemical Formula 10]

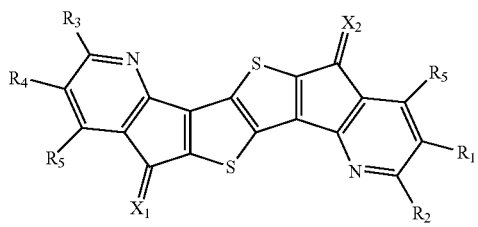

-continued

[Chemical Formula 11]

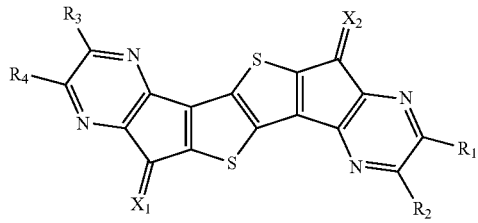

In Chemical Formulae 9 to 11,
definitions of $X_1$, $X_2$, $Y_1$ to $Y_4$, $R_1$ to $R_5$, and $R_{21}$ to $R_{24}$ are the same as those in Chemical Formula 1.

In an exemplary embodiment of the present invention, $R_1$ to $R_5$ are the same as or different from each other, and are each independently hydrogen; deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring.

In an exemplary embodiment of the present invention, $R_1$ to $R_5$ are the same as or different from each other, and are each independently hydrogen; deuterium; a fluoro group; a nitrile group; an alkyl group which is unsubstituted or substituted with one or more substituents selected from the group consisting of deuterium, a fluoro group, and a nitrile group; an alkoxy group which is unsubstituted or substituted with one or more substituents selected from the group consisting of deuterium, a fluoro group, a nitrile group, and a fluoroalkyl group; an aryl group which is unsubstituted or substituted with one or more substituents selected from the group consisting of deuterium, a fluoro group, a nitrile group, a fluoroalkyl group, and a fluoroalkoxy group; or a heterocyclic group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form an aromatic hydrocarbon ring which is unsubstituted or substituted with one or more substituents selected from the group consisting of deuterium, a fluoro group, a nitrile group, a fluoroalkyl group, and a fluoroalkoxy group or a hetero ring which is unsubstituted or substituted with one or more substituents selected from the group consisting of deuterium, a fluoro group, a nitrile group, a fluoroalkyl group, and a fluoroalkoxy group.

In an exemplary embodiment of the present invention, $R_1$ to $R_5$ are the same as or different from each other, and are each independently hydrogen; deuterium; a fluoro group; a nitrile group; a fluoromethyl group; a fluoroethyl group; a fluoropropyl group; a fluoromethoxy group; a fluoroethoxy group; a fluoropropoxy group; a phenyl group which is unsubstituted or substituted with one or more substituents selected from the group consisting of deuterium, a fluoro group, a nitrile group, a fluoroalkyl group, and a fluoroalkoxy group; a naphthyl group which is unsubstituted or substituted with one or more substituents selected from the group consisting of deuterium, a fluoro group, a nitrile group, a fluoroalkyl group, and a fluoroalkoxy group; or a thiophene group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form a benzene ring which is unsubstituted or substituted with one or more substituents selected from the group consisting of deuterium, a fluoro group, a nitrile group, a fluoroalkyl group, and a fluoroalkoxy group; or a pyridine ring which is unsubstituted or substituted with one or more substituents selected from the group consisting of deuterium, a fluoro group, a nitrile group, a fluoroalkyl group, and a fluoroalkoxy group.

In an exemplary embodiment, when adjacent groups of $R_1$ to $R_5$ combine with each other to form a substituted or unsubstituted aromatic hydrocarbon ring or a substituted or unsubstituted hetero ring, the ring is a benzene ring or a pyridine ring.

In the present invention, when Z is a substituted or unsubstituted thiophene ring, all of Y1 to Y4 are CH, and $X_1$ and $X_2$ are the same as or different from each other and are each any one of (a) to (f), at least one of $R_1$ to $R_5$ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring.

In an exemplary embodiment, when Z is a substituted or unsubstituted thiophene ring, all of Y1 to Y4 are CH, and $X_1$ and $X_2$ are the same as or different from each other and are each any one of (a) to (f), at least one of $R_1$ to $R_5$ is deuterium; a fluoro group; a nitrile group; a fluoromethyl group; a fluoroethyl group; a fluoropropyl group; a fluoromethoxy group; a fluoroethoxy group; a fluoropropoxy group; a phenyl group which is unsubstituted or substituted with one or more substituents selected from the group consisting of deuterium, a fluoro group, a nitrile group, a fluoroalkyl group, and a fluoroalkoxy group; a naphthyl group which is unsubstituted or substituted with one or more substituents selected from the group consisting of deuterium, a fluoro group, a nitrile group, a fluoroalkyl group, and a fluoroalkoxy group; or a thiophene group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form a benzene ring which is unsubstituted or substituted with one or more substituents selected from the group consisting of deuterium, a fluoro group, a nitrile group, a fluoroalkyl group, and a fluoroalkoxy group; or a pyridine ring which is unsubstituted or substituted with one or more substituents selected from the group consisting of deuterium, a fluoro group, a nitrile group, a fluoroalkyl group, and a fluoroalkoxy group.

In another exemplary embodiment, when Z is a substituted or unsubstituted thiophene ring, and all of Y1 to Y4 are CH, at least one of $R_1$ to $R_5$ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring.

In an exemplary embodiment, when Z is a substituted or unsubstituted thiophene ring, and all of Y1 to Y4 are CH, at least one of $R_1$ to $R_5$ is deuterium; a fluoro group; a nitrile group; a fluoromethyl group; a fluoroethyl group; a fluoropropyl group; a fluoromethoxy group; a fluoroethoxy group; a fluoropropoxy group; a phenyl group which is unsubstituted or substituted with one or more substituents selected from the group consisting of deuterium, a fluoro group, a nitrile group, a fluoroalkyl group, and a fluoroalkoxy group; a naphthyl group which is unsubstituted or substituted with one or more substituents selected from the group consisting of deuterium, a fluoro group, a nitrile group, a fluoroalkyl group, and a fluoroalkoxy group; or a thiophene group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form a benzene ring which is unsubstituted or substituted with one or more substituents selected from the group consisting of deuterium, a fluoro group, a nitrile group, a fluoroalkyl group, and a fluoroalkoxy group; or a pyridine ring which is unsubstituted or substituted with one or more substituents selected from the group consisting of deuterium, a fluoro group, a nitrile group, a fluoroalkyl group, and a fluoroalkoxy group.

In another exemplary embodiment, when Z is a substituted or unsubstituted thiophene ring, at least one of $R_1$ to $R_5$ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring.

In an exemplary embodiment, when Z is a substituted or unsubstituted thiophene ring, at least one of $R_1$ to $R_5$ is deuterium; a fluoro group; a nitrile group; a fluoromethyl group; a fluoroethyl group; a fluoropropyl group; a fluoromethoxy group; a fluoroethoxy group; a fluoropropoxy group; a phenyl group which is unsubstituted or substituted with one or more substituents selected from the group consisting of deuterium, a fluoro group, a nitrile group, a fluoroalkyl group, and a fluoroalkoxy group; a naphthyl group which is unsubstituted or substituted with one or more substituents selected from the group consisting of deuterium, a fluoro group, a nitrile group, a fluoroalkyl group, and a fluoroalkoxy group; or a thiophene group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form a benzene ring which is unsubstituted or substituted with one or more substituents selected from the group consisting of deuterium, a fluoro group, a nitrile group, a fluoroalkyl group, and a fluoroalkoxy group; or a pyridine ring which is unsubstituted or substituted with one or more substituents selected from the group consisting of deuterium, a fluoro group, a nitrile group, a fluoroalkyl group, and a fluoroalkoxy group.

In another exemplary embodiment, when all of $Y_1$ to $Y_4$ are CH, at least one of $R_1$ to $R_5$ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring.

In an exemplary embodiment, when all of $Y_1$ to $Y_4$ are CH, at least one of $R_1$ to $R_5$ is deuterium; a fluoro group; a nitrile group; a fluoromethyl group; a fluoroethyl group; a fluoropropyl group; a fluoromethoxy group; a fluoroethoxy group; a fluoropropoxy group; a phenyl group which is unsubstituted or substituted with one or more substituents selected from the group consisting of deuterium, a fluoro group, a nitrile group, a fluoroalkyl group, and a fluoroalkoxy group; a naphthyl group which is unsubstituted or substituted with one or more substituents selected from the group consisting of deuterium, a fluoro group, a nitrile group, a fluoroalkyl group, and a fluoroalkoxy group; or a thiophene group which is unsubstituted or substituted with one or more substituents selected from the group consisting of deuterium, a fluoro group, a nitrile group, a fluoroalkyl group, and a fluoroalkoxy group, or adjacent groups of $R_1$ to $R_5$ combine with each other to form a benzene ring which is unsubstituted or substituted with one or more substituents selected from the group consisting of deuterium, a fluoro group, a nitrile group, a fluoroalkyl group, and a fluoroalkoxy group; or a pyridine ring which is unsubstituted or substituted with one or more substituents selected from the group consisting of deuterium, a fluoro group, a nitrile group, a fluoroalkyl group, and a fluoroalkoxy group.

In an exemplary embodiment, at least one of $R_1$ to $R_4$ is deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; or a substituted or unsubstituted heterocyclic group.

In an exemplary embodiment of the present invention, the compound of Chemical Formula 1 may be any one selected from the following compounds.

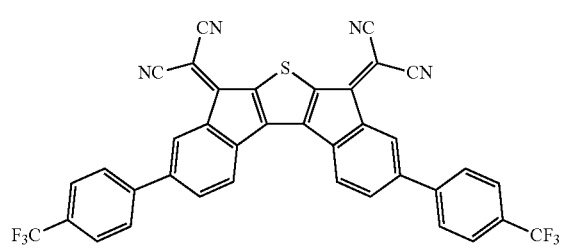

1

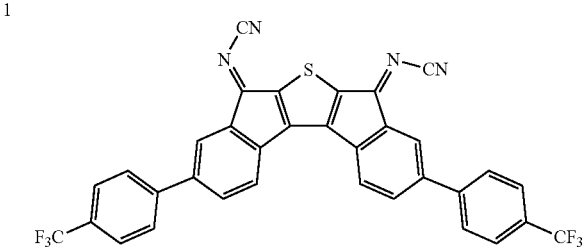

2

-continued
| | |
|---|---|
| 3 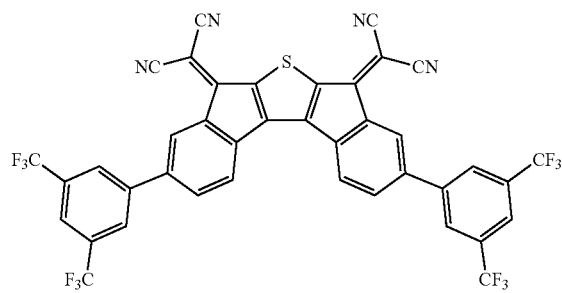 | 4 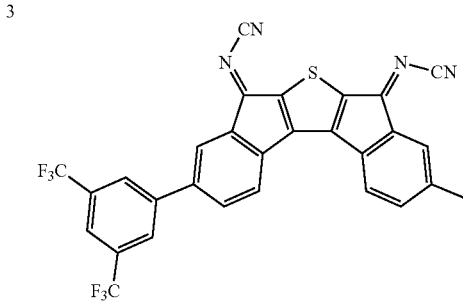 |
| 5 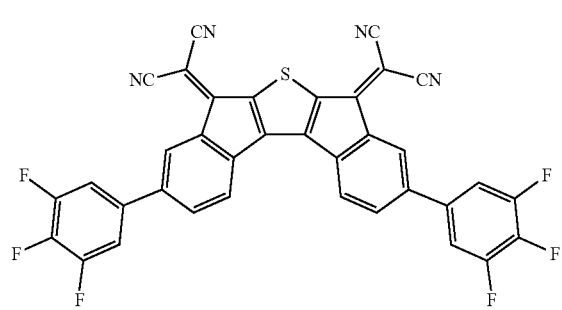 | 6 |
| 7 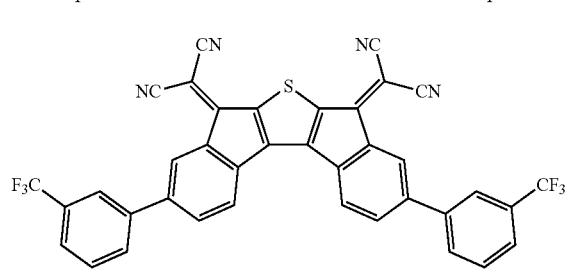 | 8 |
| 9 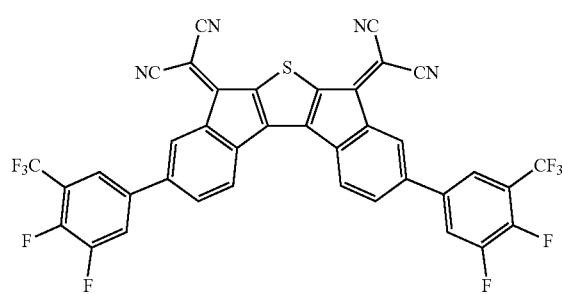 | 10 |
| 11 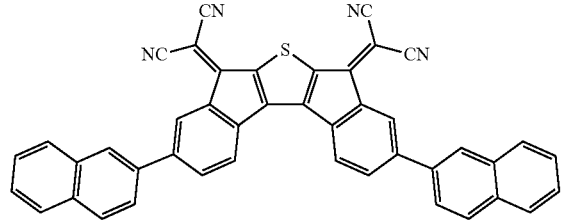 | 12 |
| 13 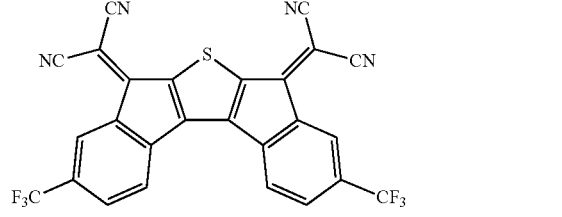 | 14 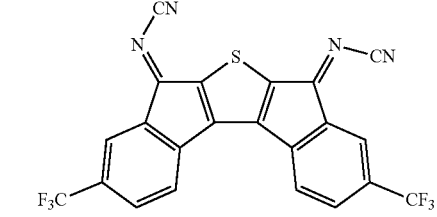 |

-continued
15
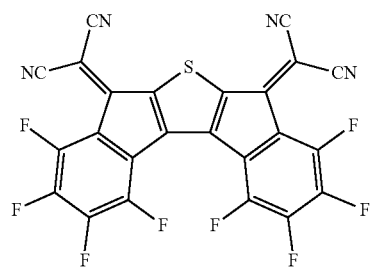
16
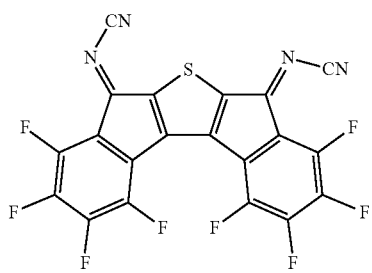
17
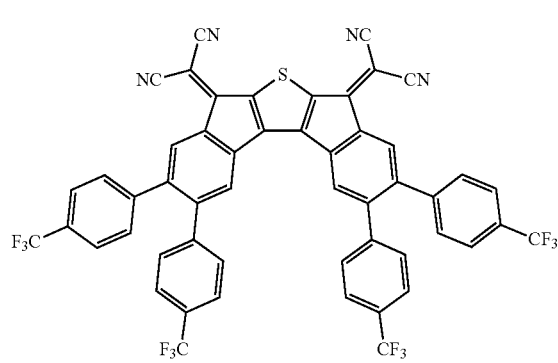
18
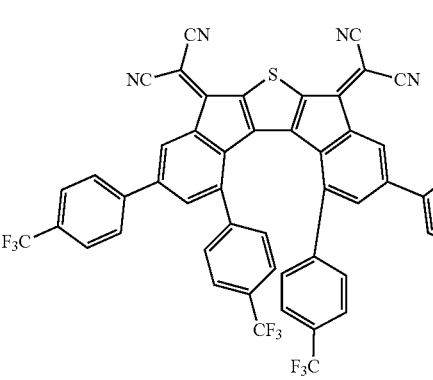
19
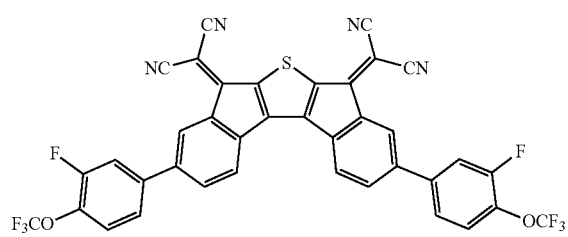
20
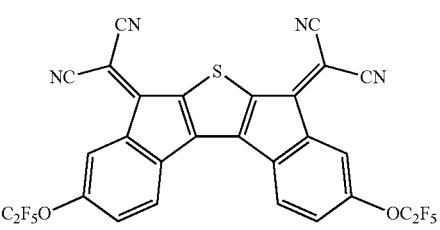
21
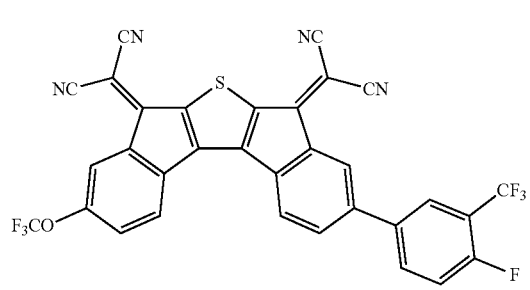
22
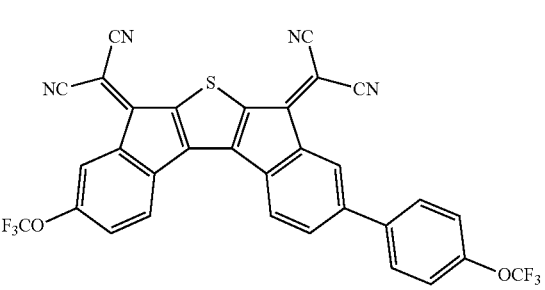
23
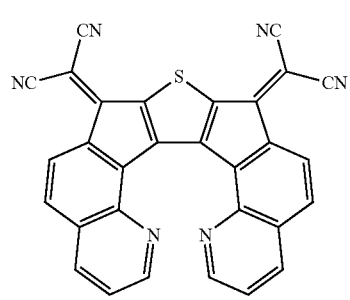
24
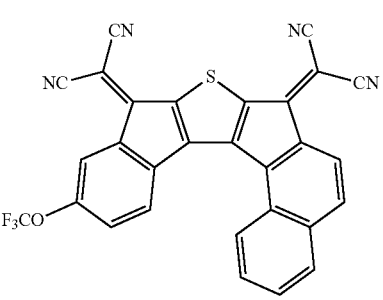

25
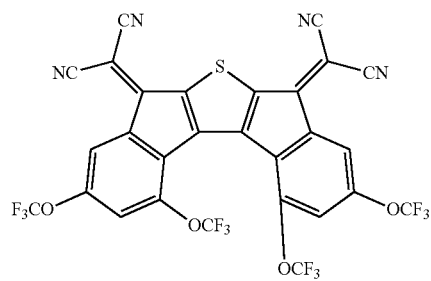
26
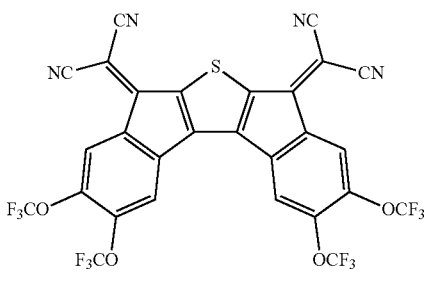
27
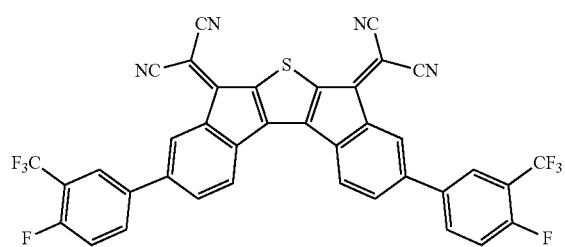
28
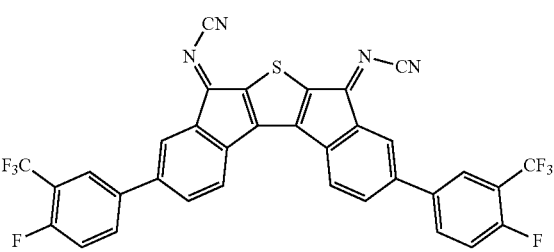
29
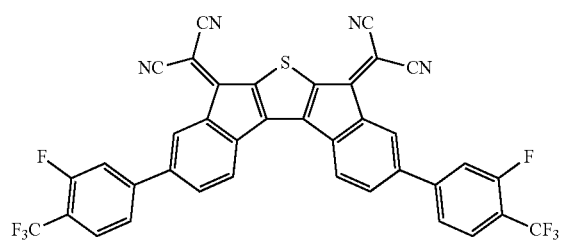
30
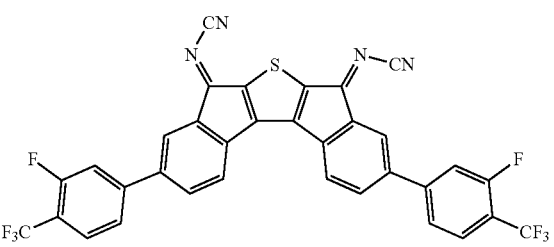
31
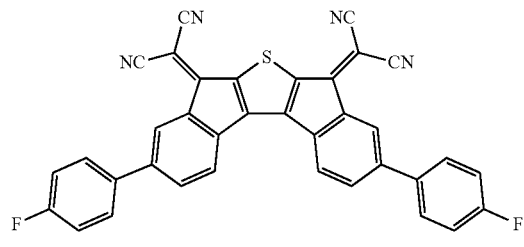
32
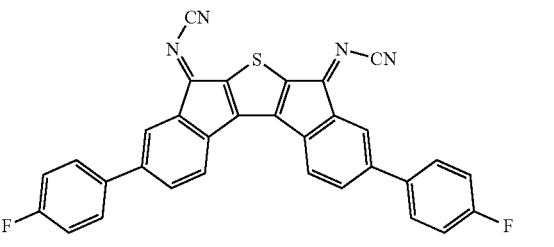
33
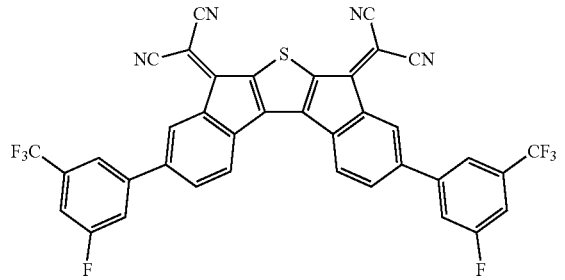
34
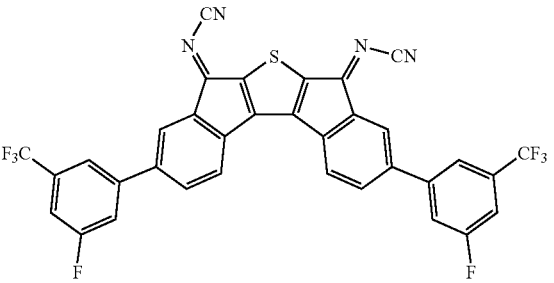
35
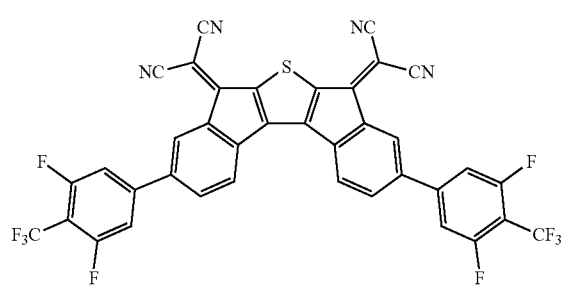
36
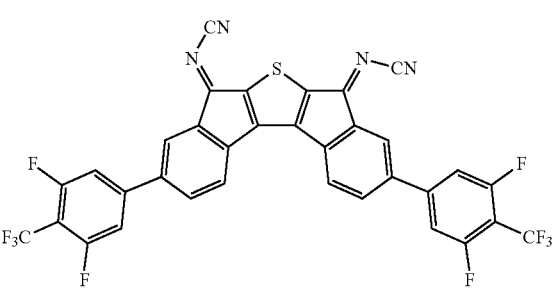

-continued
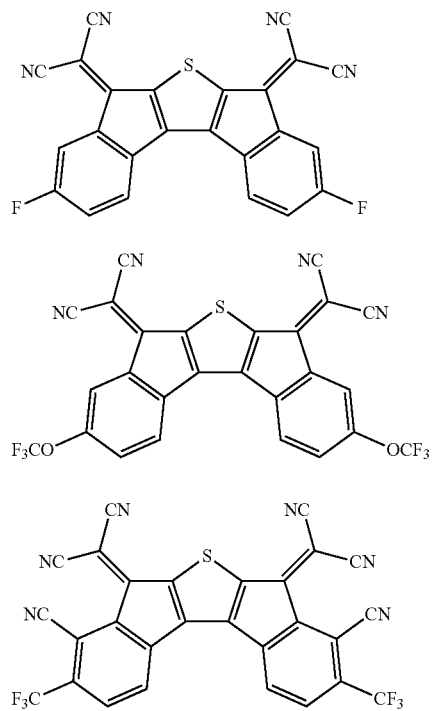
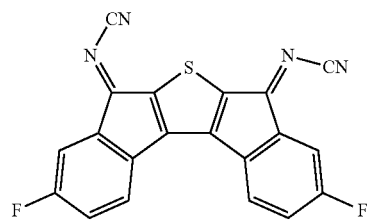
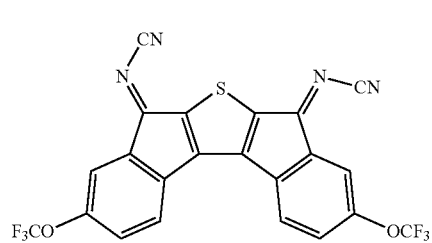
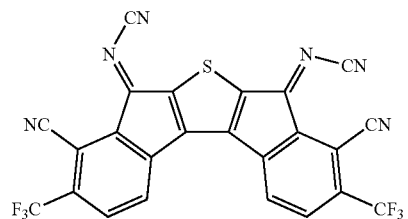
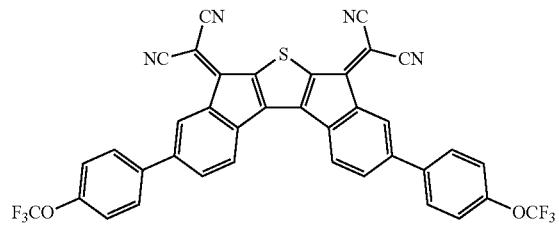
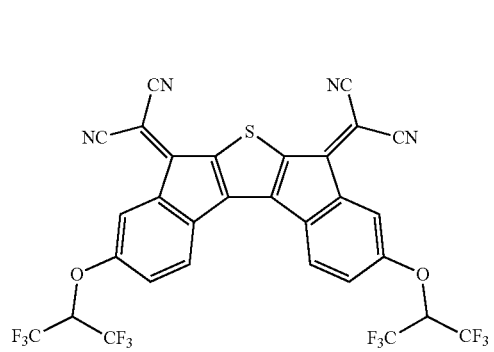
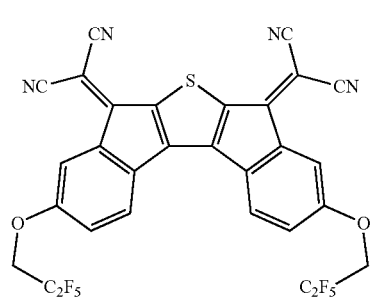
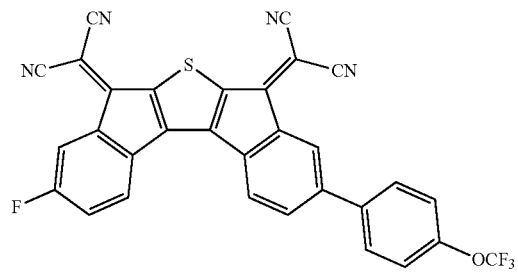
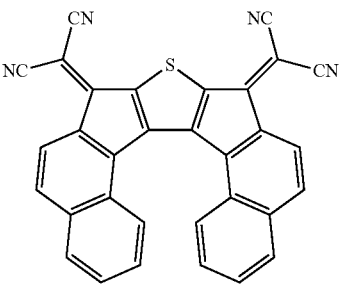

-continued
49
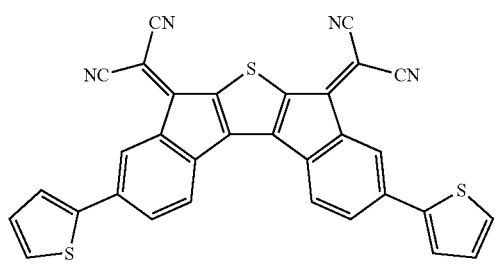
50
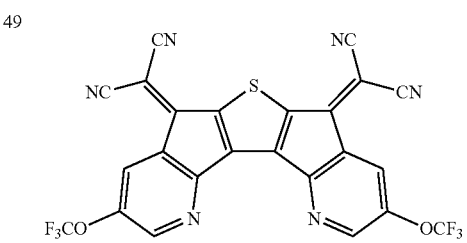
51
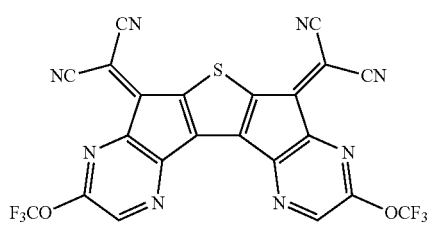
52
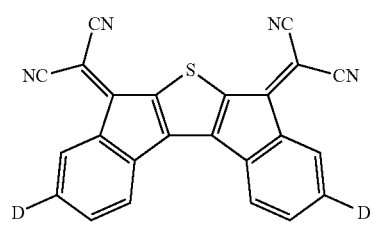
53
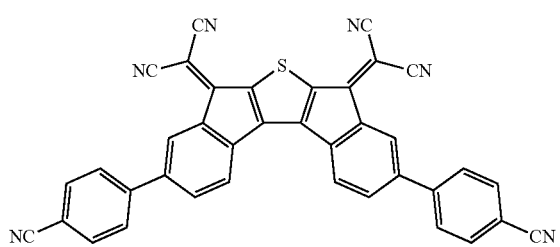
54
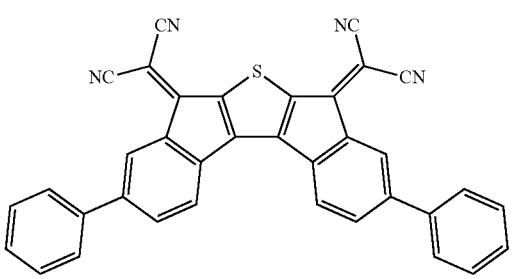
55
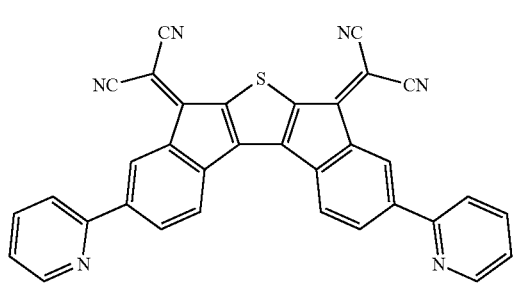
56
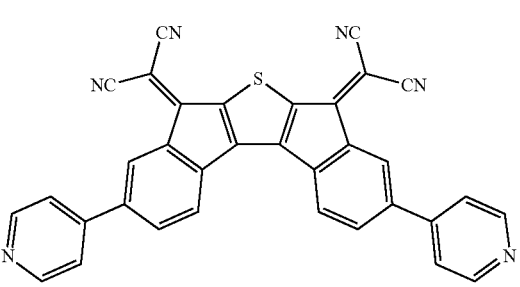
57
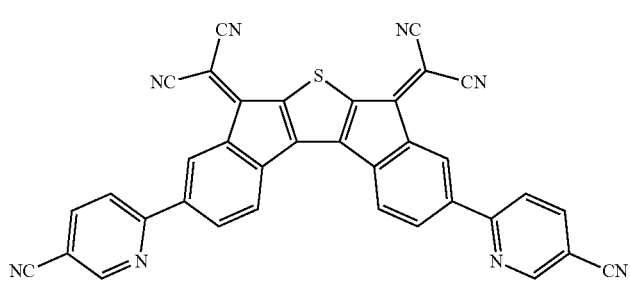
58
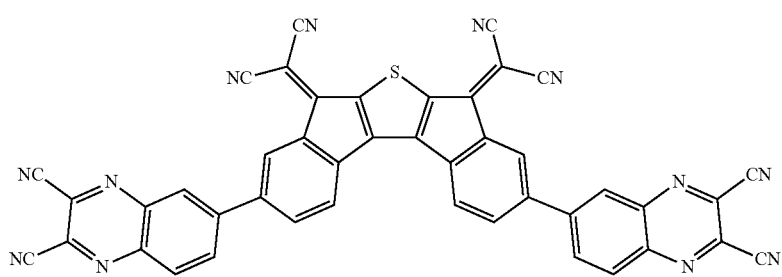

-continued
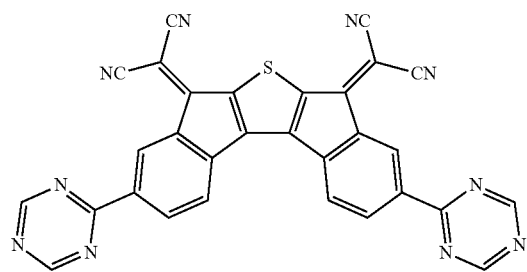
59
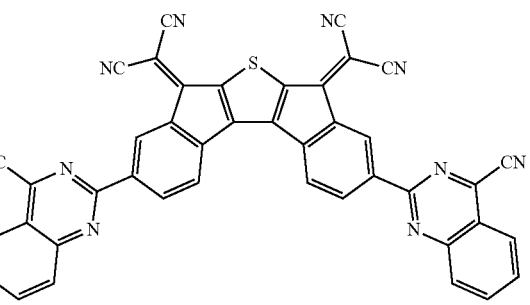
60
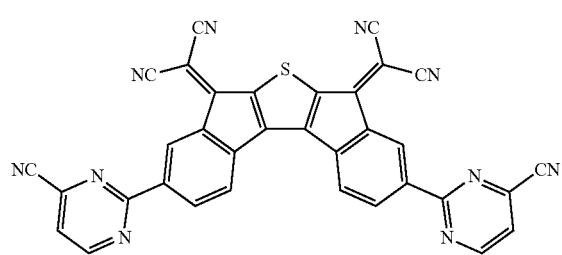
61
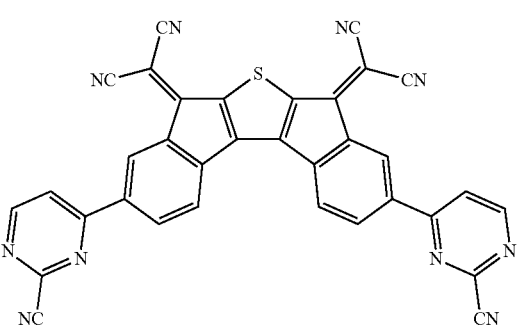
62
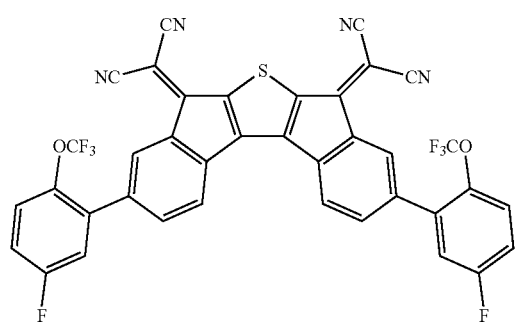
63
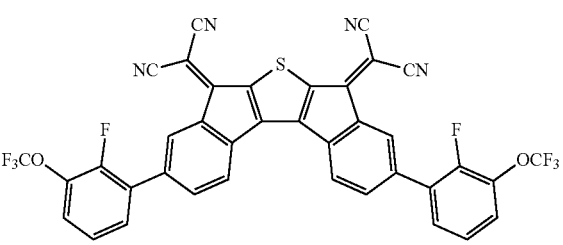
64
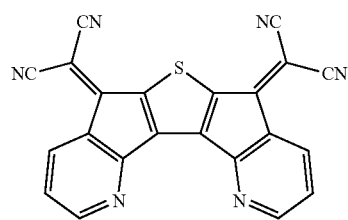
65
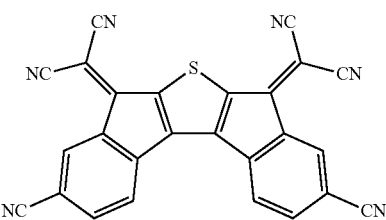
66
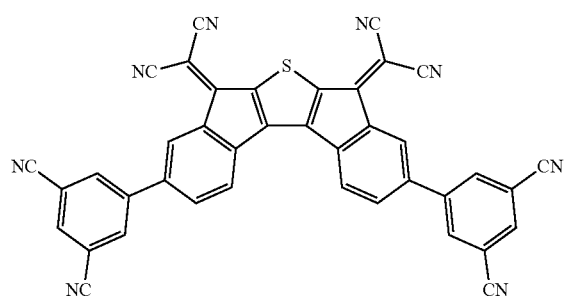
67
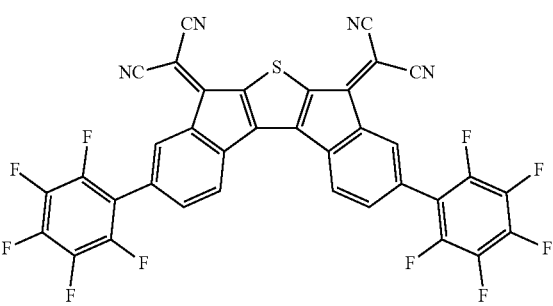
68

-continued
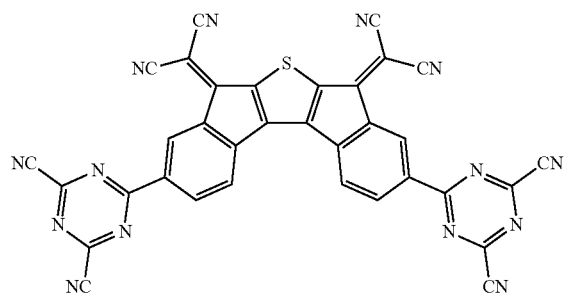
69
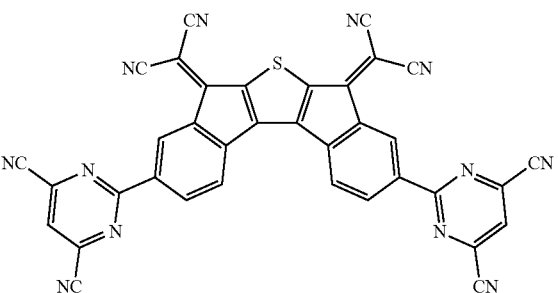
70
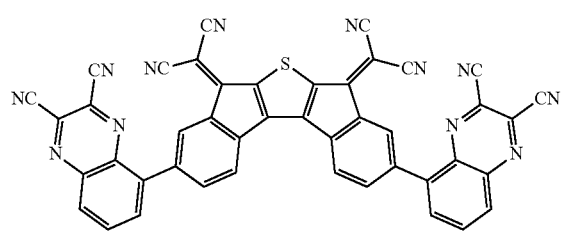
71
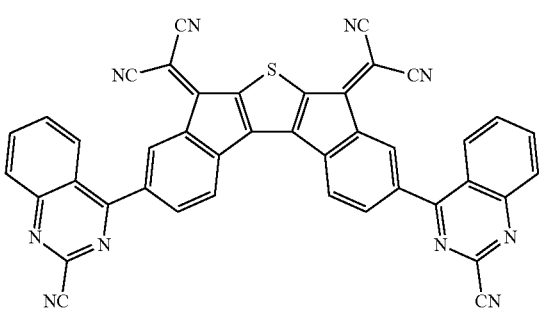
72
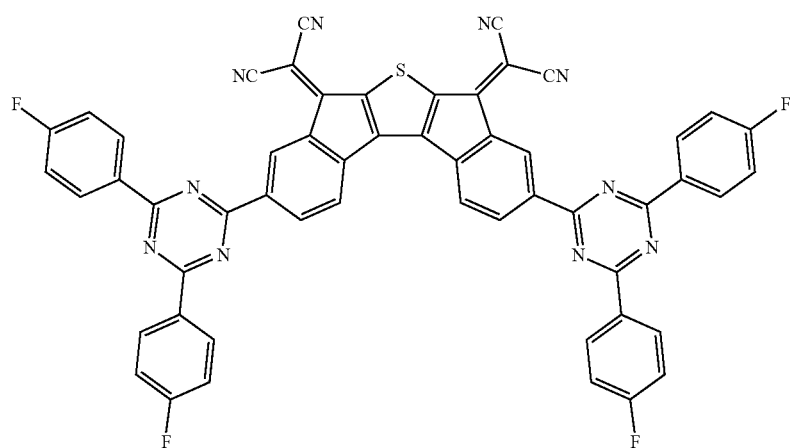
73
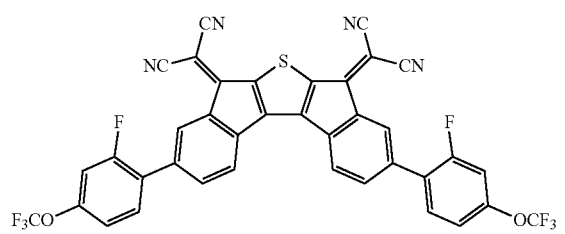
74
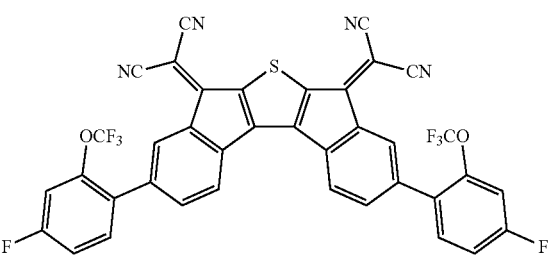
75
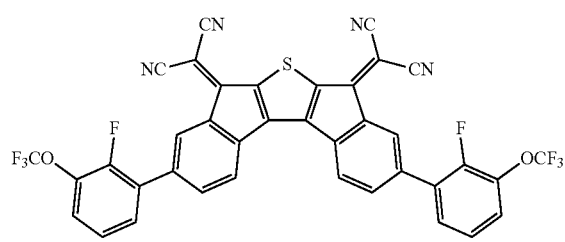
76
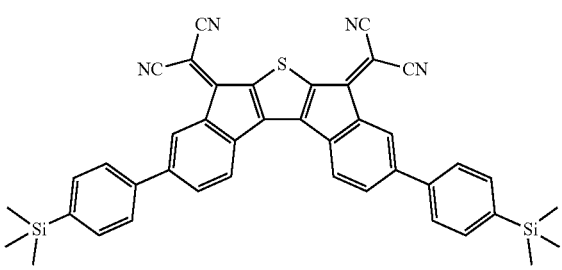
77

-continued
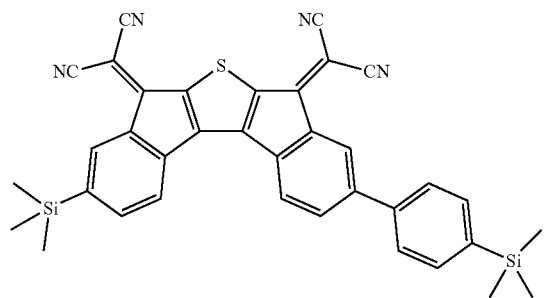
78
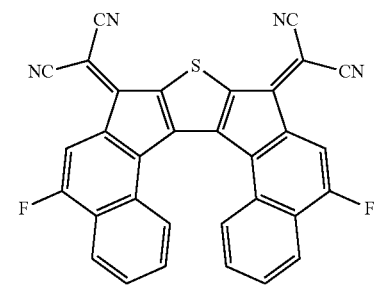
79
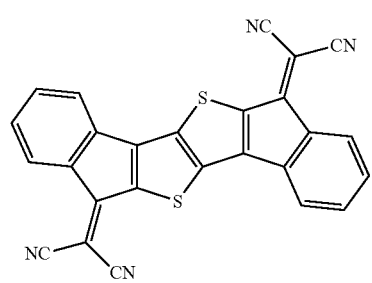
80
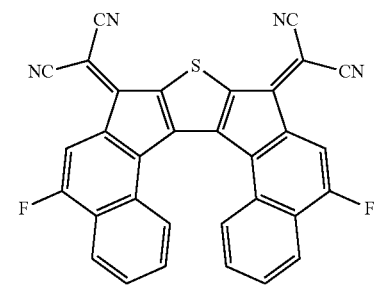
81
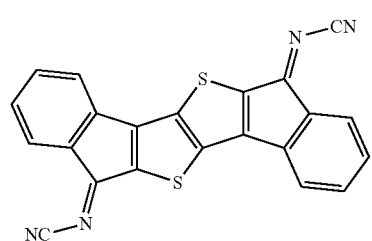
82
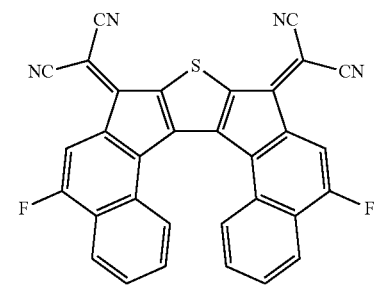
83
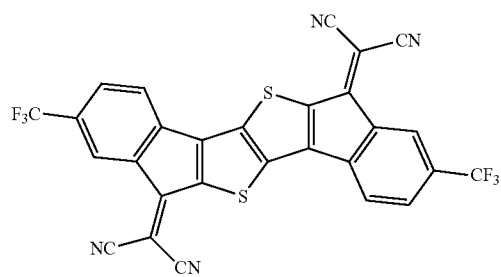
84
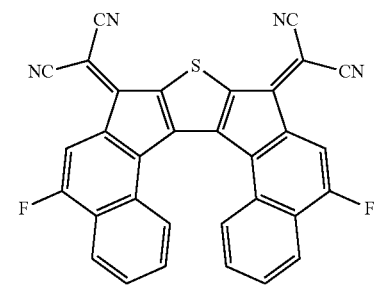
85
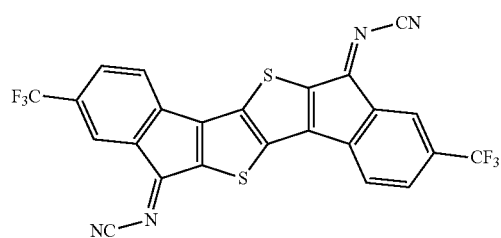
86
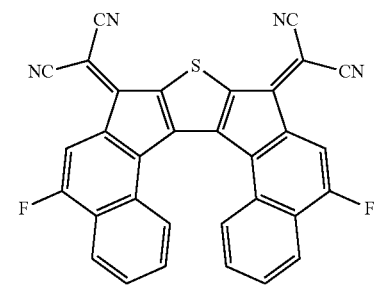
87
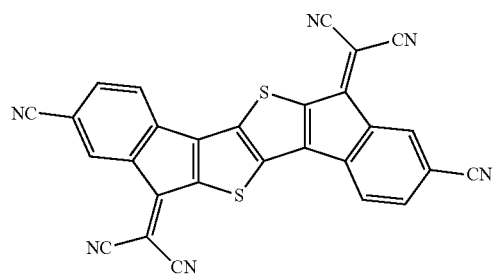
88
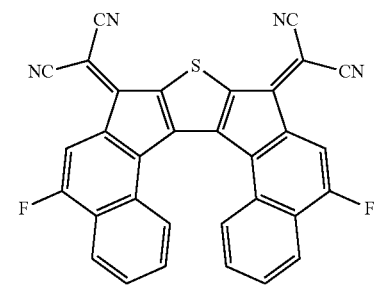
89

-continued
90
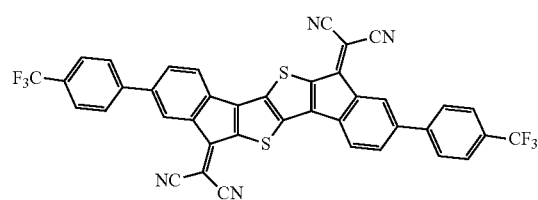
91
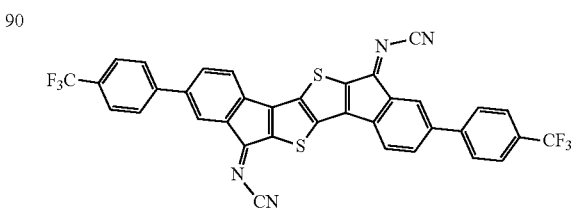
92
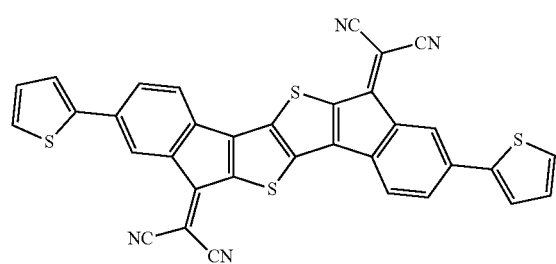
93
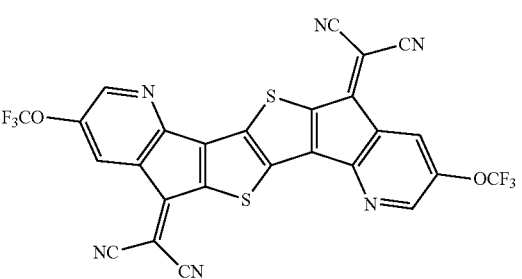
94
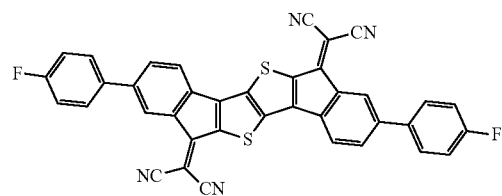
95
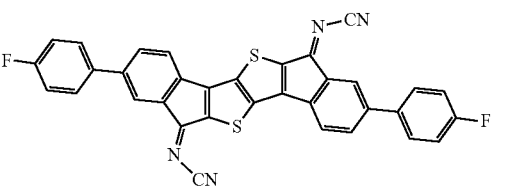
96
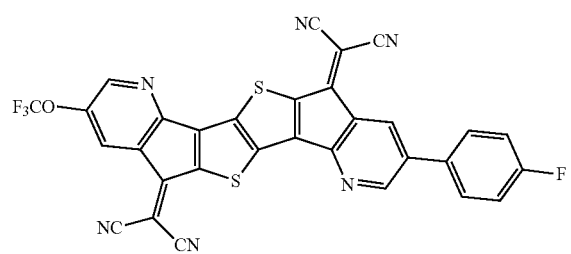
97
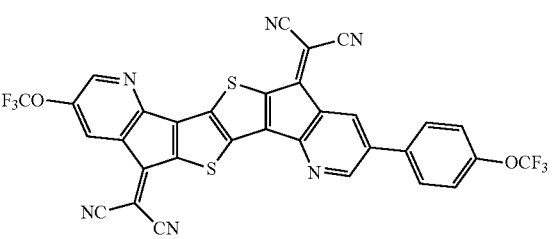
98
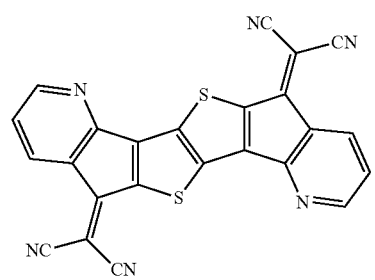
99
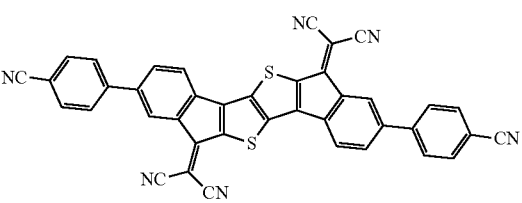
100
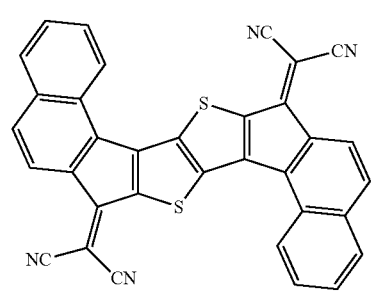
101
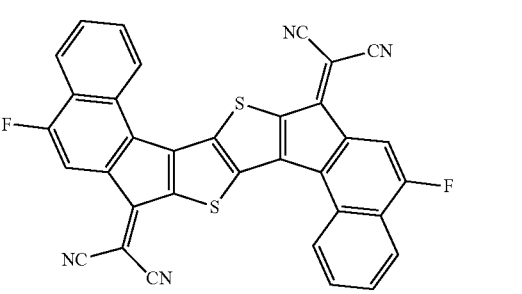

-continued

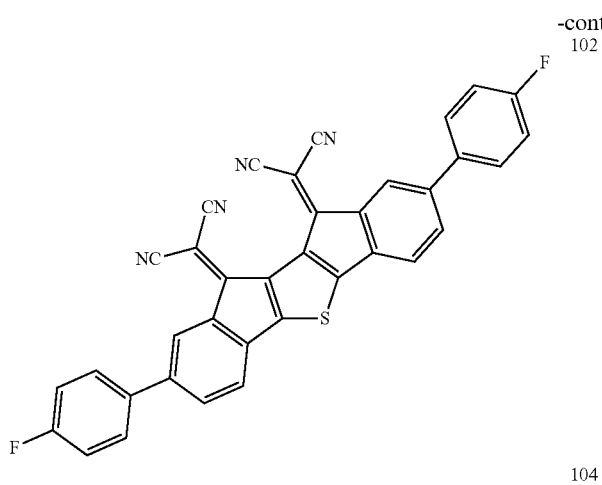

102

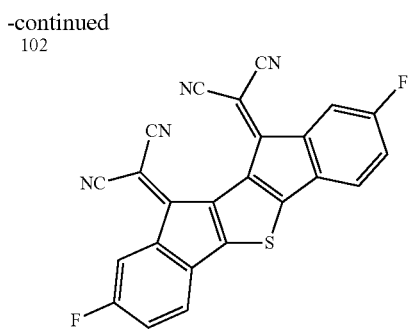

103

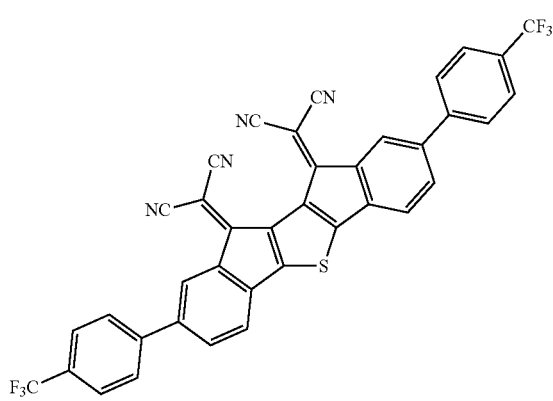

104

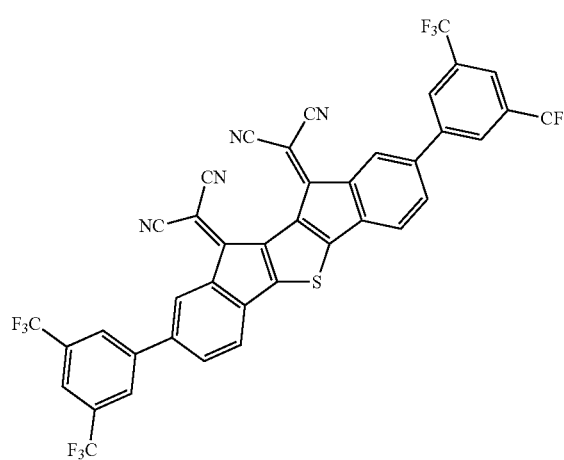

105

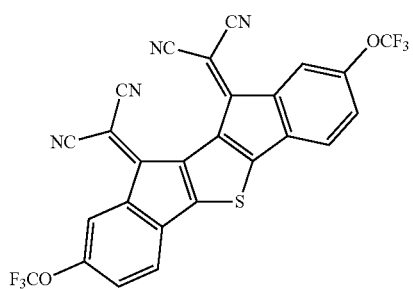

106

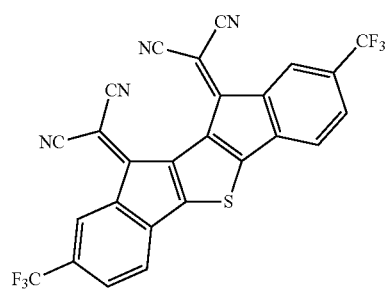

107

A conjugation length and an energy bandgap of a compound are closely associated with each other. Specifically, the longer the conjugation length of the compound is, the smaller the bandgap is. As described above, the core of the compound includes a limited conjugation and thus has a property of a large energy bandgap.

In the present invention, compounds having various energy bandgaps may be synthesized by introducing various substituents into the positions of $Ar_1$, $R_1$ to $R_7$, $R_{1a}$ to $R_{4a}$, R', and R" of a core structure having a large energy bandgap as described above. A substituent is usually introduced into a core structure having a large energy bandgap to easily adjust the energy bandgap, but when the core structure has a small energy bandgap, it is difficult to significantly adjust the energy bandgap by introducing a substituent. Further, in the present invention, various substituents may be introduced into the positions of $Ar_1$, $R_1$ to $R_7$, $R_{1a}$ to $R_{4a}$, R', and R" having the core structure as described above to adjust the HOMO and LUMO energy levels of a compound.

In addition, various substituents may be introduced into the core structure having the structure as described above to synthesize a compound having inherent characteristics of the introduced substituent. For example, a substituent usually used for a hole injection layer material, a material for transporting holes, a material for generating charges, a light emitting layer material, and an electron transport layer material, which are used when manufacturing an organic light emitting device, may be introduced into the core structure to synthesize a material which satisfies conditions required for each organic material layer.

Furthermore, an organic light emitting device according to the present invention is an organic light emitting device including a first electrode, a second electrode, and one or more organic material layers disposed between the first electrode and the second electrode, in which one or more layers of the organic material layers include the compound.

The organic light emitting device of the present invention may be manufactured by typical preparation methods and materials of an organic light emitting device, except that the above-described compound is used to form one or more organic material layers.

The compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

The organic material layer of the organic light emitting device of the present invention may also be composed of a single-layered structure, but may be composed of a multi-layered structure in which two or more organic material layers are stacked. For example, the organic light emitting device of the present invention may have a structure including a hole injection layer, a hole transport layer, a charge generation layer, a light emitting layer, an electron transport layer, an electron injection layer, and the like as organic material layers. However, the structure of the organic light emitting device is not limited thereto, and may include a fewer number of organic material layers.

Accordingly, in the organic light emitting device of the present invention, the organic material layer may include one or more layers of a hole injection layer, a hole transport layer, and a layer which injects and transports holes simultaneously, and one or more layers of the layers may include the compound represented by Chemical Formula 1.

In an exemplary embodiment, the organic material layer may include one or more layers of a hole injection layer and a hole transport layer, and one or more layers of the layers may include the compound represented by Chemical Formula 1.

In another exemplary embodiment, the organic material layer includes a hole injection layer, and the hole injection layer may include the compound represented by Chemical Formula 1 as a dopant.

In an exemplary embodiment, the organic material layer may include one or more layers of a hole injection layer, an electron blocking layer, a hole transport layer, and a layer which injects and transports holes simultaneously, and one or more layers of the layers may include the compound represented by Chemical Formula 1.

As another example, the organic material layer includes an electron blocking layer, and the electron blocking layer may include the compound represented by Chemical Formula 1.

In another exemplary embodiment, the organic material layer includes a light emitting layer, and the light emitting layer includes the compound represented by Chemical Formula 1. As an example, the compound represented by Chemical Formula 1 may be included as a host of the light emitting layer. As another example, the compound represented by Chemical Formula 1 may be included as a phosphorescent host of the light emitting layer.

As still another example, the organic material layer including the compound represented by Chemical Formula 1 may include the compound represented by Chemical Formula 1 as a host, and may include another organic compound, a metal or a metal compound as a dopant.

As yet another example, the organic material layer including the compound represented by Chemical Formula 1 may include the compound represented by Chemical Formula 1 as a host, and may use an iridium (Ir)-based dopant together.

Further, the organic material layer may include one or more layers of an electron transport layer, an electron injection layer, and a layer which transports and injects electrons simultaneously, and one or more layers of the layers may include the compound.

In another exemplary embodiment, the organic material layer of the organic light emitting device includes a hole transport layer, and the hole transport layer includes the compound represented by Chemical Formula 1.

In addition, the organic material layer includes two or more light emitting layers, and may include a charge generation layer including the compound of Chemical Formula 1, which is provided between the two light emitting layers, and the charge generation layer may include the compound represented by Chemical Formula 1.

According to an exemplary embodiment of the present specification, the organic material layer includes the light emitting layer, and the light emitting layer includes a compound represented by the following Chemical Formula 1-A.

[Chemical Formula 1-A]

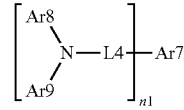

In Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Arg are a phenyl group which is unsubstituted or substituted with a trimethylgermanium group.

According to an exemplary embodiment of the present specification, Chemical Formula 1-A is represented by the following compound.

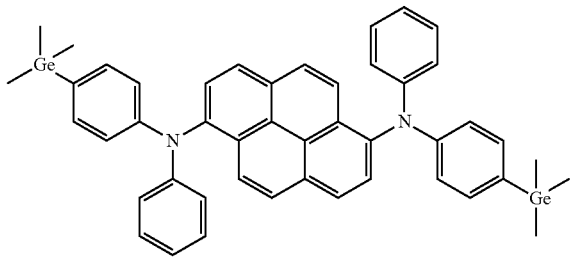

According to an exemplary embodiment of the present specification, the organic material layer includes a light emitting layer, and the light emitting layer includes a compound represented by the following Chemical Formula 2-A.

[Chemical Formula 2-A]

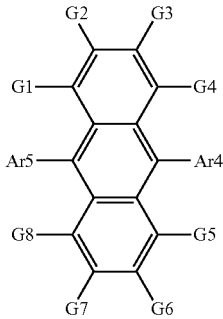

In Chemical Formula 2-A,

Ar4 and Ar5 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted alkyl group; a substituted or unsubstituted monocyclic aryl group; or a substituted or unsubstituted polycyclic aryl group.

In an exemplary embodiment, the organic material layer includes a light emitting layer, and the light emitting layer includes the compound represented by Chemical Formula 2-A as a host of the light emitting layer.

In an exemplary embodiment of the present invention, Ar4 and Ar5 are the same as or different from each other, and are each independently a substituted or unsubstituted polycyclic aryl group.

In an exemplary embodiment, Ar4 and Ar5 are the same as or different from each other, and are each independently a substituted or unsubstituted naphthyl group.

In an exemplary embodiment of the present invention, Ar4 and Ar5 are the same as or different from each other, and are each independently a substituted or unsubstituted 2-naphthyl group.

According to an exemplary embodiment, Ar4 and Ar5 are a 2-naphthyl group.

In an exemplary embodiment, G1 to G8 are the same as or different from each other, and are each independently hydrogen; or a substituted or unsubstituted alkyl group.

According to an exemplary embodiment, G1 to G8 are the same as or different from each other, and are each independently hydrogen; or a substituted or unsubstituted alkyl group having 1 to 20 carbon atoms.

In an exemplary embodiment of the present invention, G1 to G8 are the same as or different from each other, and are each independently hydrogen; or a methyl group.

According to an exemplary embodiment of the present invention, Chemical Formula 2-A is selected from the following compound.

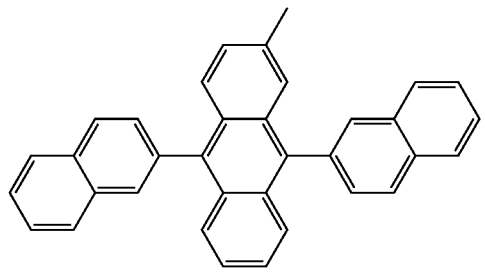 [SMILES: Cc1ccc2c(-c3ccc4ccccc4c3)c3ccccc3c(-c3ccc4ccccc4c3)c2c1]

In an exemplary embodiment, the organic material layer includes a light emitting layer, and the light emitting layer includes the compound represented by Chemical Formula 1-A as a dopant of the light emitting layer, and includes the compound represented by Chemical Formula 2-A as a host of the light emitting layer.

In the organic material layer having the multi-layered structure, the compound may be included in a light emitting layer, a layer which injects holes/transports holes and emits light simultaneously, a layer which transports holes and emits light simultaneously, or a layer which transports electrons and emits light simultaneously, and the like.

For example, the structure of the organic light emitting device of the present invention may have a structure as illustrated in FIGS. 1, 2 and 3, but is not limited thereto.

FIG. 1 exemplifies the structure of an organic light emitting device in which a positive electrode 2, a light emitting layer 3, and a negative electrode 4 are sequentially stacked on a substrate 1. In the structure as described above, the compound may be included in the light emitting layer 3.

FIG. 2 exemplifies the structure of an organic light emitting device in which a positive electrode 2, a hole injection layer 5, a hole transport layer 6, a light emitting layer 3, an electron transport layer 7, and a negative electrode 4 are sequentially stacked on a substrate 1. In the structure as described above, the compound may be included in the hole injection layer 5, the hole transport layer 6, the light emitting layer 3, or the electron transport layer 7.

FIG. 3 illustrates an example of an organic light emitting device including a substrate 1, a positive electrode 2, and a negative electrode 4, and including two units including hole injection layers 5a and 5b, hole transport layers 6a and 6b, light emitting layers 3a and 3b, and charge transport layers 8a and 8b between the positive electrode and the negative electrode, in which a charge generation layer 9 is provided between the units.

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may also be made by sequentially depositing a negative electrode material, an organic material layer, and a positive electrode material on a substrate.

The organic material layer may have a multi-layered structure including a hole injection layer, a hole transport layer, a light emitting layer, and an electron transport layer, and the like, but is not limited thereto and may have a single-layered structure. Further, the organic material layer may be manufactured with a fewer number of layers by a method such as a solvent process, for example, spin coating, dip coating, doctor blading, a screen printing, inkjet printing, or a thermal transfer method using various polymer materials, instead of a deposition method.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methyl compound), poly[3,4-(ethylene-1,2-dioxy)compound] (PEDT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a material which may well receive holes injected from a positive electrode at low voltage, and it is preferred that the highest occupied molecular orbital (HOMO) of the hole injection material is between the work function of the positive electrode material and the HOMO of the peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polycompound-based electrically conductive polymer, and the like, but are not limited thereto.

The hole transport material is a material which may receive holes transported from a positive electrode or a hole injection layer and transfer the holes to a light emitting layer, and is suitably a material having a large mobility for holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons transported from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

An iridium-based complex used as a dopant of a light emitting layer is as follows.

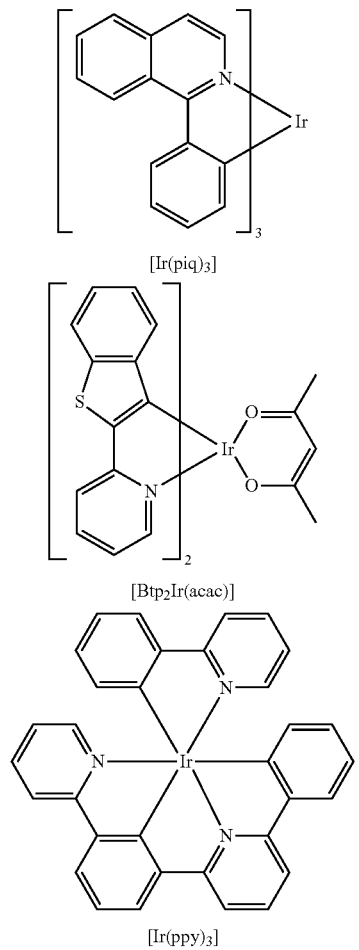

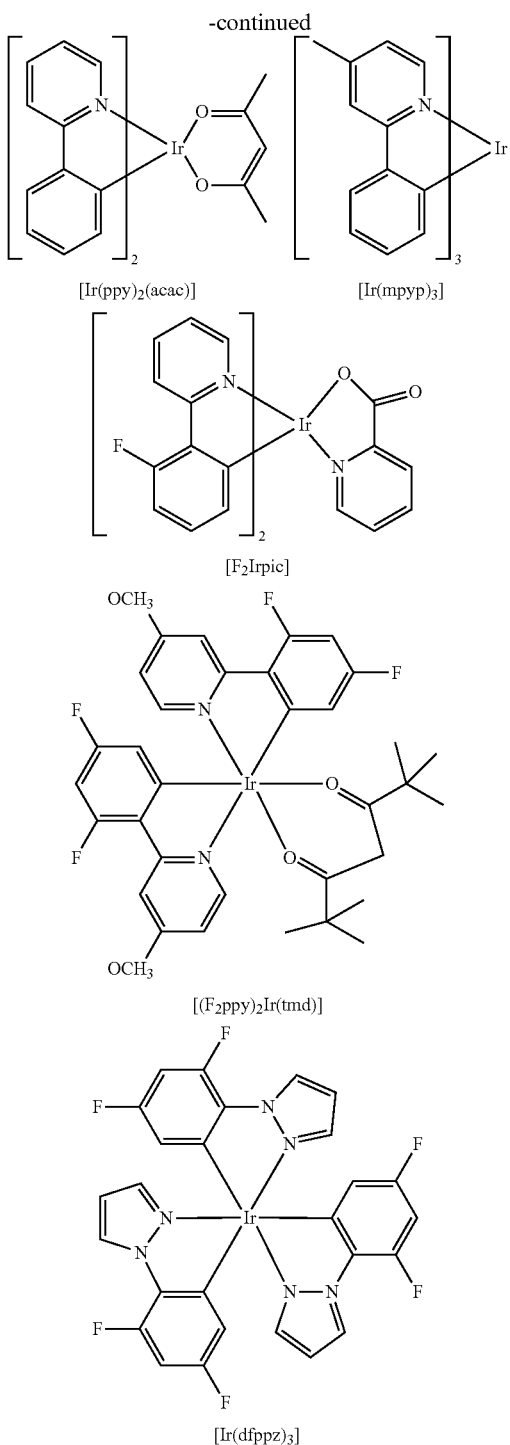

[Ir(ppy)₂(acac)]

[Ir(mpyp)₃]

[F₂Irpic]

[(F₂ppy)₂Ir(tmd)]

[Ir(dfppz)₃]

The electron transport material is a material which may well receive electrons injected from a negative electrode and transfer the electrons to a light emitting layer, and is suitably a material having a large mobility for electrons. Specific examples thereof include: an Al complex of 8-hydroxyquinoline; a complex including Alq₃; an organic radical compound; a hydroxyflavone-metal complex, and the like, but are not limited thereto.

The organic light emitting device according to the present invention may be a top emission type, a bottom emission type, or a dual emission type according to the material to be used.

The compound according to the present invention may be operated by a principle which is similar to the principle applied to an organic light emitting device, even in an organic electronic device including an organic solar cell, an organic photoconductor, an organic transistor, and the like.

The preparation method of the compound of Chemical Formula 1 and the manufacture of an organic light emitting device using the same will be specifically described in the following Examples. However, the following Examples are provided for exemplifying the present invention, and the scope of the present invention is not limited thereby.

PREPARATION EXAMPLES

Preparation Example 1

Synthesis of Intermediate A

Intermediate A was synthesized with reference to the published paper *Macromolecules*, 2005, 38, 19.

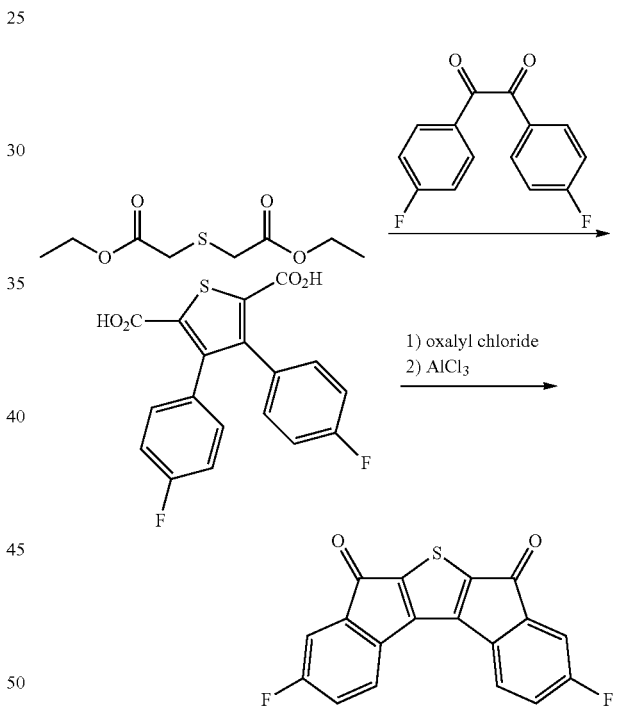

4.0 g of diethyl thioacetate and 4.9 g of 4,4'-difluorobenzyl were dissolved in 60 ml of ethanol, 3.6 g of sodium methoxide was introduced thereinto, and the resulting mixture was stirred at normal temperature for 48 hours. Next, distilled water was introduced thereinto, and a solid content produced by distilling ethanol under reduced pressure was removed. A solid precipitated by treating the obtained filtrate with 1 N hydrochloric acid was filtered, washed with ion exchange water, and then dried to obtain 3.9 g of a white solid. A peak was confirmed at M/Z=360 by measuring the mass spectrum of the obtained solid.

Next, 3.9 g of the solid was dissolved in 400 ml of anhydrous dichloromethane, and the solution temperature was cooled to −4° C. or less. 5.8 g of oxalyl chloride and 0.1 ml of dimethylformamide were added dropwise to the solution under a nitrogen condition. After the completion of the dropwise addition, the resulting solution was stirred at room temperature for 2 hours, and further refluxed and stirred for 6 hours. The solution was left to cool, and distilled under reduced pressure to remove the solvent. Next, the residue was dissolved in 400 ml of anhydrous dichloromethane, the resulting solution was mixed with 4.4 g of aluminum trichloride under a nitrogen condition, and the resulting mixture was stirred at normal temperature for 12 hours. Thereafter, the mixture was cooled to 0° C., and a dilute aqueous hydrochloric acid solution was added dropwise to the mixture, and the mixture was separated by using dichloromethane. Thereafter, the resulting product was dried over anhydrous sodium sulfate and filtered. The dichloromethane was distilled and removed under reduced pressure, and the residue was subjected to column chromatography with silica gel (eluent: dichloromethane) to obtain 2.2 g of a compound. A peak was confirmed at M/Z=324 by measuring the mass spectrum of the obtained solid.

Synthesis of Compound 37

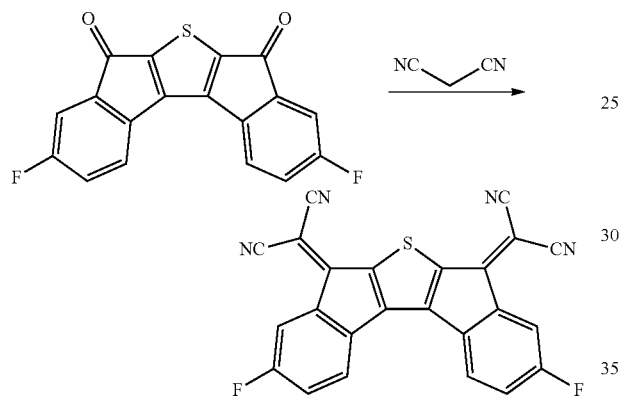

2.0 g of synthesized Intermediate A, 1.63 g of malononitrile, and 50 ml of pyridine were added to a container, and the resulting mixture was heated and stirred at 80° C. for 8 hours. After the mixture was left to cool, the solid was filtered, washed with water, ethanol, and toluene, and then dried under reduced pressure to obtain 0.8 g of a solid. A peak was confirmed at M/Z=420 by measuring the mass spectrum of the obtained solid.

Preparation Example 2

Synthesis of Compound 38

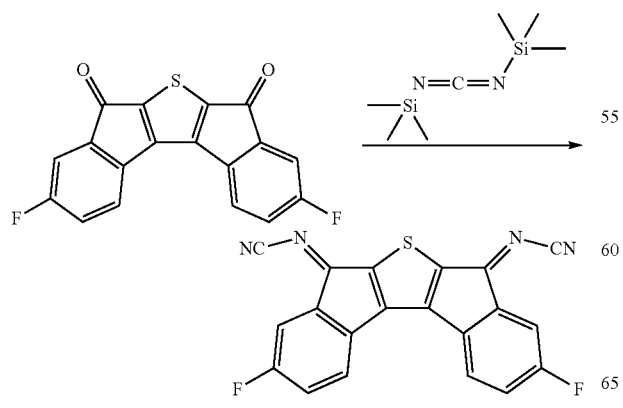

2.0 g of Intermediate A synthesized in Preparation Example 1 was dissolved in 120 ml of methylene chloride while being stirred under a nitrogen condition, and the solution temperature was cooled to approximately −10° C. 4.7 g of titanium tetrachloride was added to the solution, and then a mixed solution of 14.0 g of bistrimethylsilylcarbodiimide and 80 ml of methylene chloride was added dropwise thereto. After the completion of the dropwise addition, cooling was continued for 1 hour, and then the resulting product was stirred at room temperature for 4 hours, and further refluxed and stirred for 2 hours. A precipitated solid was filtered, and washed with distilled water, methanol, and toluene to obtain 0.7 g of a solid. A peak was confirmed at M/Z=372 by measuring the mass spectrum of the obtained solid.

Preparation Example 3

Synthesis of Intermediate B

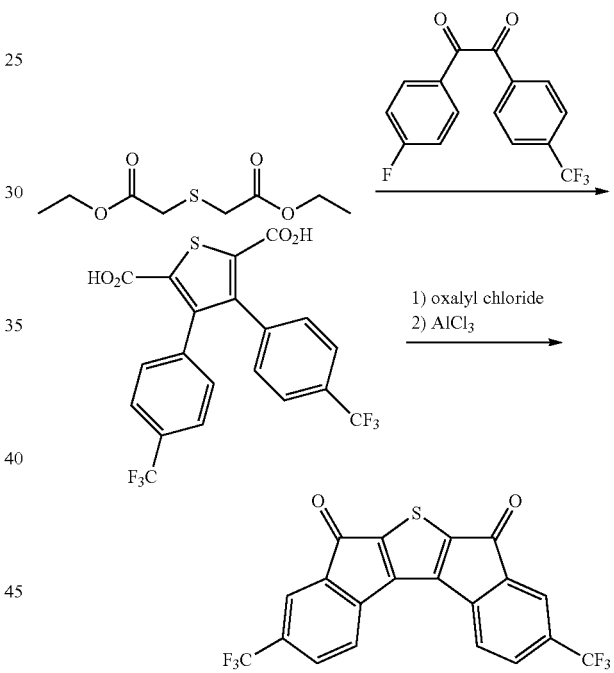

2.4 g of Intermediate B was obtained by performing the same operation as in the synthesis of Intermediate A in Preparation Example 1, except that 6.8 g of 4,4'-(ditrifluoromethyl)benzyl was used instead of 4.9 g of 4,4'-difluorobenzyl. A peak was confirmed at M/Z=424 by measuring the mass spectrum of the obtained solid.

Synthesis of Compound 13

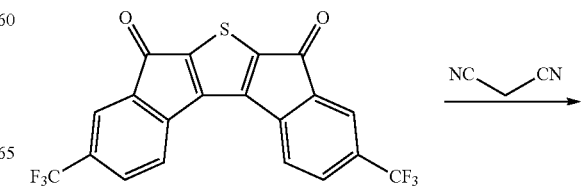

47

-continued

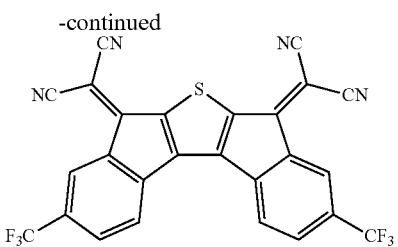

0.8 g of Compound 13 was obtained by performing the same operation as in the synthesis of Compound 1 in Preparation Example 1, except that 2.0 g of Intermediate A was changed into 2.6 g of Intermediate B. A peak was confirmed at M/Z=520 by measuring the mass spectrum of the obtained solid.

Preparation Example 4

Synthesis of Intermediate C

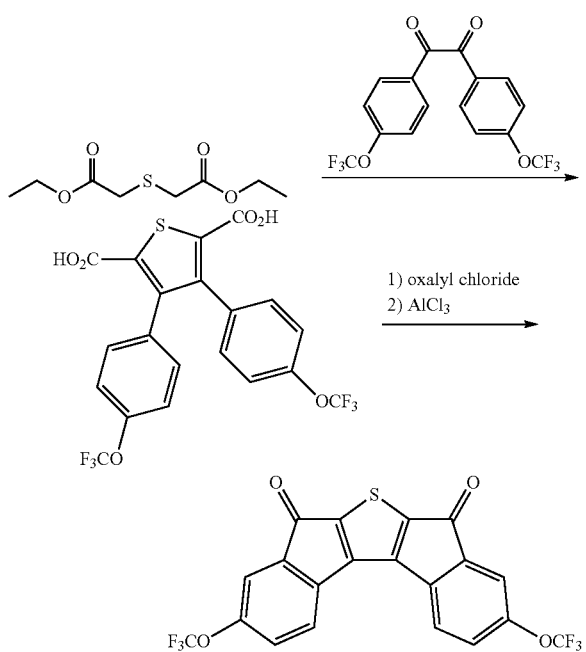

4.0 g of diethyl thioacetate and 7.6 g of 4,4'-di(trifluoromethoxy)benzyl were dissolved in 60 ml of ethanol, 3.6 g of sodium methoxide was introduced thereinto, and the resulting mixture was stirred at normal temperature for 48 hours. Next, distilled water was introduced thereinto, and a solid content produced by distilling ethanol under reduced pressure was removed. Next, a solid precipitated by treating the filtrate with 1 N hydrochloric acid was filtered, washed with ion exchange water, and then dried to obtain 3.9 g of a white solid. A peak was confirmed at M/Z=492 by measuring the mass spectrum of the obtained solid.

Next, 3.9 g of the solid was dissolved in 360 ml of anhydrous dichloromethane, the resulting solution was mixed with 6.0 g of oxalyl chloride and 0.1 ml of dimethylformamide under a nitrogen condition, and the resulting mixture was stirred at normal temperature. Thereafter, the mixture was refluxed and stirred under a nitrogen condition for 8 hours. The mixture was left to cool, and distilled under reduced pressure to remove the solvent. Next, the residue was dissolved in 360 ml of anhydrous dichloromethane, the resulting solution was mixed with 4.4 g of aluminum trichlo-

48 ride under a nitrogen condition, and the resulting mixture was stirred at normal temperature for 12 hours. Thereafter, the mixture was cooled to 0° C., and a dilute aqueous hydrochloric acid solution was added dropwise to the mixture, and the mixture was separated by using dichloromethane. Thereafter, the resulting product was dried over anhydrous sodium sulfate and filtered. The dichloromethane was distilled and removed under reduced pressure, and the residue was subjected to column chromatography with silica gel to obtain 2.4 g of a compound. A peak was confirmed at M/Z=456 by measuring the mass spectrum of the obtained solid.

Synthesis of Compound 39

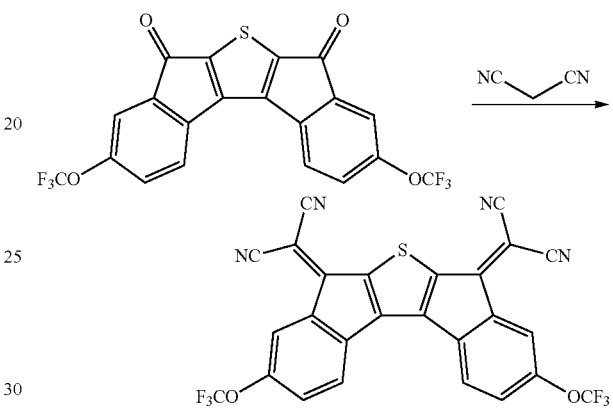

2.0 g of synthesized Intermediate C, 1.74 g of malononitrile, and 50 ml of pyridine were added to a container, and the resulting mixture was heated and stirred at 80° C. for 8 hours. After the mixture was left to cool, the solid was filtered, washed with water, ethanol, and toluene, and then dried under reduced pressure to obtain 0.8 g of a solid. A peak was confirmed at M/Z=552 by measuring the mass spectrum of the obtained solid.

Preparation Example 5

Synthesis of Compound 40

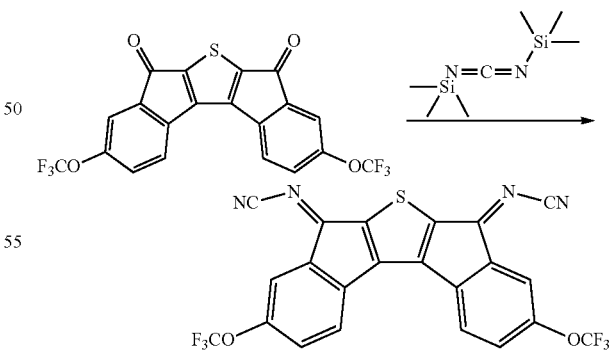

2.8 g of Intermediate C synthesized in Preparation Example 4 was dissolved in 120 ml of methylene chloride while being stirred under a nitrogen condition, and the solution temperature was cooled to approximately −10° C. 4.7 g of titanium tetrachloride was added to the solution, and then a mixed solution of 14.0 g of bistrimethylsilylcarbodiimide and 80 ml of methylene chloride was added dropwise thereto. After the completion of the dropwise addition, cooling was continued for 1 hour, and then the resulting product was stirred at room temperature for 4 hours, and further refluxed and stirred for 2 hours. A precipitated solid was filtered, and washed with distilled water, methanol, and toluene to obtain 0.8 g of a solid. A peak was confirmed at M/Z=504 by measuring the mass spectrum of the obtained solid.

Preparation Example 6

Synthesis of Intermediate D

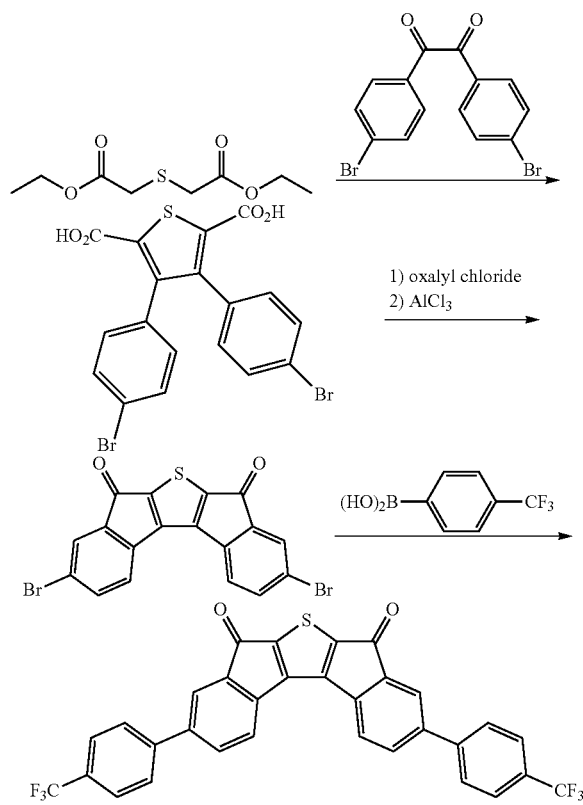

4.0 g of diethyl thioacetate and 7.4 g of 4,4'-di(bromo)benzyl were dissolved in 60 ml of ethanol, 3.6 g of sodium methoxide was introduced thereinto, and the resulting mixture was stirred at normal temperature for 48 hours. Next, distilled water was introduced thereinto, and a solid content produced by distilling ethanol under reduced pressure was removed. Next, a solid precipitated by treating the filtrate with 1 N hydrochloric acid was filtered, washed with ion exchange water, and then dried to obtain 3.6 g of a white solid. A peak was confirmed at M/Z=482 by measuring the mass spectrum of the obtained solid.

Next, 3.6 g of the solid was dissolved in 240 ml of anhydrous dichloromethane, the resulting solution was mixed with 3.8 g of oxalyl chloride and 0.1 ml of dimethylformamide under a nitrogen condition, and the resulting mixture was stirred at normal temperature. Thereafter, the mixture was refluxed and stirred under a nitrogen condition for 12 hours. The mixture was left to cool, and distilled under reduced pressure to remove the solvent. Next, the residue was dissolved in 240 ml of anhydrous dichloromethane, the resulting solution was mixed with 4.0 g of aluminum trichloride under a nitrogen condition, and the resulting mixture was stirred at normal temperature for 12 hours. Thereafter, the mixture was cooled to 0° C., and a dilute aqueous hydrochloric acid solution was added dropwise to the mixture, and the mixture was separated by using dichloromethane. Thereafter, the resulting product was dried over anhydrous sodium sulfate and filtered. The dichloromethane was distilled and removed under reduced pressure, and the residue was subjected to column chromatography with silica gel to obtain 2.0 g of a compound. A peak was confirmed at M/Z=446 by measuring the mass spectrum of the obtained solid.

Next, 2.0 g of the obtained solid was mixed with 2.0 g of 4-trifluoromethylphenylboronic acid, 0.51 g of tetrakis(triphenylphosphine)palladium(0), 25 ml of 1.1 M potassium carbonate, and 40 ml of toluene, and the resulting mixture was refluxed and stirred under a nitrogen flow for 10 hours. After the mixture was cooled, the reaction solution was filtered, and the residue was washed with water, ethanol, and toluene to obtain 2.4 g of Intermediate D. A peak was confirmed at M/Z=577 by measuring the mass spectrum of the obtained solid.

Synthesis of Compound 1

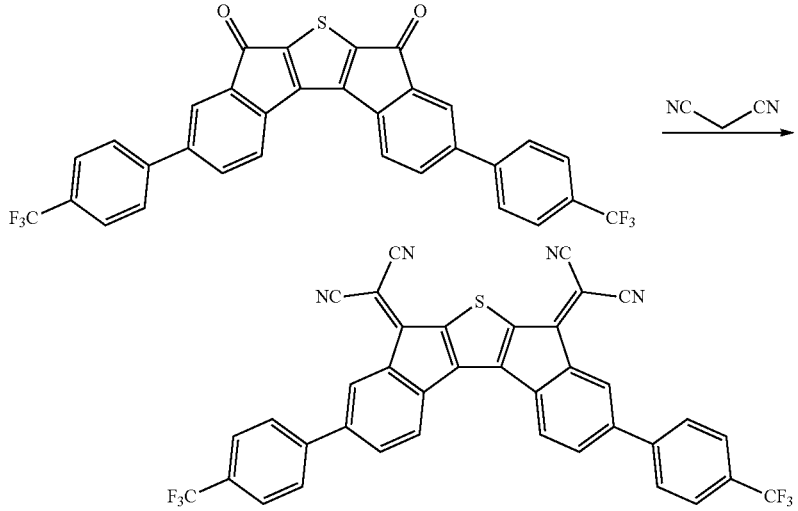

2.0 g of synthesized Intermediate D, 1.37 g of malononitrile, and 40 ml of pyridine were added to a container, and the resulting mixture was heated and stirred at 80° C. for 8 hours. After the mixture was left to cool, the solid was filtered, washed with water, ethanol, and toluene, and then dried under reduced pressure to obtain 1.2 g of a solid. A peak was confirmed at M/Z=673 by measuring the mass spectrum of the obtained solid.

Preparation Example 7

Synthesis of Intermediate E

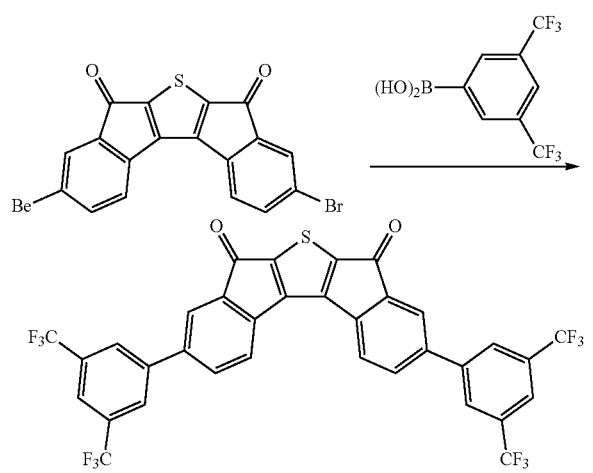

2.2 g of Intermediate E was obtained by performing the same operation as in the synthesis of Intermediate D in Preparation Example 6, except that 3.0 g of 3,5-bistrifluoromethylphenylboronic acid was used instead of 2.0 g of 4-trifluoromethylphenylboronic acid. A peak was confirmed at M/Z=706 by measuring the mass spectrum of the obtained solid.

Synthesis of Compound 3

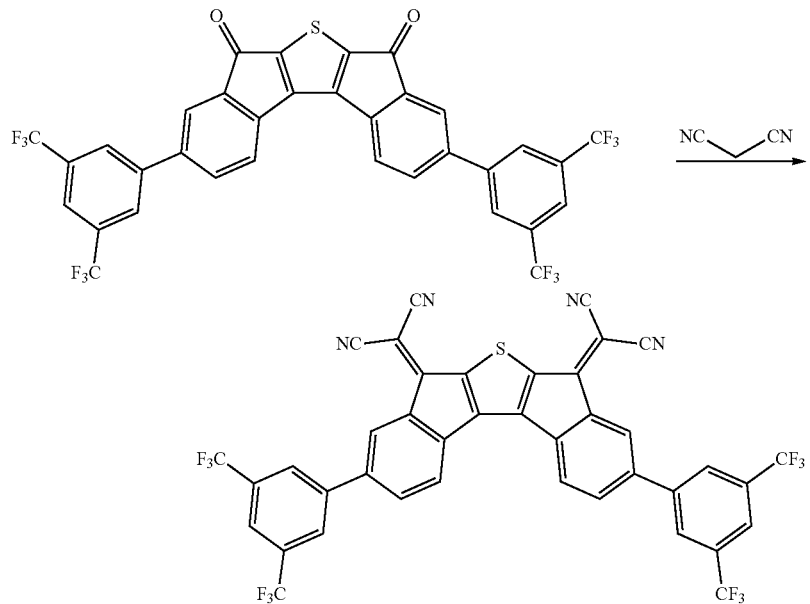

2.0 g of synthesized Intermediate E, 1.11 g of malononitrile, and 40 ml of pyridine were added to a container, and the resulting mixture was heated and stirred at 80° C. for 8 hours. After the mixture was left to cool, the solid was filtered, washed with water, ethanol, and toluene, and then dried under reduced pressure to obtain 0.8 g of a solid. A peak was confirmed at M/Z=809 by measuring the mass spectrum of the obtained solid.

Preparation Example 8

Synthesis of Intermediate F

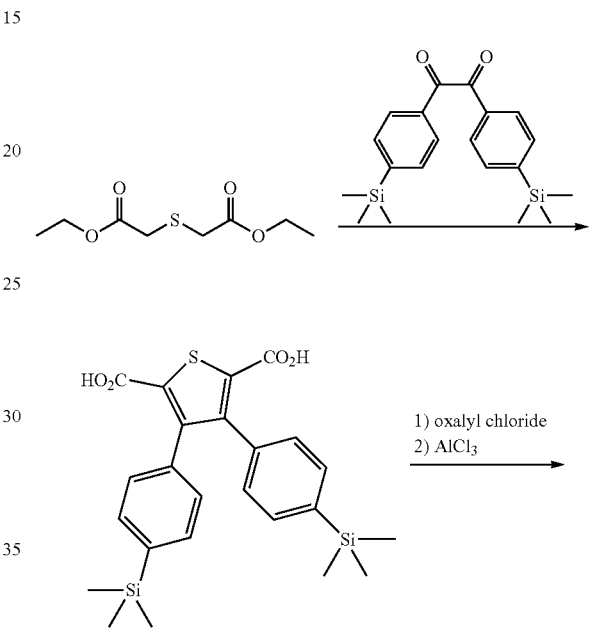

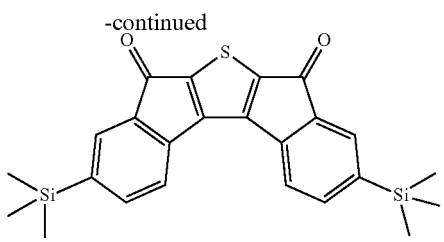

4.0 g of diethyl thioacetate and 7.1 g of 4,4'-di(trimethylsilyl)benzyl were dissolved in 60 ml of ethanol, 3.6 g of sodium methoxide was introduced thereinto, and the resulting mixture was stirred at normal temperature for 48 hours. Next, distilled water was introduced thereinto, and a solid content produced by distilling ethanol under reduced pressure was removed. Next, a solid precipitated by treating the filtrate with 1 N hydrochloric acid was filtered, washed with ion exchange water, and then dried to obtain 3.6 g of a white solid. A peak was confirmed at M/Z=469 by measuring the mass spectrum of the obtained solid.

Next, 3.6 g of the solid was dissolved in 160 ml of anhydrous dichloromethane, the resulting solution was mixed with 3.0 g of oxalyl chloride and 0.1 ml of dimethylformamide under a nitrogen condition, and the resulting mixture was stirred at normal temperature. Thereafter, the mixture was refluxed and stirred under a nitrogen condition for 12 hours. The mixture was left to cool, and distilled under reduced pressure to remove the solvent. Next, the residue was dissolved in 160 ml of anhydrous dichloromethane, the resulting solution was mixed with 3.2 g of aluminum trichloride under a nitrogen condition, and the resulting mixture was stirred at normal temperature for 12 hours. Thereafter, the mixture was cooled to 0° C., and a dilute aqueous hydrochloric acid solution was added dropwise to the mixture, and the mixture was separated by using dichloromethane. Thereafter, the resulting product was dried over anhydrous sodium sulfate and filtered. The dichloromethane was distilled and removed under reduced pressure, and the residue was subjected to column chromatography with silica gel to obtain 1.0 g of a compound. A peak was confirmed at M/Z=469 by measuring the mass spectrum of the obtained solid.

Synthesis of Compound 78

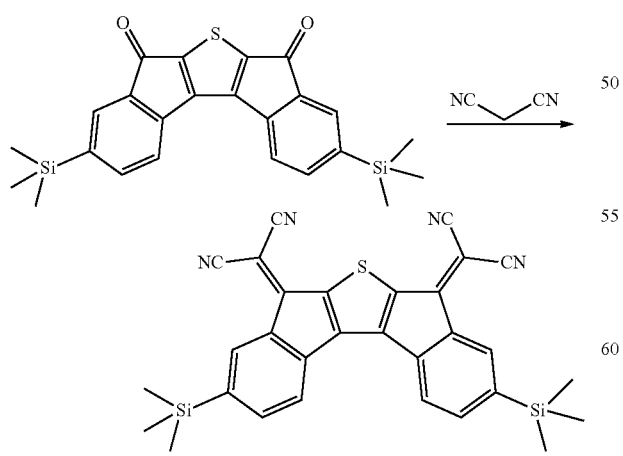

1.0 g of synthesized Intermediate F, 0.9 g of malononitrile, and 30 ml of pyridine were added to a container, and the resulting mixture was heated and stirred at 60° C. for 12 hours. After the mixture was left to cool, the solid was filtered, washed with water, ethanol, and toluene, and then dried under reduced pressure to obtain 0.5 g of a solid. A peak was confirmed at M/Z=529 by measuring the mass spectrum of the obtained solid.

Preparation Example 9

Synthesis of Intermediate G

Intermediate G was synthesized with reference to the published paper *Chemical Science* 2014, 5, 4490.

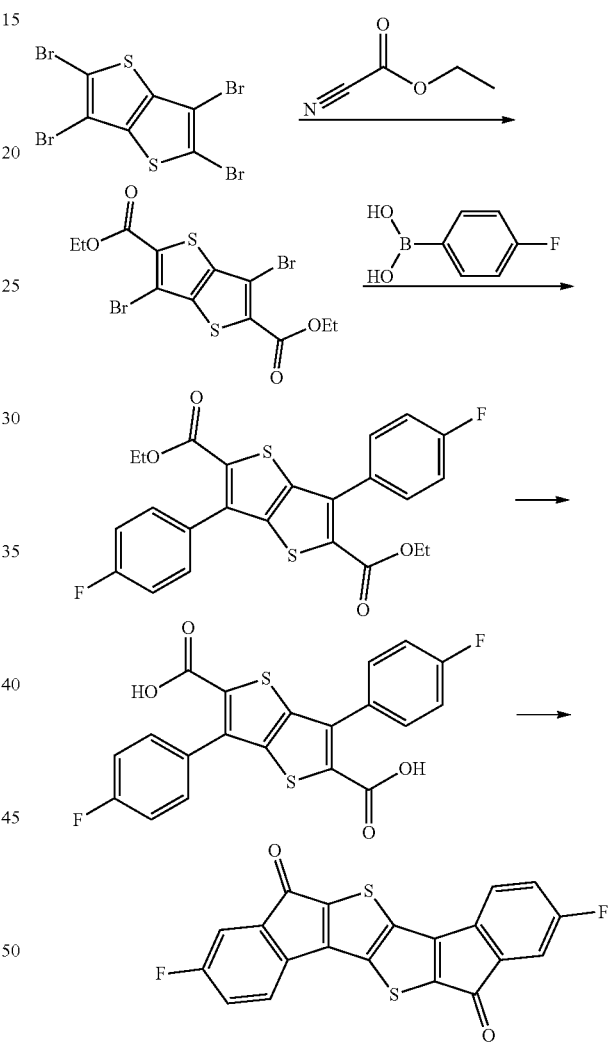

4.6 g of 2,3,5,6-tetrabromothieno[3,2-b]thiophene was dissolved in 80 ml of tetrahydrofuran at −78° C. under a nitrogen condition, 8.1 ml of n-butyllithium (2.5 M in hexane) was slowly added dropwise thereto, and the resulting mixture was stirred for 1 hour. Thereafter, 2.0 ml of ethyl cyanoformate was slowly added dropwise thereto at −78° C., and the resulting mixture was slowly warmed to normal temperature and stirred for 12 hours. Thereafter, the mixture was cooled to 0° C., a dilute aqueous hydrochloric acid solution was added dropwise thereto, the organic solvent was distilled and removed under reduced pressure to obtain a solid, and then the solid was filtered and washed with hexane and methanol to obtain 5.2 g of a solid. A peak was confirmed at M/Z=442 by measuring the mass spectrum of the obtained solid.

Next, 5.2 g of the obtained solid was mixed with 4.0 g of 4-fluorophenylboronic acid, 1.36 g of tetrakis(triphenylphosphine)palladium(0), 40 ml of 1.1 M potassium carbonate, and 80 ml of toluene, and the resulting mixture was refluxed and stirred under a nitrogen flow for 8 hours. After the mixture was cooled, the reaction solution was filtered, and the residue was washed with water, ethanol, and toluene to obtain 4.8 g of a solid. A peak was confirmed at M/Z=473 by measuring the mass spectrum of the obtained solid.

Next, 1.90 g of the obtained solid was dissolved in 80 ml of methanol and 80 ml of tetrahydrofuran (1:1 v/v), 0.96 g of sodium hydroxide was added thereto, and the resulting mixture was stirred under a refluxing condition for 12 hours. Thereafter, the solvent was distilled and removed under reduced pressure, and a precipitate was filtered by adding 37% hydrochloric acid thereto. The precipitate was washed with distilled water and toluene, and then dried under reduced pressure to obtain 1.4 g of a solid.

Next, 1.5 g of the obtained solid was dissolved in 80 ml of anhydrous dichloromethane, the resulting solution was mixed with 4 ml of thionyl chloride and 0.1 ml of dimethylformamide under a nitrogen condition, and the resulting mixture was stirred at normal temperature. Thereafter, the mixture was refluxed and stirred under a nitrogen condition for 12 hours. The mixture was left to cool, and distilled under reduced pressure to remove the solvent. Next, the residue was dissolved in 80 ml of anhydrous dichloromethane, the resulting solution was mixed with 2.1 g of aluminum trichloride under a nitrogen condition, and the resulting mixture was stirred at normal temperature for 12 hours. Thereafter, the mixture was cooled to 0° C., and a solid produced by adding dropwise a dilute aqueous hydrochloric acid solution thereto was filtered, and then washed with 10% sodium hydroxide, methanol, and tetrahydrofuran to obtain 1.0 g of a solid. A peak was confirmed at M/Z=380 by measuring the mass spectrum of the obtained solid.

Synthesis of Compound 81

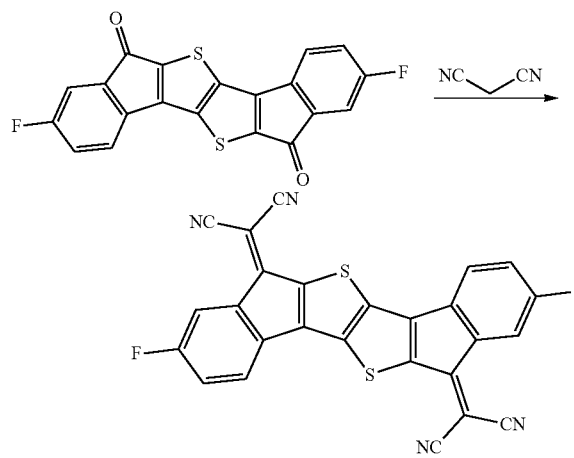

1.0 g of synthesized Intermediate G, 1.0 g of malononitrile, and 20 ml of pyridine were added to a container, and the resulting mixture was heated and stirred at 60° C. for 12 hours. After the mixture was left to cool, the solid was filtered, washed with water, ethanol, and toluene, and then dried under reduced pressure to obtain 0.6 g of a solid. A peak was confirmed at M/Z=476 by measuring the mass spectrum of the obtained solid.

Preparation Example 10

Synthesis of Compound 83

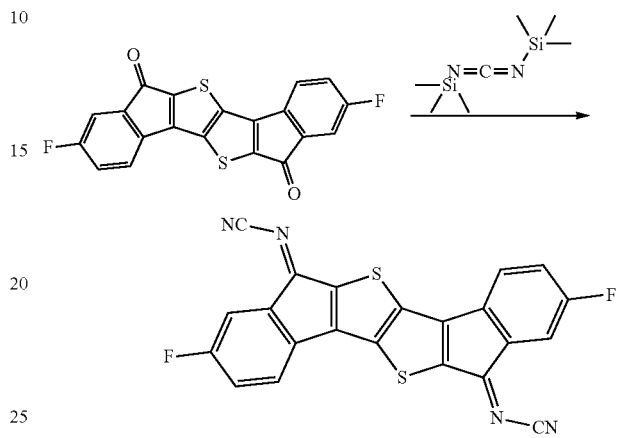

1.2 g of Intermediate G synthesized in Preparation Example 9 was dissolved in 60 ml of methylene chloride while being stirred under a nitrogen condition, and the solution temperature was cooled to approximately −10° C. 2.4 g of titanium tetrachloride was added to the solution, and then a mixed solution of 7.0 g of bistrimethylsilylcarbodiimide and 40 ml of methylene chloride was added dropwise thereto. After the completion of the dropwise addition, cooling was continued for 1 hour, and then the resulting product was stirred at room temperature for 4 hours, and further refluxed and stirred for 2 hours. A precipitated solid was filtered, and washed with distilled water, methanol, and toluene to obtain 0.5 g of a solid. A peak was confirmed at M/Z=428 by measuring the mass spectrum of the obtained solid.

Preparation Example 11

Synthesis of Intermediate H

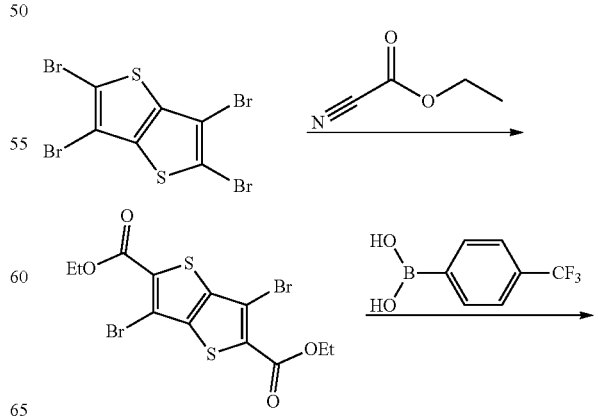

-continued

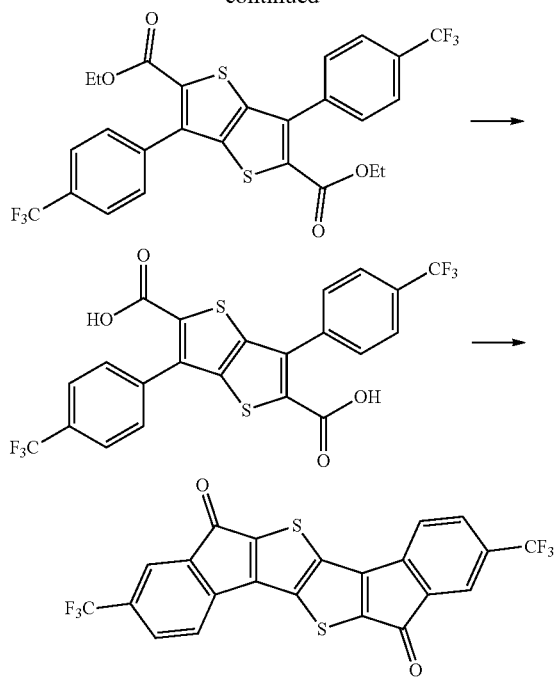

1.0 g of Intermediate H was obtained by performing the same operation as in the synthesis of Intermediate G in Preparation Example 9, except that 5.4 g of 4-trifluoromethylphenylboronic acid was used instead of 4.0 g of 4-fluoromethylphenylboronic acid. A peak was confirmed at M/Z=480 by measuring the mass spectrum of the obtained solid.

Synthesis of Compound 84

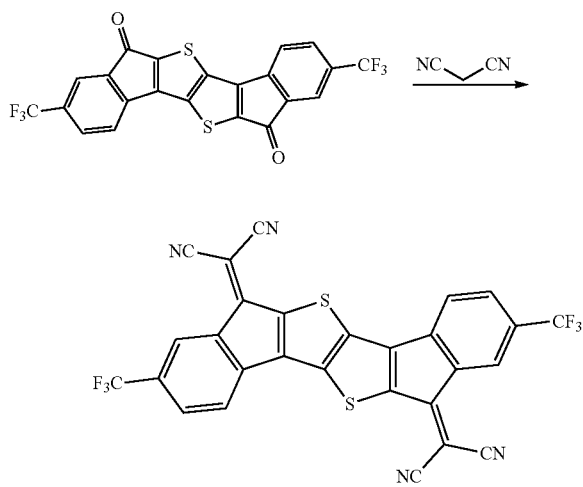

1.0 g of synthesized Intermediate H, 0.8 g of malononitrile, and 20 ml of pyridine were added to a container, and the resulting mixture was heated and stirred at 60° C. for 12 hours. After the mixture was left to cool, the solid was filtered, washed with water, ethanol, and toluene, and then dried under reduced pressure to obtain 0.4 g of a solid. A peak was confirmed at M/Z=576 by measuring the mass spectrum of the obtained solid.

Preparation Example 12

Synthesis of Intermediate I

Intermediate I was synthesized with reference to the published paper *Tetrahedron* 2009, 65, 6141.

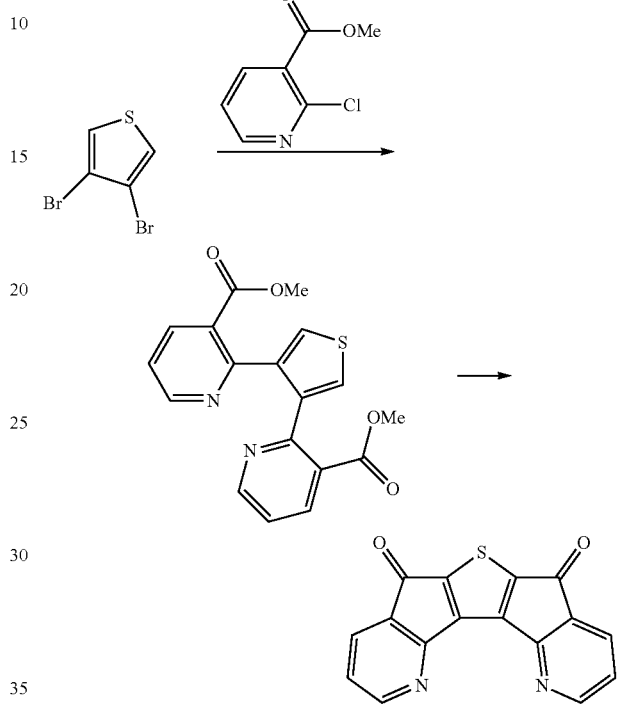

0.76 g of a nickel bromide 2,2'-bipyridine complex and 2.52 g of a manganese powder were dissolved in 16 ml of dimethylformamide, and 2.4 g of 3,4-dibromothiophene, 4.46 g of methyl 2-chloronicotinate, and 0.1 ml of trifluoroacetic acid were sequentially introduced into the resulting solution. 0.76 g of a nickel bromide 2,2'-bipyridine complex and 2.52 g of a manganese powder were additionally introduced into the solution at an interval of 2 hours, and the reaction was terminated 6 hours later. Thereafter, extraction was performed with chloroform and an aqueous ammonium chloride solution, and the obtained organic layer was dried over sodium sulfate (MgSO$_4$). Thereafter, after the separation and filtration were performed, the solvent was distilled and removed under reduced pressure, and the residue was subjected to column chromatography with silica gel to obtain 0.6 g of a compound.

Next, the compound was dissolved in 24 ml of polyphosphoric acid (PPA), and the resulting solution was heated at 210° C., and then added dropwise to a cooled aqueous sodium carbonate solution. Extraction was performed with chloroform, and the obtained organic layer was dried over sodium sulfate (MgSO$_4$). Thereafter, after the separation and filtration were performed, the solvent was distilled and removed under reduced pressure, and the residue was subjected to column chromatography with silica gel to obtain 0.4 g of a compound.

Synthesis of Compound 65

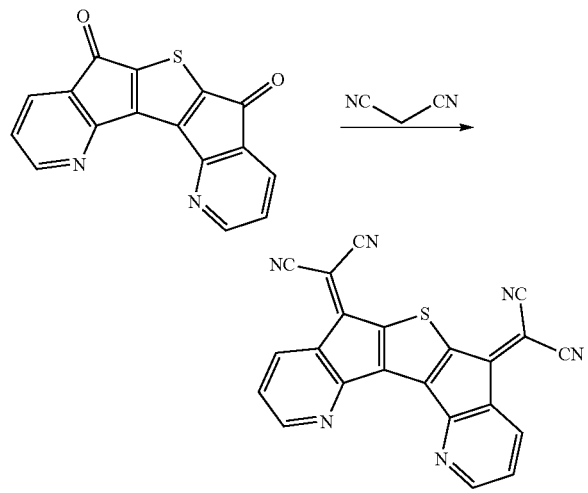

0.4 g of synthesized Intermediate I, 0.54 g of malononitrile, and 20 ml of pyridine were added to a container, and the resulting mixture was heated and stirred at 60° C. for 12 hours. After the mixture was left to cool, the solid was filtered, washed with water, ethanol, and toluene, and then dried under reduced pressure to obtain 0.3 g of a solid. A peak was confirmed at M/Z=386 by measuring the mass spectrum of the obtained solid.

Experimental Examples

Experimental Example 1

An ITO glass was patterned and then washed, such that the light emitting area of the ITO glass became 3 mm×3 mm. After a substrate was placed in a vacuum chamber, the base pressure was set to $1\times10^{-6}$ torr, and then Compound 37 was formed to have a thickness of 100 Å as a hole injection layer on the ITO being a positive electrode. Subsequently, α-NPD was formed to have a thickness of 600 Å as a hole transport layer, BD-A being a dopant was deposited on MADN being a host at a weight ratio of 40:2 as a light emitting layer, Alq$_3$ was formed to have a thickness of 300 Å as an electron transport layer, LiF was formed to have a thickness of 10 Å as an electron injection layer, and then Al was formed to have a thickness of 800 Å as a negative electrode, thereby manufacturing an organic light emitting device. The luminance was measured by using CS1000 manufactured by Minolta Co., Ltd., and the light emitting efficiency was calculated at 10 mA/cm$^2$.

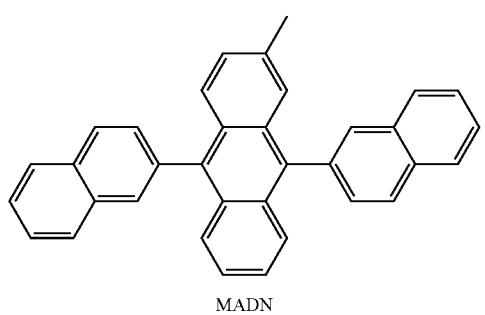

MADN

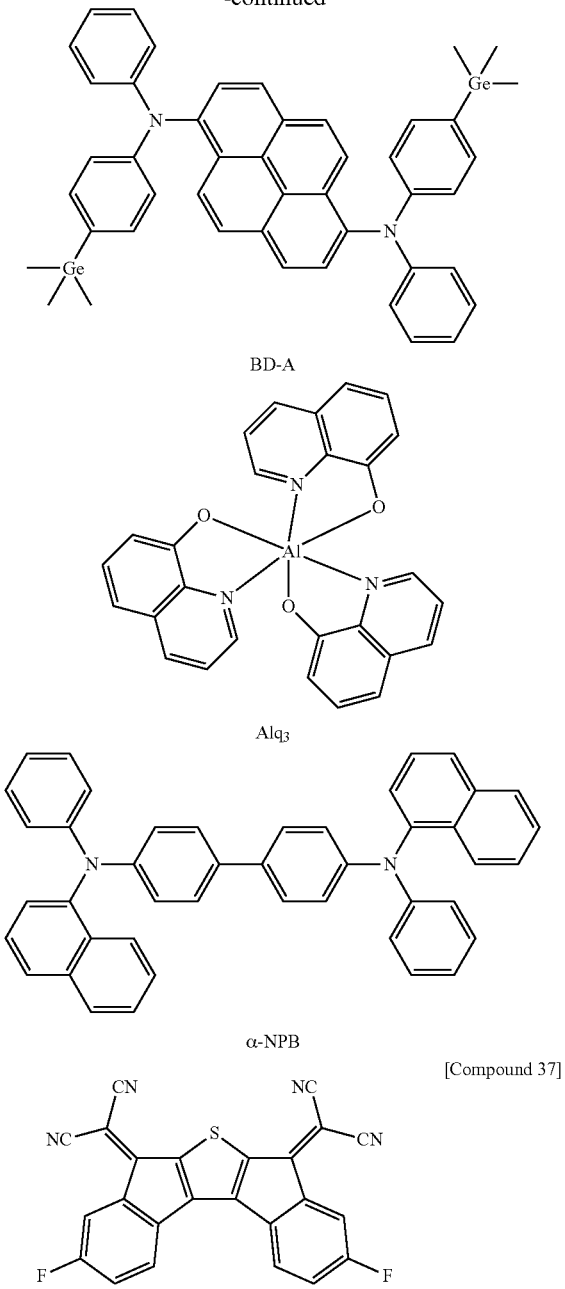

Experimental Example 2

An organic light emitting device was manufactured under the same process conditions as in the above-described Experimental Example 1, except that Compound 13 instead of Compound 37 was used in the hole injection layer.

Experimental Example 3

An organic light emitting device was manufactured under the same process conditions as in the above-described Experimental Example 1, except that Compound 39 instead of Compound 37 was used in the hole injection layer.

Experimental Example 4

An organic light emitting device was manufactured under the same process conditions as in the above-described Experimental Example 1, except that Compound 1 instead of Compound 37 was used in the hole injection layer.

Experimental Example 5

An organic light emitting device was manufactured under the same process conditions as in the above-described Experimental Example 1, except that Compound 3 instead of Compound 37 was used in the hole injection layer.

Experimental Example 6

An organic light emitting device was manufactured under the same process conditions as in the above-described Experimental Example 1, except that Compound 78 instead of Compound 37 was used in the hole injection layer.

Experimental Example 7

An organic light emitting device was manufactured under the same process conditions as in the above-described Experimental Example 1, except that Compound 81 instead of Compound 37 was used in the hole injection layer.

Experimental Example 8

An organic light emitting device was manufactured under the same process conditions as in the above-described Experimental Example 1, except that Compound 65 instead of Compound 37 was used in the hole injection layer.

Comparative Example 1

An organic light emitting device was manufactured under the same process conditions as in the above-described Experimental Example 1, except that HAT-CN instead of Compound 37 was used in the hole injection layer.

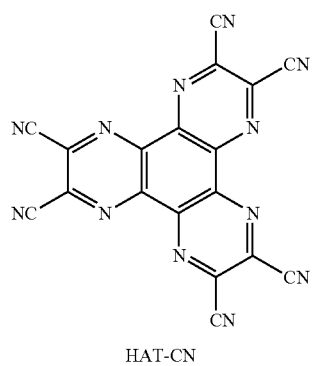 [SMILES: N#Cc1nc2c3nc(C#N)c(C#N)nc3c3nc(C#N)c(C#N)nc3c2nc1C#N]

HAT-CN

Comparative Example 2

An organic light emitting device was manufactured under the same process conditions as in the above-described Experimental Example 1, except that α-NPD instead of Compound 37 was used in the hole injection layer.

Comparative Example 3

An organic light emitting device was manufactured under the same process conditions as in the above-described Experimental Example 1, except that the following compound instead of Compound 37 was used in the hole injection layer.

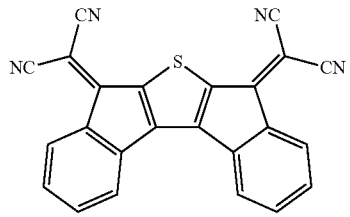 [SMILES: N#CC(C#N)=C1c2ccccc2-c2c1sc1c2-c2ccccc2C1=C(C#N)C#N]

TABLE 1

| | Driving voltage (V) | Current density (mA/cm$^2$) | Current efficiency (cd/A) | Power efficiency (lm/W) | Luminance (cd/m$^2$) |
|---|---|---|---|---|---|
| Experimental Example 1 (Compound 37) | 4.2 | 10 | 5.86 | 4.383 | 586 |
| Experimental Example 2 (Compound 13) | 4.0 | 10 | 6.02 | 4.728 | 602 |
| Experimental Example 3 (Compound 39) | 4.0 | 10 | 5.96 | 4.681 | 596 |
| Experimental Example 4 (Compound 1) | 4.5 | 10 | 5.62 | 3.924 | 562 |
| Experimental Example 5 (Compound 3) | 4.3 | 10 | 5.52 | 4.033 | 552 |
| Experimental Example 6 (Compound 78) | 4.8 | 10 | 5.34 | 3.495 | 534 |
| Experimental Example 7 (Compound 81) | 4.9 | 10 | 5.18 | 3.321 | 518 |
| Experimental Example 8 (Compound 65) | 4.7 | 10 | 5.42 | 3.623 | 542 |
| Comparative Example 1 | 5.8 | 10 | 4.52 | 2.448 | 452 |
| Comparative Example 2 | 8.0 | 10 | 4.12 | 1.618 | 412 |
| Comparative Example 3 | 6.0 | 10 | 4.48 | 2.346 | 448 |

Referring to Table 1, the driving voltages in Experimental Examples 1 to 8 of the present invention were decreased by 16 to 31% as compared to Comparative Example 1 and decreased by 39 to 50% as compared to Comparative Example 2. Further, the current efficiencies, the power efficiencies, and the luminances in the Experimental Examples of the present invention were improved as compared to the Comparative Examples.

As another Example, the present specification provides Examples in which an organic light emitting device was manufactured by doping a hole injection layer with the compound according to the present invention.

Experimental Example 9

An ITO glass was patterned and then washed, such that the light emitting area of the ITO glass became 3 mm×3 mm. After a substrate was placed in a vacuum chamber, the base pressure was set to 1×10$^{-6}$ torr, and then α-NPD was formed to have a thickness of 100 Å as a hole injection layer on the ITO being a positive electrode, in which the hole injection layer was doped with Compound 37 at a doping concentration of 25%, α-NPD was formed to have a thickness of 600 Å as a hole transport layer, BD-A being a dopant was deposited on MADN being a host at a weight ratio of 40:2 as a light emitting layer, Alq₃ was formed to have a thickness of 300 Å as an electron transport layer, LiF was formed to have a thickness of 10 Å as an electron injection layer, and then Al was formed to have a thickness of 800 Å as a negative electrode, thereby manufacturing an organic light emitting device. The luminance was measured by using CS1000 manufactured by Minolta Co., Ltd., and the light emitting efficiency was calculated at 10 mA/cm².

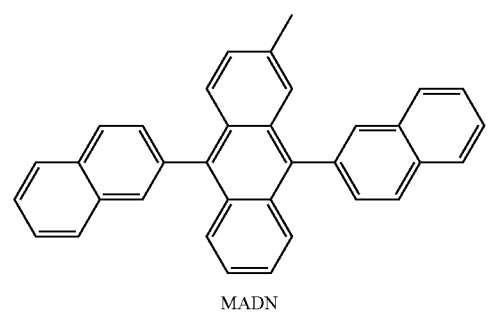

MADN

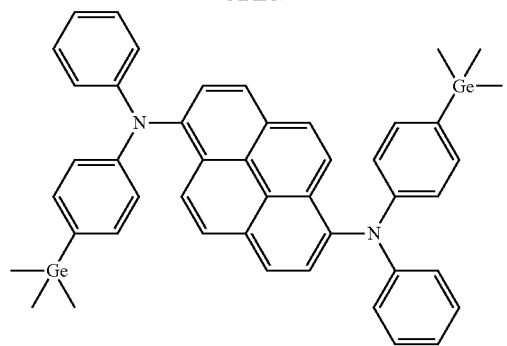

BD-A

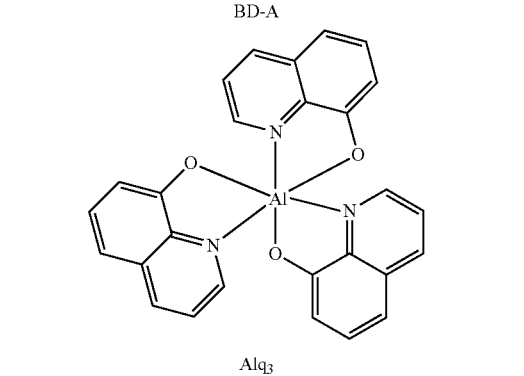

Alq₃

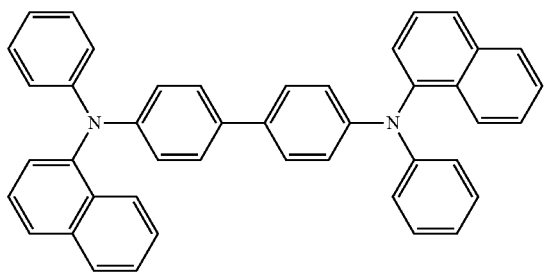

a-NPB

Experimental Example 10

An organic light emitting device was manufactured under the same process conditions as in the above-described Experimental Example 9, except that the hole injection layer was doped with Compound 1 at a doping concentration of 25% instead of Compound 37.

Experimental Example 11

An organic light emitting device was manufactured under the same process conditions as in the above-described Experimental Example 9, except that the hole injection layer was doped with Compound 13 at a doping concentration of 25% instead of Compound 37.

Experimental Example 12

An organic light emitting device was manufactured under the same process conditions as in the above-described Experimental Example 9, except that the hole injection layer was doped with Compound 39 at a doping concentration of 25% instead of Compound 37.

Experimental Example 13

An organic light emitting device was manufactured under the same process conditions as in the above-described Experimental Example 9, except that the hole injection layer was doped with Compound 65 at a doping concentration of 25% instead of Compound 37.

Comparative Example 4

An organic light emitting device was manufactured under the same process conditions as in the above-described Experimental Example 9, except that the hole injection layer was doped with HAT-CN at a doping concentration of 25% instead of Compound 37.

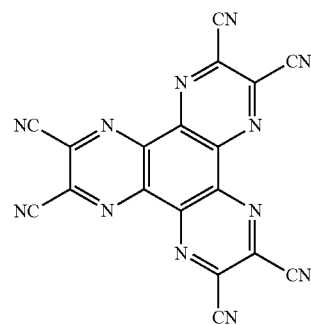

HAT-CN

Comparative Example 5

An organic light emitting device was manufactured under the same process conditions as in the above-described Experimental Example 9, except that α-NPD was used in the hole injection layer without doping.

Comparative Example 6

An organic light emitting device was manufactured under the same process conditions as in the above-described Experimental Example 1, except that the hole injection layer was doped with the following compound at a doping concentration of 25% instead of Compound 37.

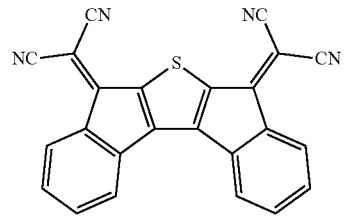 [SMILES: N#CC(C#N)=C1c2ccccc2-c2c1sc1c2-c2ccccc2C1=C(C#N)C#N]

TABLE 2

| | Driving voltage (V) | Current density (mA/cm$^2$) | Current efficiency (cd/A) | Power efficiency (lm/W) | Luminance (cd/m$^2$) |
|---|---|---|---|---|---|
| Experimental Example 9 (Compound 37) | 4.4 | 10 | 5.56 | 3.970 | 556 |
| Experimental Example 10 (Compound 1) | 4.6 | 10 | 5.5 | 3.756 | 550 |
| Experimental Example 11 (Compound 13) | 4.2 | 10 | 5.86 | 4.383 | 586 |
| Experimental Example 12 (Compound 39) | 4.2 | 10 | 5.59 | 4.181 | 559 |
| Experimental Example 13 (Compound 65) | 4.7 | 10 | 5.4 | 3.609 | 540 |
| Comparative Example 4 | 5.8 | 10 | 4.5 | 2.437 | 450 |
| Comparative Example 5 | 8.0 | 10 | 4.12 | 1.618 | 412 |
| Comparative Example 6 | 6.0 | 10 | 4.39 | 2.299 | 439 |

Referring to Table 2, the driving voltages in Experimental Examples 9 to 13 of the present invention were decreased by 19 to 28% as compared to Comparative Example 4 and decreased by 41 to 47% as compared to Comparative Example 5. Further, the current efficiencies, the power efficiencies, and the luminances in the Experimental Examples of the present invention were improved as compared to the Comparative Examples.

EXPLANATION OF REFERENCE NUMERALS AND SYMBOLS

1: Substrate
2: Positive electrode
3: Light emitting layer
4: Negative electrode
5, 5a, and 5b: Hole injection layer
6, 6a, and 6b: Hole transport layer
7: Electron transport layer
8a and 8b: Charge transport layer
9: Charge generation layer

The invention claimed is:

1. A compound represented by the following Chemical Formula 1:

[Chemical Formula 1]

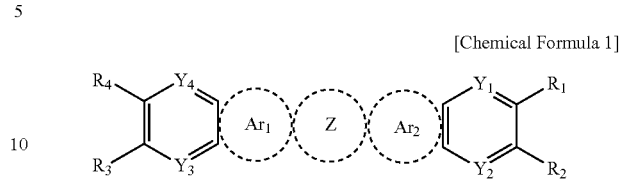

in Chemical Formula 1,

Z is a thiophene ring or a thienothiophene ring,

Ar$_1$ is

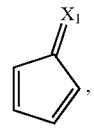,

Ar$_2$ is

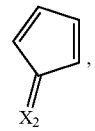,

X$_1$ and X$_2$ are the same as or different from each other, and are each independently any one selected from the following (a) to (g),

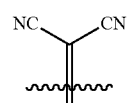 (a)

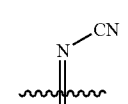 (b)

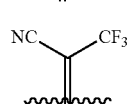 (c)

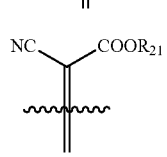 (d)

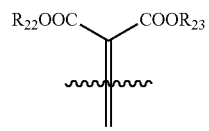 (e)

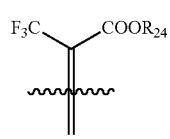
(f)

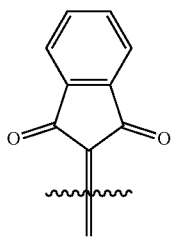
(g)

$Y_1$ to $Y_4$ are the same as or different from each other, and are each independently N or $CR_5$, $R_1$ to $R_5$ are the same as or different from each other, and are each independently hydrogen; deuterium; a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; a substituted or unsubstituted silyl group; or a substituted or unsubstituted hetero ring, when Z is a thiophene ring, all of $Y_1$ to $Y_4$ are CH, and $X_1$ and $X_2$ are the same as or different from each other and are each any one of (a) to (f), then at least one of $R_1$ to $R_4$ is a halogen group; a nitrile group; a substituted or unsubstituted alkyl group; a substituted or unsubstituted haloalkyl group; a substituted or unsubstituted alkoxy group; a substituted or unsubstituted haloalkoxy group; a substituted or unsubstituted aryl group; a substituted or unsubstituted haloaryl group; a substituted or unsubstituted silyl group; or a substituted or unsubstituted heterocyclic group, or adjacent groups of $R_1$ to $R_5$ combine with each other to form a substituted or unsubstituted aromatic hydrocarbon ring or a substituted or unsubstituted hetero ring, and $R_{21}$ to $R_{24}$ are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heterocyclic group.

2. The compound of claim 1, wherein the compound of Chemical Formula 1 is represented by any one of the following Chemical Formulae 2 to 4:

[Chemical Formula 2]

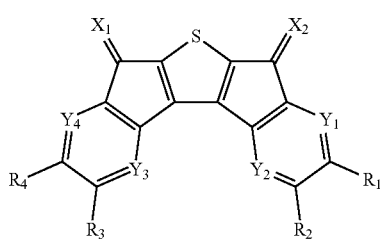

[Chemical Formula 3]

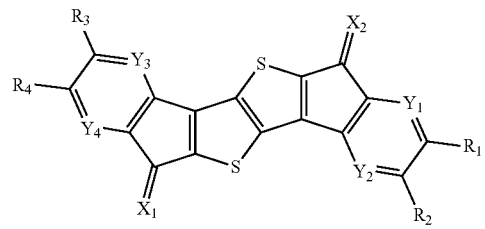

[Chemical Formula 4]

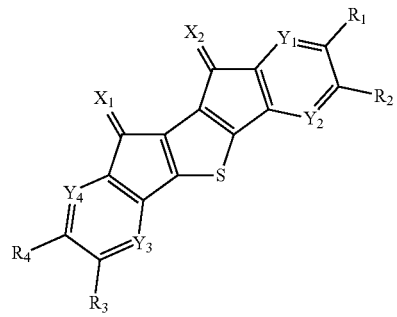

in Chemical Formulae 2 to 4, definitions of $X_1$, $X_2$, $Y_1$ to $Y_4$, $R_1$ to $R_5$, and $R_{21}$ to $R_{24}$ are the same as those in Chemical Formula 1.

3. The compound of claim 1, wherein the compound of Chemical Formula 1 is represented by any one of the following Chemical Formulae 5 to 8:

[Chemical Formula 5]

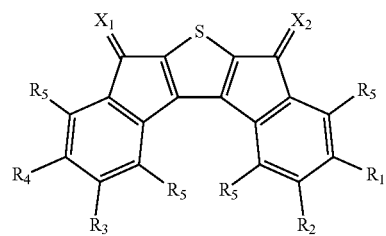

[Chemical Formula 6]

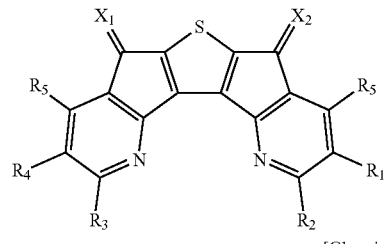

[Chemical Formula 7]

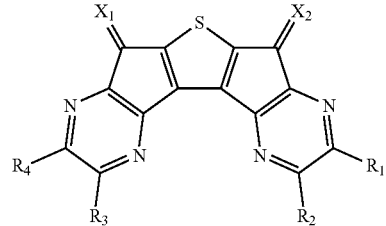

[Chemical Formula 8]

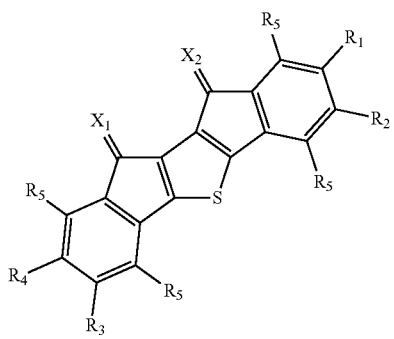

[Chemical Formula 10]

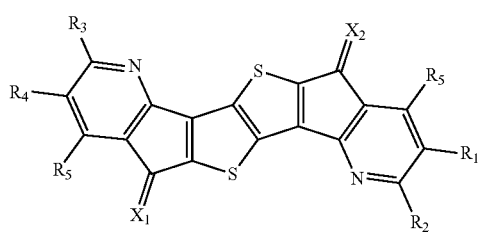

[Chemical Formula 11]

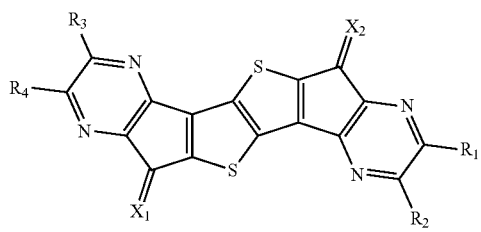

in Chemical Formulae 5 to 8,
definitions of $X_1$, $X_2$, $Y_1$ to $Y_4$, $R_1$ to $R_5$, and $R_{21}$ to $R_{24}$ are the same as those in Chemical Formula 1.

4. The compound of claim 1, wherein the compound of Chemical Formula 1 is represented by any one of the following Chemical Formulae 9 to 11:

[Chemical Formula 9]

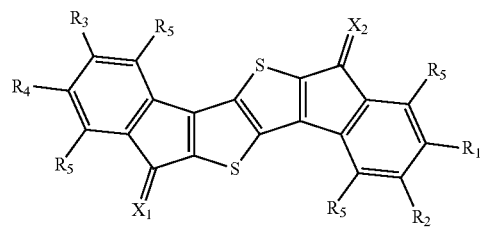

in Chemical Formulae 9 to 11,
definitions of $X_1$, $X_2$, $Y_1$ to $Y_4$, $R_1$ to $R_5$, and $R_{21}$ to $R_{24}$ are the same as those in Chemical Formula 1.

5. The compound of claim 1, wherein the compound of Chemical Formula 1 is any one selected from the following compounds:

1

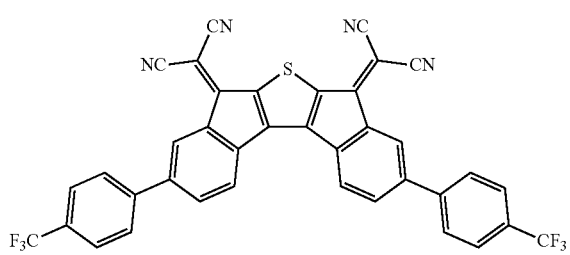

2

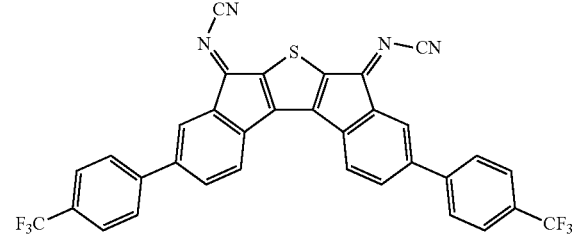

3

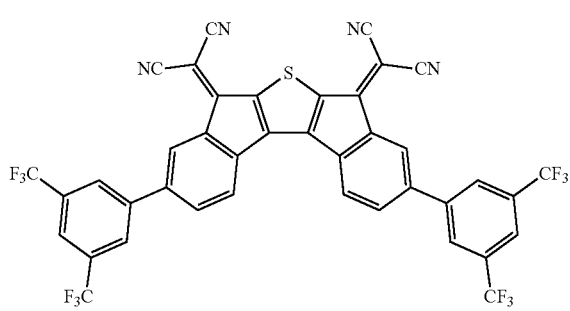

4

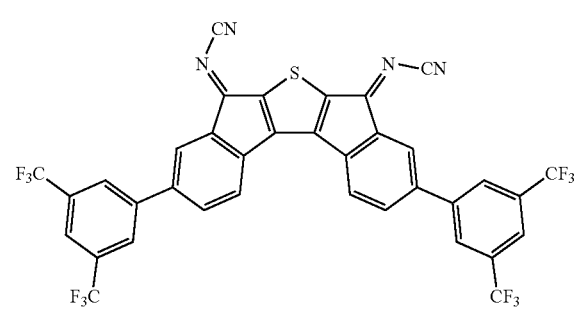

-continued
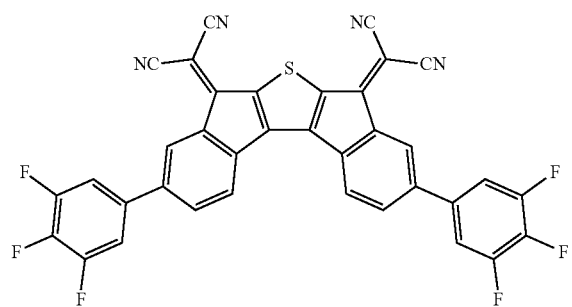
5
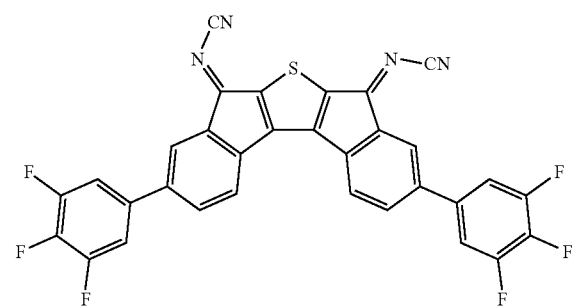
6
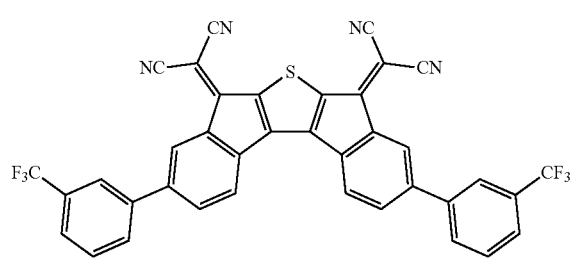
7
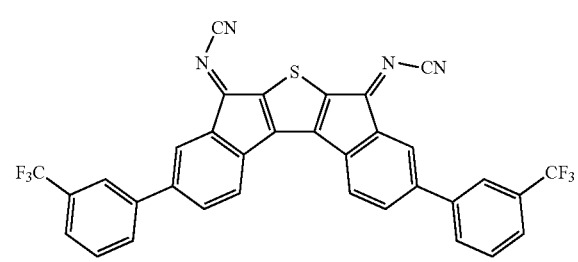
8
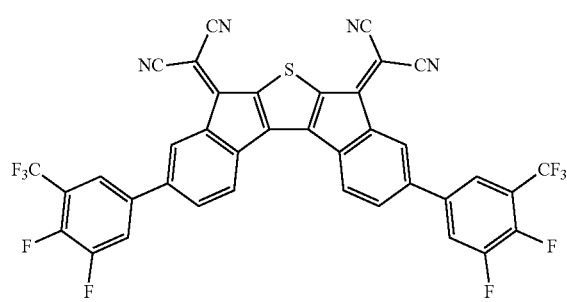
9
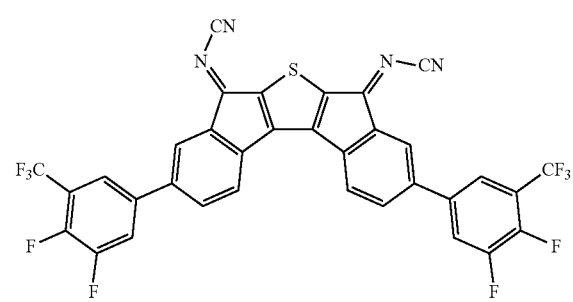
10
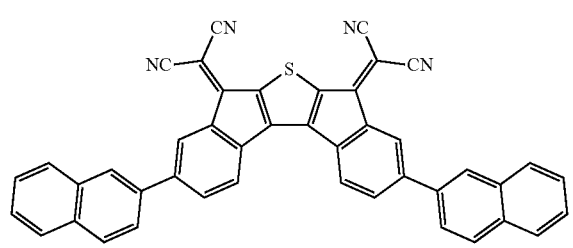
11
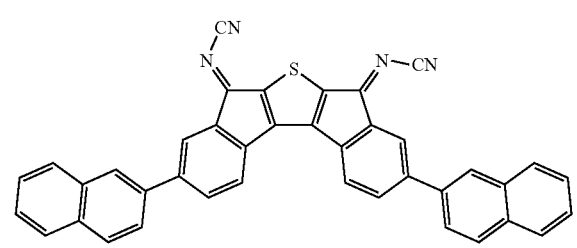
12
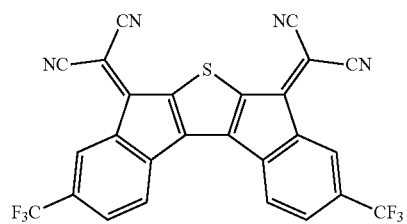
13
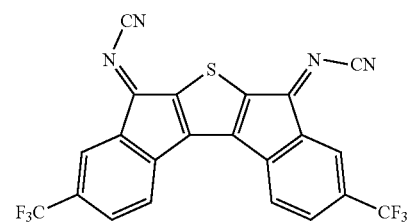
14
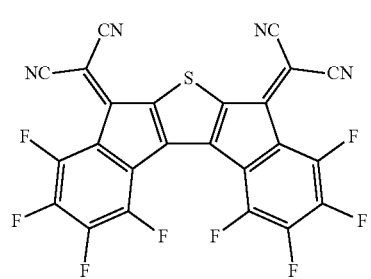
15
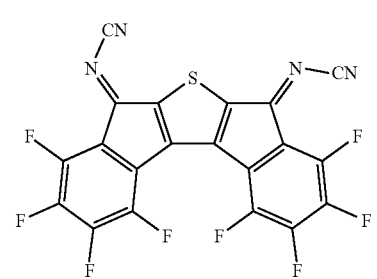
16

-continued
17
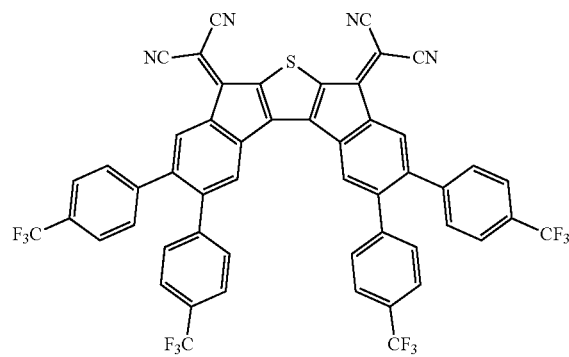
18
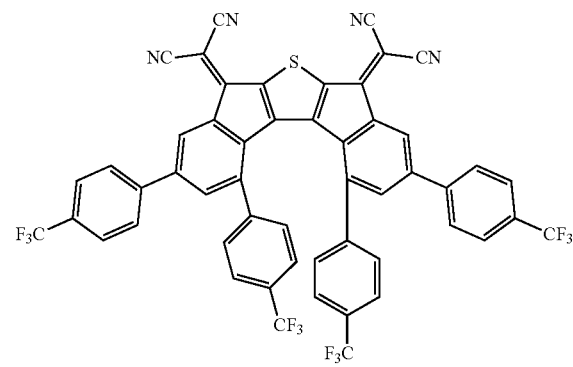
19
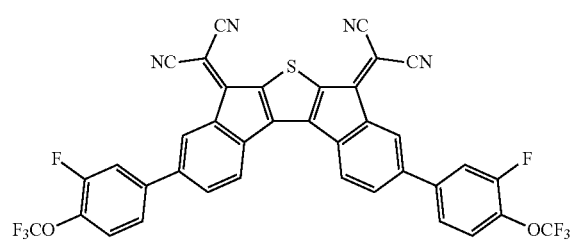
20
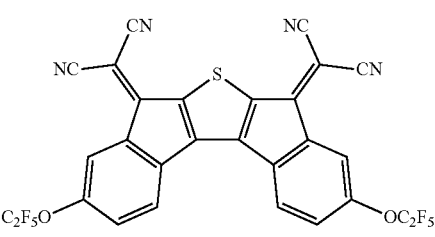
21
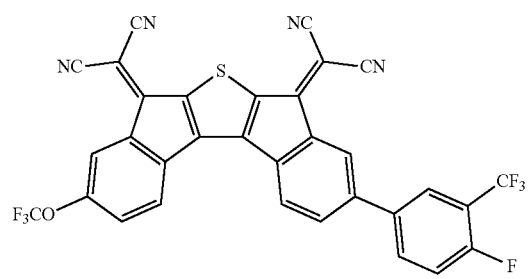
22
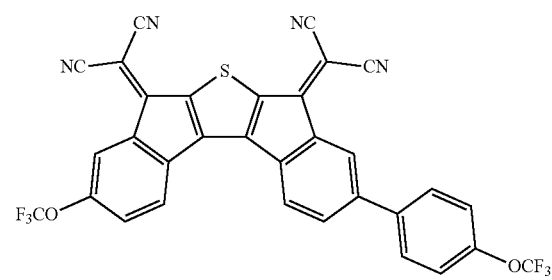
23
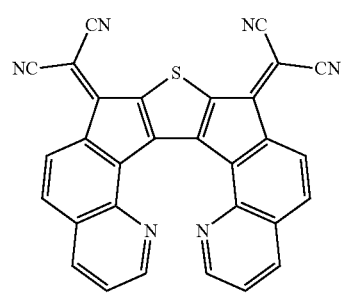
24
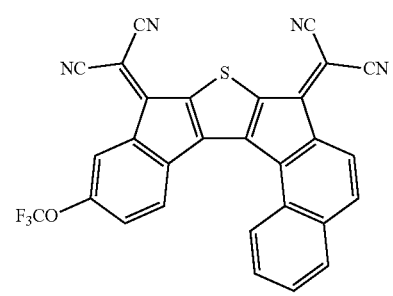
25
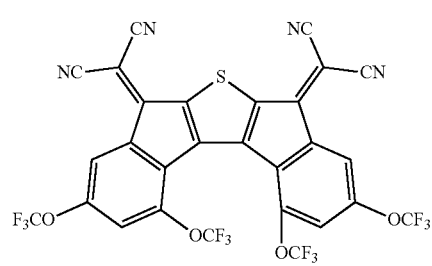
26
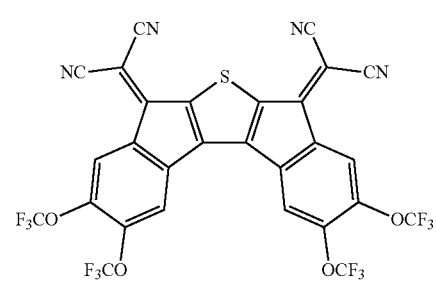

-continued
27
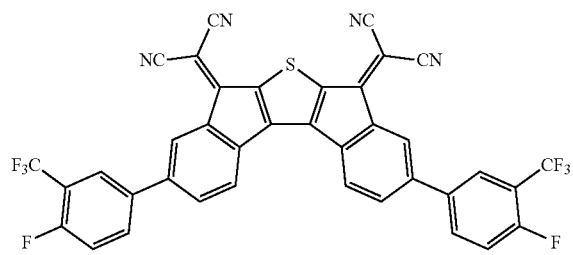
28
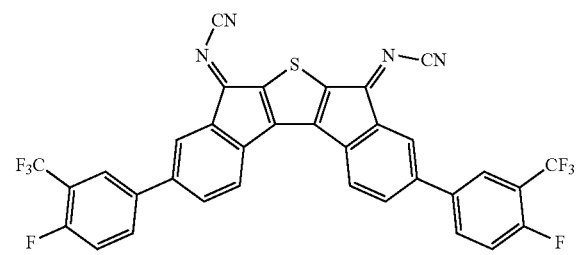
29
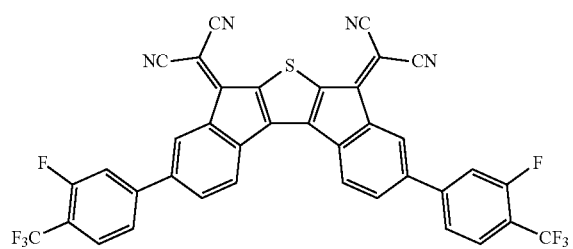
30
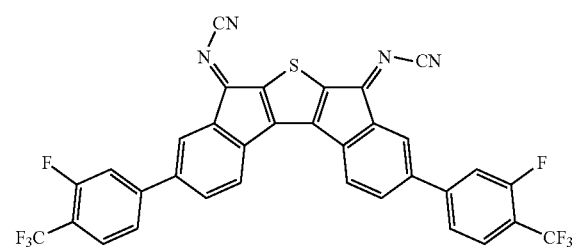
31
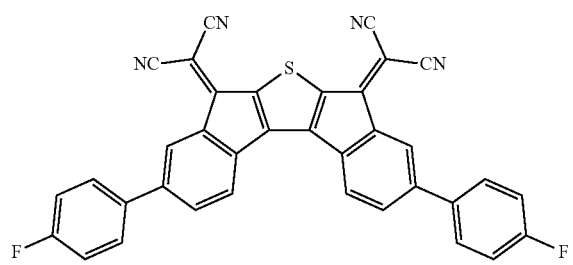
32
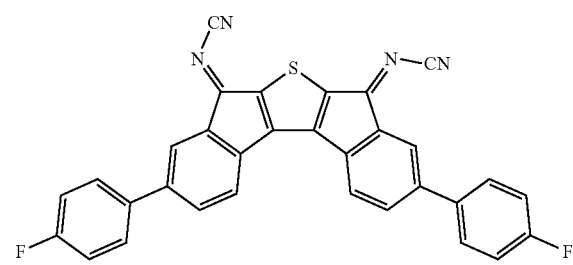
33
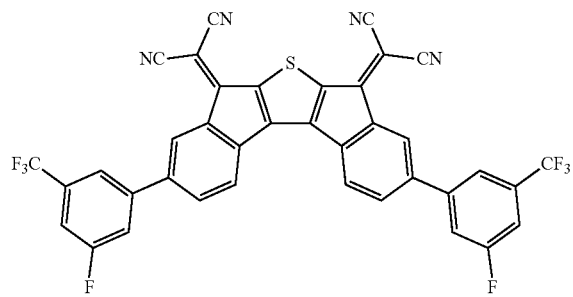
34
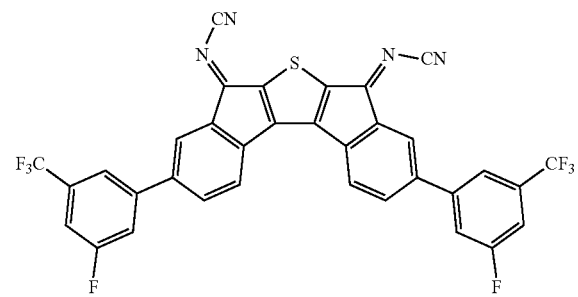
35
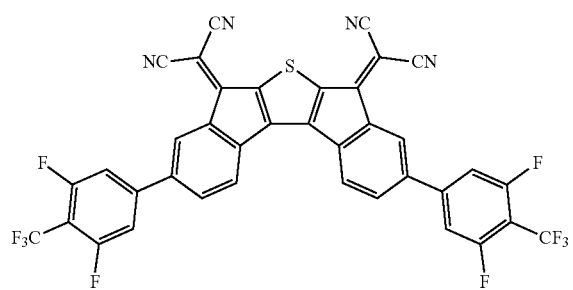
36
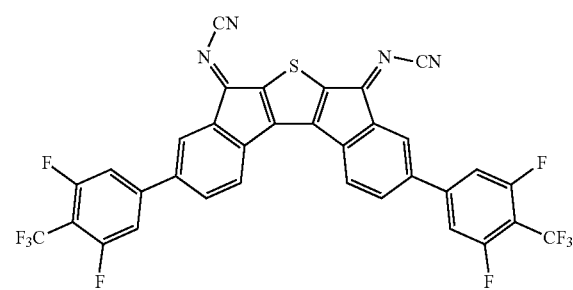

-continued
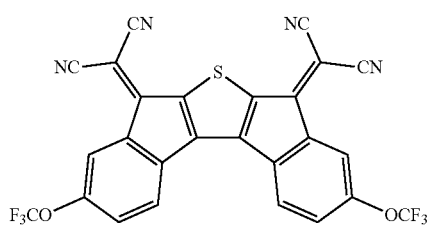
37
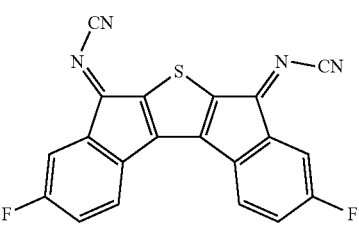
38
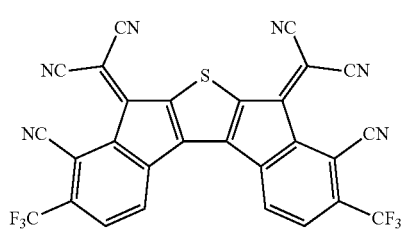
39
40
41
42
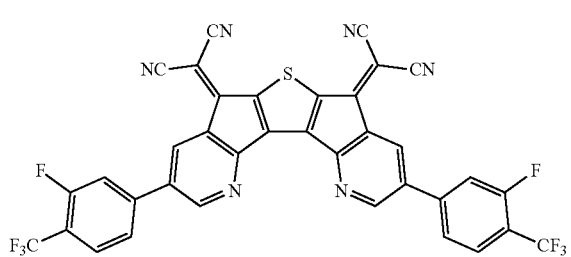
43
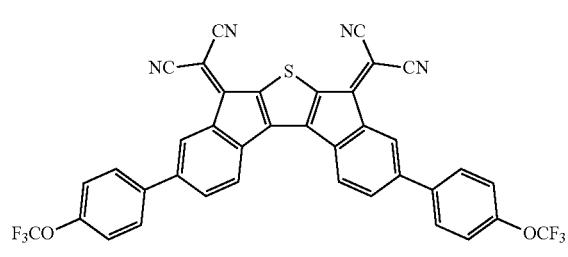
44
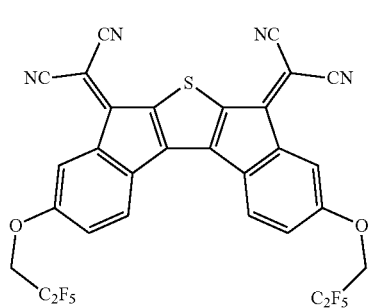
45
46
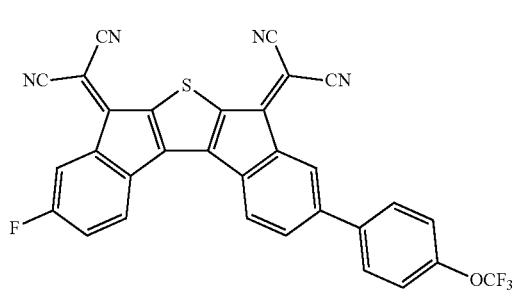
47
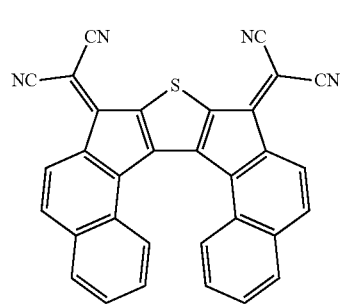
48

-continued
49
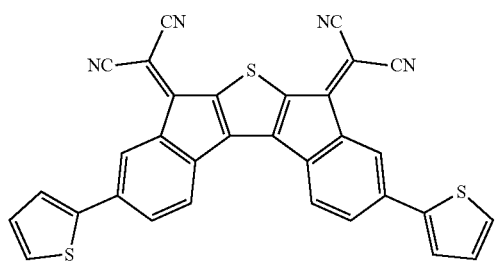
50
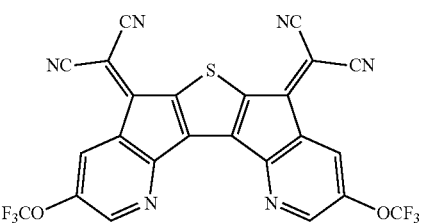
51
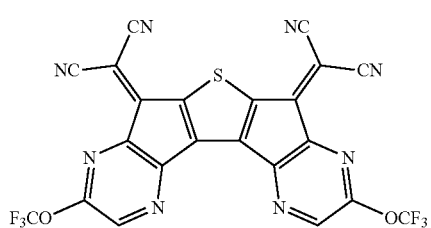
52
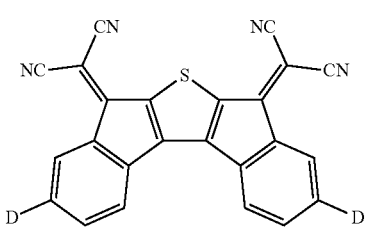
53
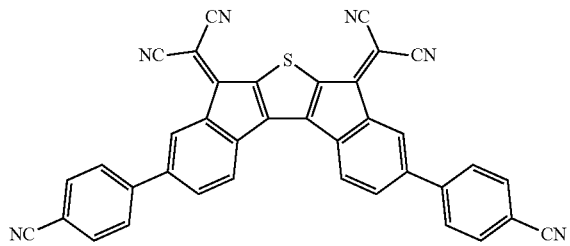
54
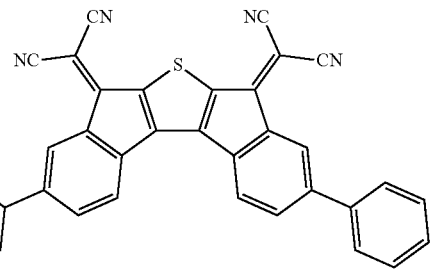
55
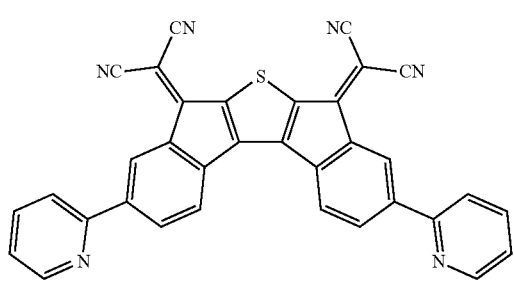
56
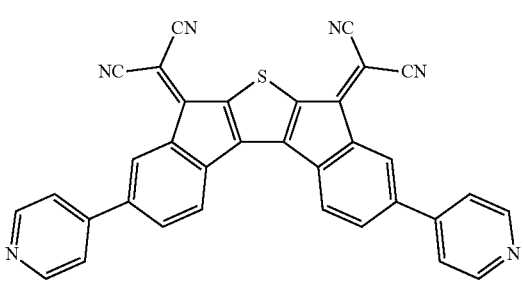
57
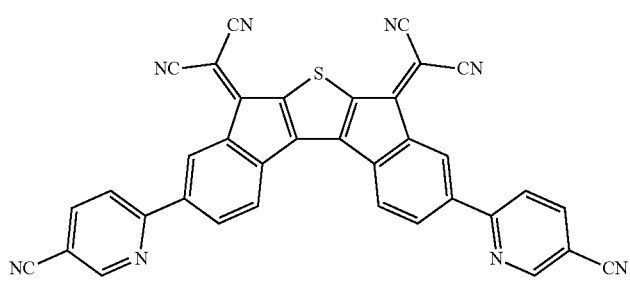
58
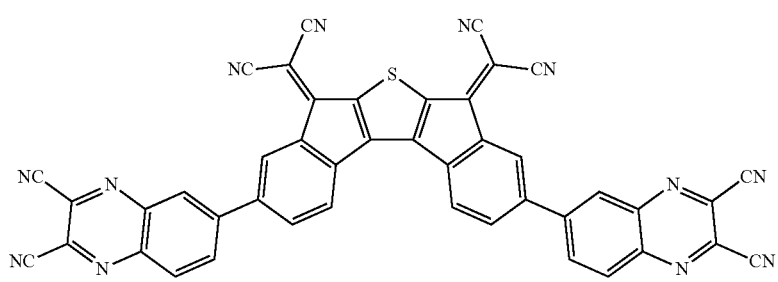

-continued
59
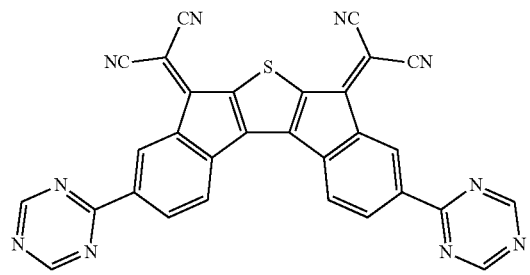
60
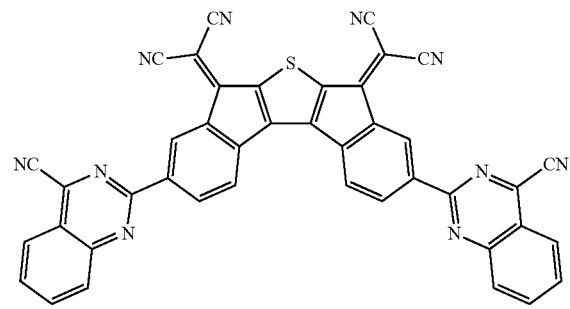
61
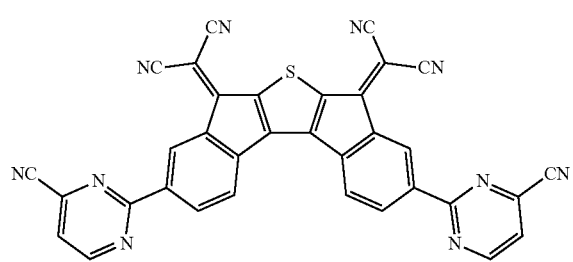
62
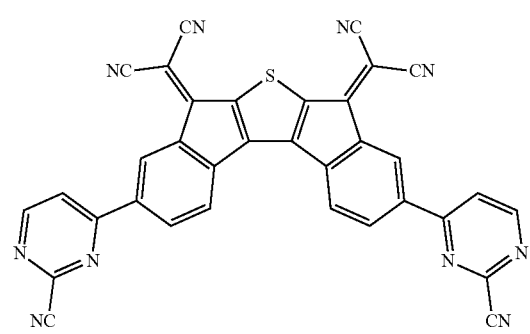
63
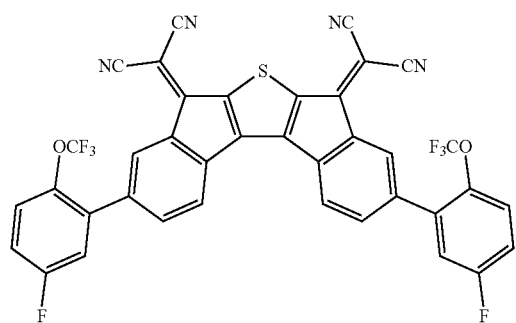
64
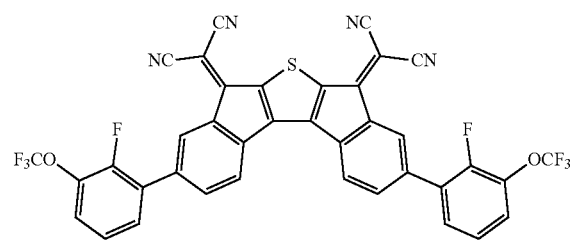
65
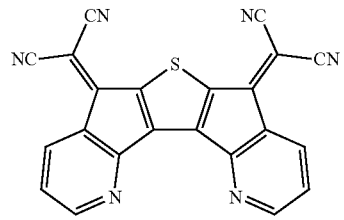
66
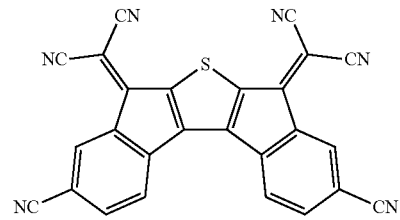
67
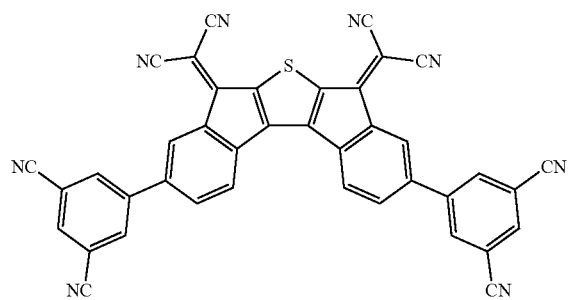
68
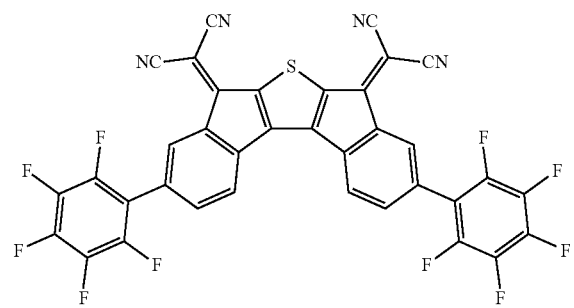

-continued
69
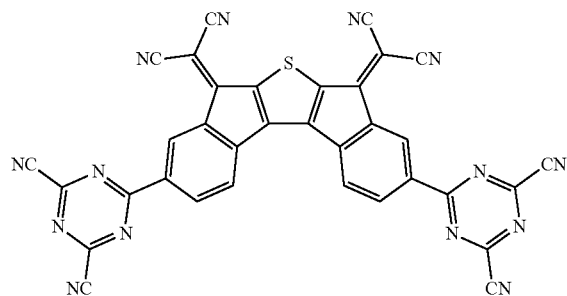
70
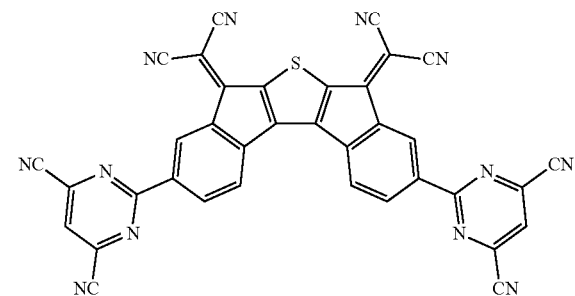
71
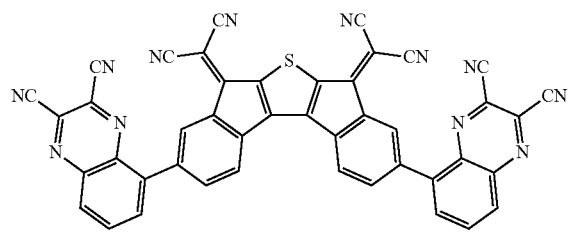
72
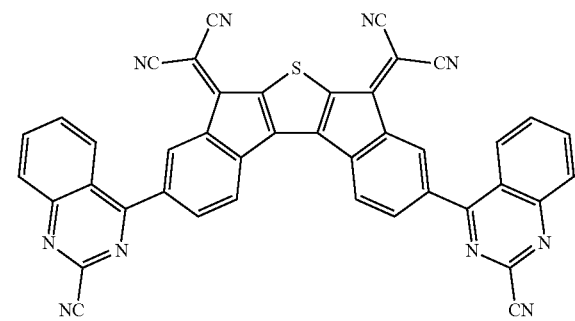
73
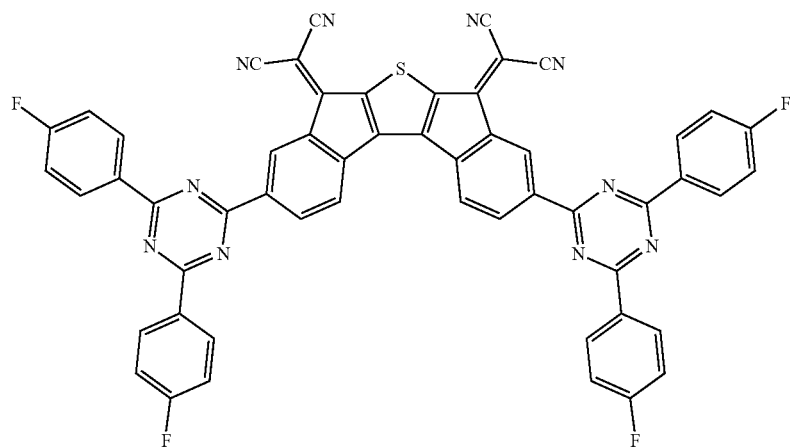
74
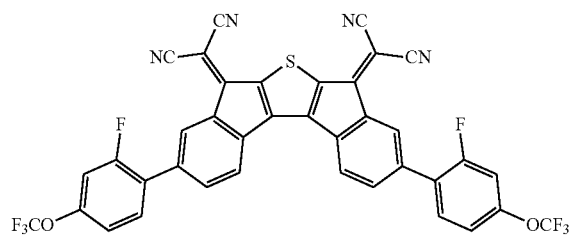
75
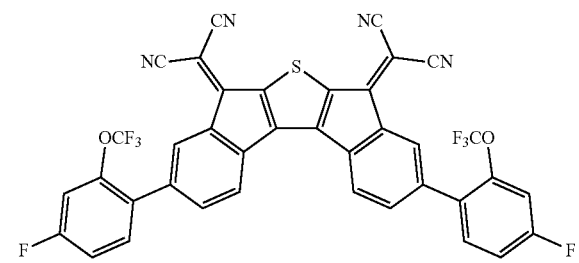

-continued
76
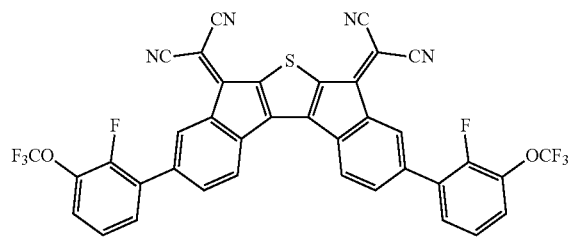
77
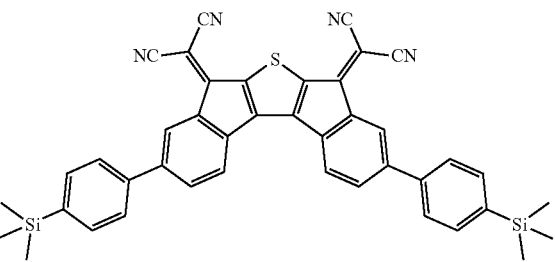
78
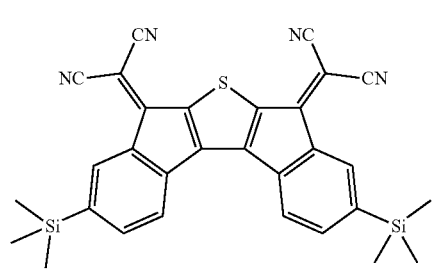
79
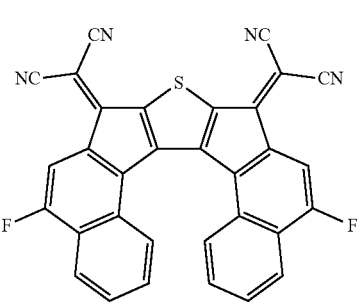
80
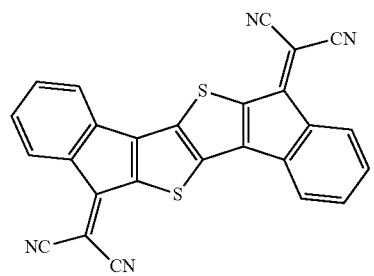
81
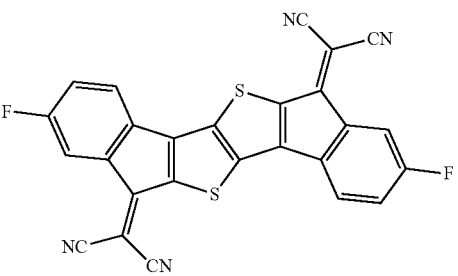
82
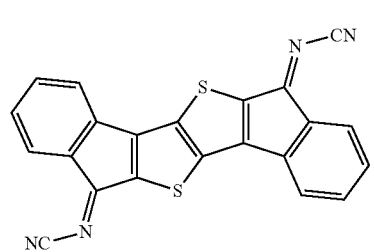
83
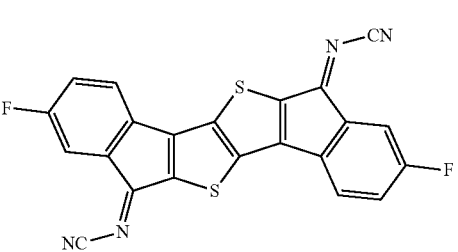
84
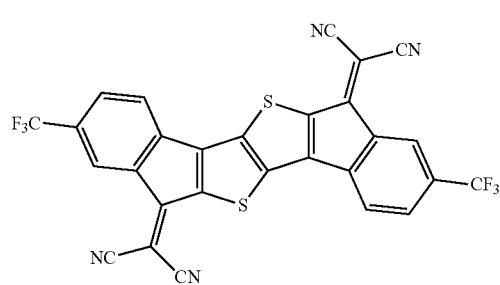
85
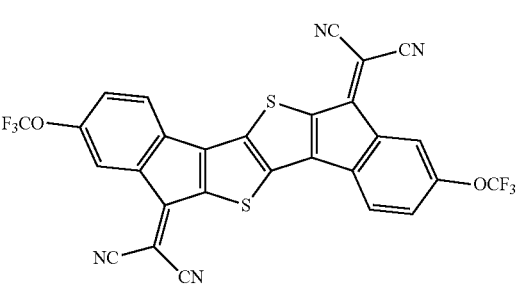
86
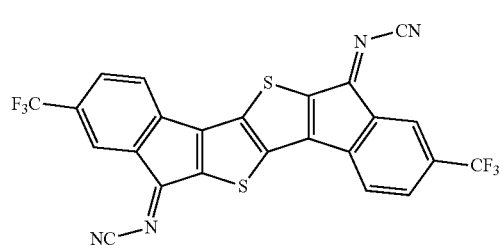
87
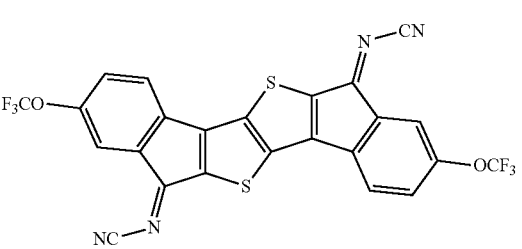

-continued
88
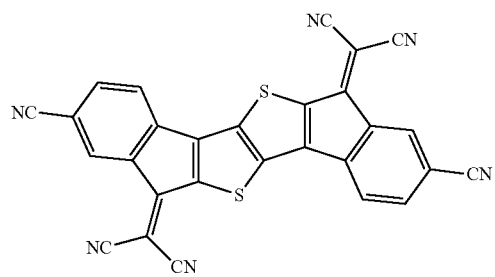
89
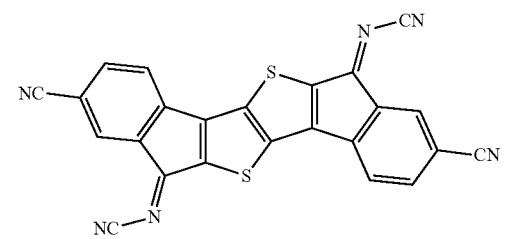
90
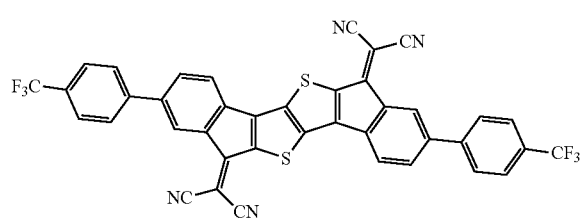
91
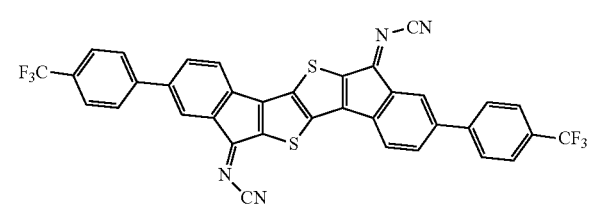
92
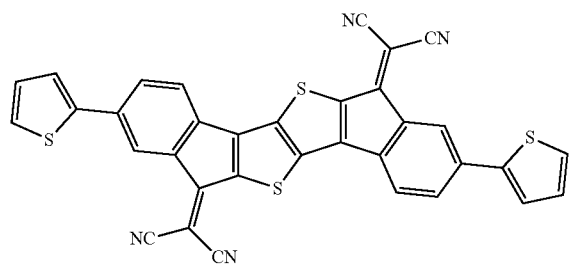
93
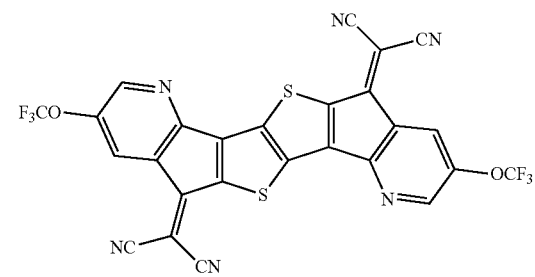
94
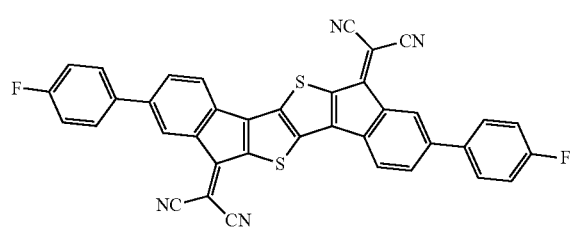
95
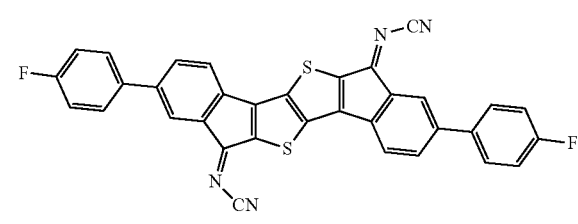
96
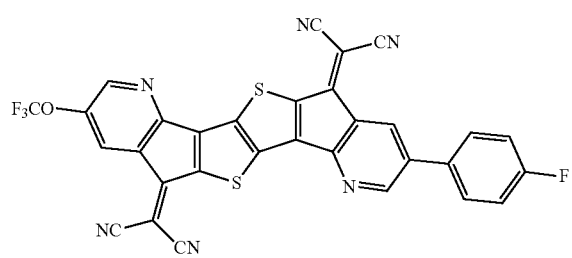
97
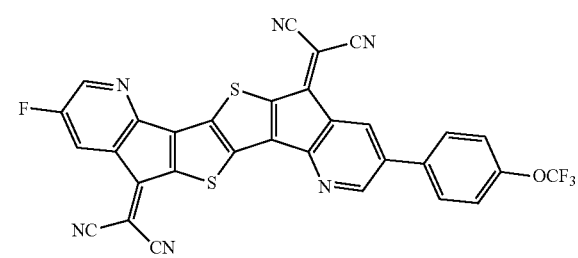
98
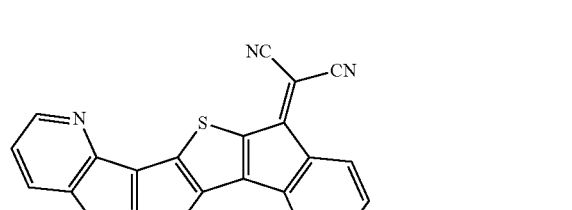
99
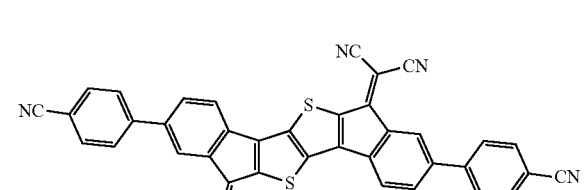

-continued
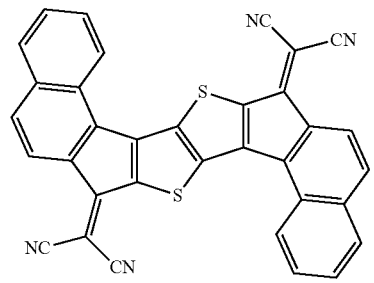
100
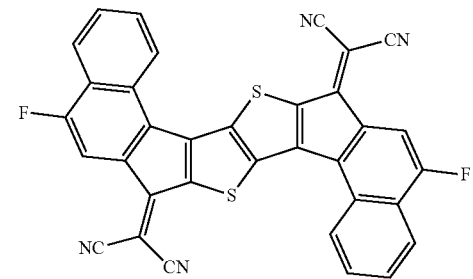
101
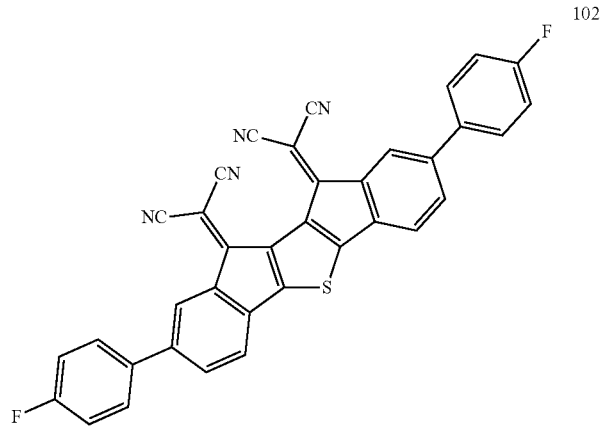
102
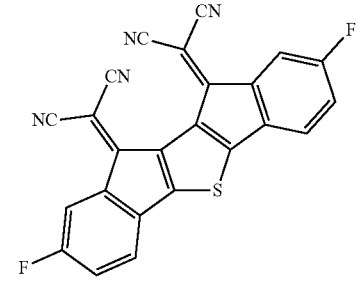
103
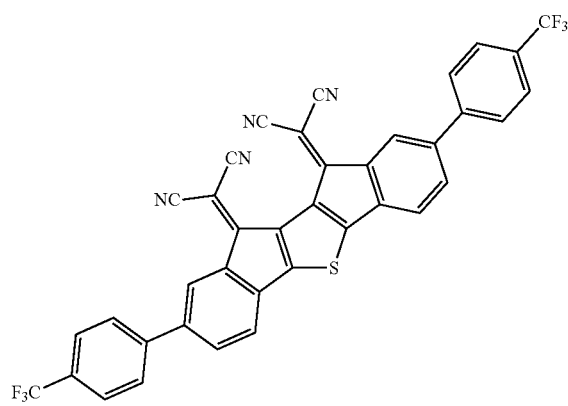
104
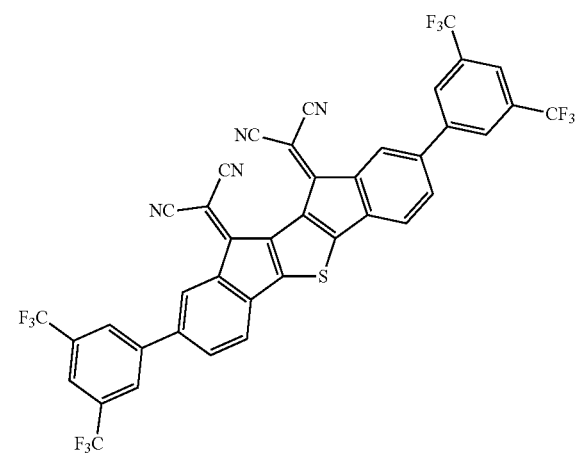
105
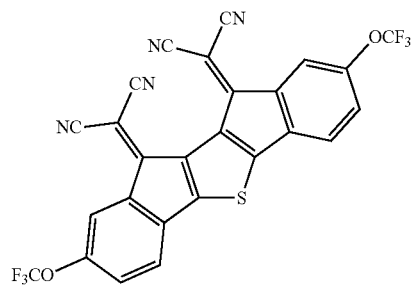
106
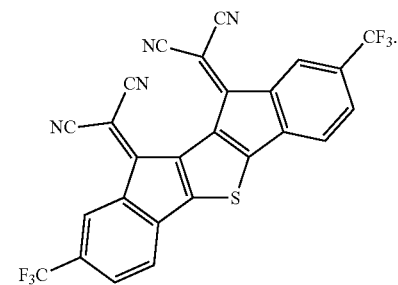
107

6. An organic light emitting device comprising:
a first electrode;
a second electrode; and
one or more organic material layers disposed between the first electrode and the second electrode, wherein one or more layers of the organic material layers comprise the compound of claim 1.

7. The organic light emitting device of claim 6, wherein the organic material layer comprises one or more layers of an electron transport layer, an electron injection layer, and a layer which transports and injects electrons simultaneously, and one or more layers of the layers comprise the compound.

8. The organic light emitting device of claim 6, wherein the organic material layer comprises a light emitting layer, and the light emitting layer comprises the compound as a host of the light emitting layer.

9. The organic light emitting device of claim 6, wherein the organic material layer comprises one or more layers of a hole injection layer, an electron blocking layer, a hole transport layer, and a layer which injects and transports holes simultaneously, and one or more layers of the layers comprise the compound.

10. The organic light emitting device of claim 6, wherein the organic material layer comprises a hole injection layer, and the hole injection layer comprises the compound represented by Chemical Formula 1 as a dopant.

11. The organic light emitting device of claim 6, wherein the organic material layer comprises the compound as a host, and comprises another organic compound, a metal, or a metal compound as a dopant.

12. The organic light emitting device of claim 6, wherein the organic material layer comprises two or more light emitting layers, and comprises a charge generation layer provided between the two light emitting layers, and the charge generation layer comprises the compound.

13. The organic light emitting device of claim 6, wherein the organic material layer comprises a compound represented by the following Chemical Formula 1-A:

[Chemical Formula 1-A]

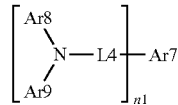

in Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group,
Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and when n1 is 2 or more, two or more structures in the parenthesis are the same as or different from each other.

14. The organic light emitting device of claim 13, wherein L4 is a direct bond, Ar7 is a divalent pyrene group, Ar8 and Ar9 are the same as or different from each other, and are each independently an aryl group having 6 to 30 carbon atoms, which is unsubstituted or substituted with an alkyl group having 1 to 30 carbon atoms, or a substituted or unsubstituted heteroaryl group having 2 to 30 carbon atoms, and n1 is 2.

15. The organic light emitting device of claim 13, wherein the organic material layer comprises a compound represented by the following Chemical Formula 2-A:

[Chemical Formula 2-A]

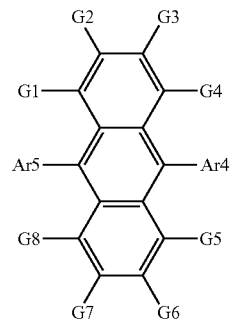

in Chemical Formula 2-A,
Ar4 and Ar5 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted alkyl group; a substituted or unsubstituted monocyclic aryl group; or a substituted or unsubstituted polycyclic aryl group.

16. The organic light emitting device of claim 6, wherein the organic material layer comprises a compound represented by the following Chemical Formula 2-A:

[Chemical Formula 2-A]

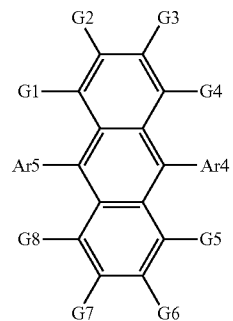

in Chemical Formula 2-A,
Ar4 and Ar5 are the same as or different from each other, and are each independently a substituted or unsubstituted monocyclic aryl group; or a substituted or unsubstituted polycyclic aryl group, and
G1 to G8 are the same as or different from each other, and are each independently hydrogen; a substituted or unsubstituted alkyl group; a substituted or unsubstituted monocyclic aryl group; or a substituted or unsubstituted polycyclic aryl group.

17. The light emitting device of claim 16, wherein Ar4 and Ar5 are a 2-naphthyl group, and G1 to G8 are hydrogen or a substituted or unsubstituted alkyl group.

* * * * *